US010456394B2

(12) United States Patent
Kozikowski et al.

(10) Patent No.: US 10,456,394 B2
(45) Date of Patent: Oct. 29, 2019

(54) TETRAHYDROQUINOLINE SUBSTITUTED HYDROXAMIC ACIDS AS SELECTIVE HISTONE DEACETYLASE 6 INHIBITORS

(71) Applicant: THE BOARD OF TRUSTEES OF THE UNIVERSITY OF ILLINOIS, Urbana, IL (US)

(72) Inventors: Alan Kozikowski, Chicago, IL (US); Sida Shen, Chicago, IL (US); Joel Bergman, Chicago, IL (US); Irina Gaisina, Berwyn, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 15/998,610

(22) PCT Filed: Feb. 15, 2017

(86) PCT No.: PCT/US2017/017850
§ 371 (c)(1),
(2) Date: Aug. 16, 2018

(87) PCT Pub. No.: WO2017/142883
PCT Pub. Date: Aug. 24, 2017

(65) Prior Publication Data
US 2019/0255046 A1 Aug. 22, 2019

Related U.S. Application Data

(60) Provisional application No. 62/295,729, filed on Feb. 16, 2016.

(51) Int. Cl.
C07D 215/08 (2006.01)
C07D 241/44 (2006.01)
C07D 279/16 (2006.01)
A61K 31/498 (2006.01)
A61K 31/5415 (2006.01)
A61K 31/47 (2006.01)
A61P 35/00 (2006.01)
A61P 37/00 (2006.01)
A61P 25/28 (2006.01)

(52) U.S. Cl.
CPC ............ A61K 31/498 (2013.01); A61K 31/47 (2013.01); A61K 31/5415 (2013.01); A61P 25/28 (2018.01); A61P 35/00 (2018.01); A61P 37/00 (2018.01); C07D 215/08 (2013.01); C07D 241/44 (2013.01); C07D 279/16 (2013.01)

(58) Field of Classification Search
CPC .. A61K 31/498; A61K 31/5415; A61K 31/47; A61P 35/00; A61P 37/00; A61P 25/28; C07D 215/08; C07D 279/16; C07D 241/44
See application file for complete search history.

(56) References Cited

U.S. PATENT DOCUMENTS

2011/0300134 A1 12/2011 van Duzer et al.
2015/0056213 A1 2/2015 Sotomayor et al.

FOREIGN PATENT DOCUMENTS

WO WO-03/060523 A1 7/2003
WO WO-2007/022638 A1 3/2007
WO WO-2008/055068 A2 5/2008

OTHER PUBLICATIONS

Shen, et al., Bicyclic-Capped Histone Deacetylase 6 Inhibitors with Improved Activity in a Model of Axonal Charcot-Marie-Tooth Disease, ACS Chemical Neuroscience, 7(2), 240-258, (2016). (Year: 2016).*
U.S. Appl. No. 13/985,760, filed Dec. 20, 2013, Kozikowski et al.
U.S. Appl. No. 15/182,061, filed Jun. 14, 2016, Kozikowski et al.
U.S. Appl. No. 13/384,724, filed Jun. 7, 2012, Kozikowski et al.
U.S. Appl. No. 13/867,438, filed Apr. 22, 2013, Kozikowski et al.
U.S. Appl. No. 15/756,086, filed Feb. 28, 2018, Kozikowski et al.
Andrews et al., Anti-malarial effect of histone deacetylation inhibitors and mammalian tumour cytodifferentiating agents, Int J. Parasitol., 30(6):761-8 (2000).
Barlev et al., Acetylation of p53 activates transcription through recruitment of coactivators/histone acetyltransferases, Mol. Cell, 8(6):1243-54 (2001).
Bradley et al., Tumor targeting by covalent conjugation of a natural fatty acid to paclitaxel, Clin. Cancer Res., 7(10):3229-38 (2001).
Dal Maso et al., Epidemiology of non-Hodgkin lymphomas and other haemolymphopoietic neoplasms in people with AIDS, Lancet Oncol., 4(2):110-9 (2003).
El-Serag, Hepatocellular carcinoma: an epidemiologic view, J. Clin. Gastroenterol., 35(5 Suppl 2):S72-8 (2002).
Flipo et al., Hydroxamates: relationships between structure and plasma stability, J. Med. Chem., 52(21):6790-802 (2009).
Glen et al., Exposure to anticancer drugs can result in transgenerational genomic instability in mice, Proc. Natl. Acad. Sci. USA, 109(8):2984-8 (2012).
Gu et al., Activation of p53 sequence-specific DNA binding by acetylation of the p53 C-terminal domain, Cell, 90(4):595-606 (1997).
Hernández-Avila et al., Human papilloma virus 16-18 infection and cervical cancer in Mexico: a case-control study, Arch. Med. Res., 28(2):265-71 (1997).

(Continued)

Primary Examiner — Erich A Leeser
(74) Attorney, Agent, or Firm — Marshall, Gerstein & Borun LLP

(57) ABSTRACT

Histone deacetylases inhibitors (HDACIs) and compositions containing the same are disclosed. Methods of treating diseases and conditions wherein inhibition of HDAC provides a benefit, like a cancer, a neurodegenerative disorder, a neurological disease, traumatic brain injury, stroke, malaria, an autoimmune disease, autism, and inflammation, also are disclosed.

19 Claims, 2 Drawing Sheets

(56) References Cited

OTHER PUBLICATIONS

Herrmann et al., Epstein-Barr virus-associated carcinomas: facts and fiction, J. Pathol., 199(2):140-5 (2003).
International Application No. PCT/US17/17850, International Preliminary Report on Patentability, dated Aug. 21, 2018.
International Application No. PCT/US17/17850, International Search Report and Written Opinion, dated Apr. 20, 2017.
Ito et al., MDM2-HDAC1-mediated deacetylation of p53 is required for its degradation, EMBO J., 21(22):6236-45 (2002).
Ito et al., p300/CBP-mediated p53 acetylation is commonly induced by p53-activating agents and inhibited by MDM2, EMBO J., 20(6):1331-40 (2001).
Kadow et al., The role of viruses in human cancer development and antiviral approaches for intervention, Curr. Opin. Investig. Drugs, 3(11):1574-9 (2002).
Kalin et al., Development and therapeutic implications of selective histone deacetylase 6 inhibitors, J. Med. Chem., 56(16):6297-313 (2013).
Kozikowski et al., Functional differences in epigenetic modulators-superiority of mercaptoacetamide-based histone deacetylase inhibitors relative to hydroxamates in cortical neuron neuroprotection studies, J. Med. Chem., 50(13):3054-61 (2007).
Lakshmaiah et al., Epigenetic therapy of cancer with histone deacetylase inhibitors, J. Cancer Res. Ther., 10(3):469-78 (2014).
Liu et al., p53 sites acetylated in vitro by PCAF and p300 are acetylated in vivo in response to DNA damage, Mol. Cell Biol., 19(2):1202-9 (1999).
Ma et al., Asymmetric dipolar cycloaddition reactions: a practical, convergent synthesis of chiral pyrrolidines, Tetrahedron: Asymmetry, 8(6):883-7 (1997).
Mortreux et al., Molecular and cellular aspects of HTLV-1 associated leukemogenesis in vivo, Leukemia, 17(1):26-38 (2003).
Sakaguchi et al., DNA damage activates p53 through a phosphorylation-acetylation cascade, Genes Dev., 12(18):2831-41 (1998).
Segretti et al., Thiol-Based Potent and Selective HDAC6 Inhibitors Promote Tubulin Acetylation and T-Regulatory Cell Suppressive Function, ACS Med. Chem. Lett., 6(11):1156-61 (Oct. 2015).
Tao et al., Deacetylase inhibition promotes the generation and function of regulatory T cells, Nat. Med., 13(11):1299-307 (2007).
Shen et al., Bicyclic-Capped Histone Deacetylase 6 Inhibitors with Improved Activity in a Model of Axonal Charcot-Marie-Tooth Disease, ACS Chem. Neurosci., 7(2):240-58 (Feb. 2016).

* cited by examiner

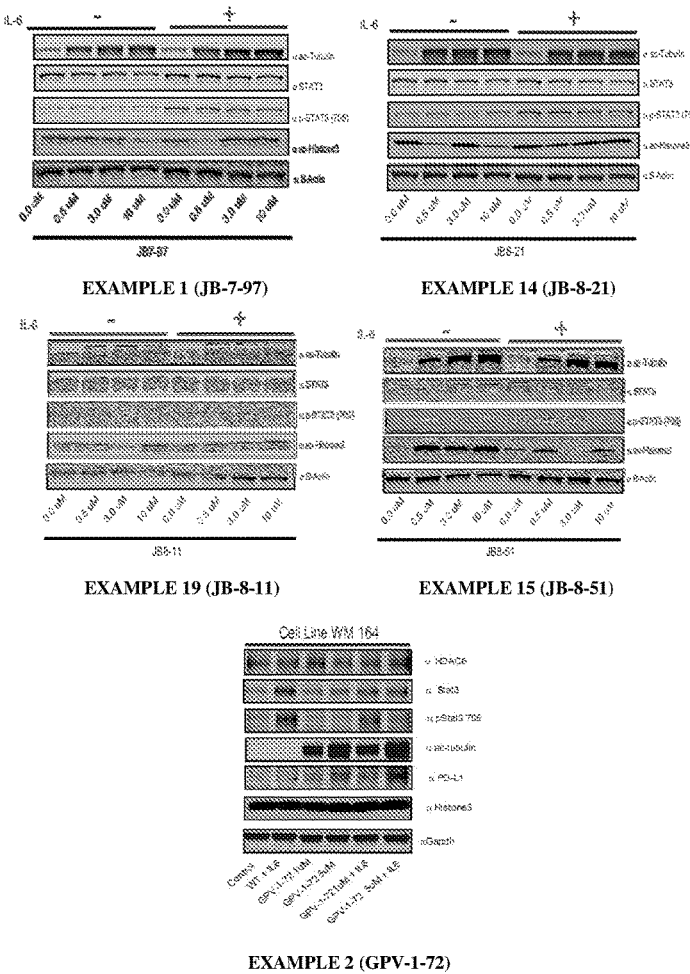
Figure 1. Western blots for tubulin acetylation and other proteins assayed in WM164 cancer cell lines.
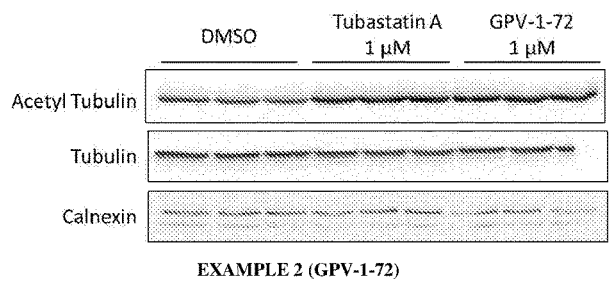
Figure 2. Results of the tubulin acetylation test in adult rat cardiac fibroblasts.

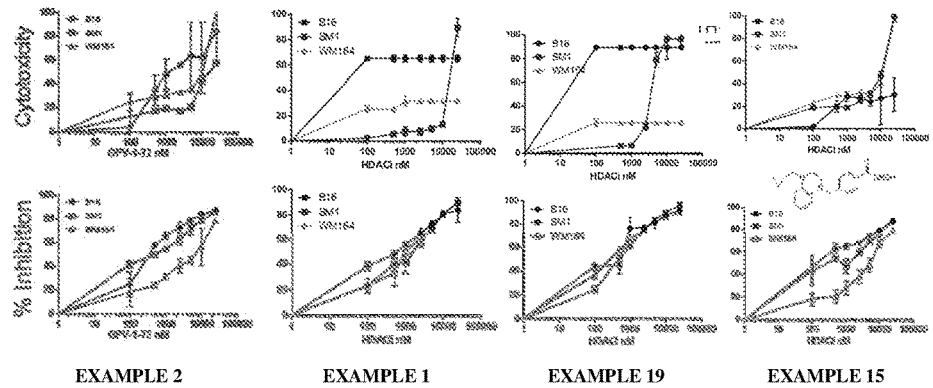
Figure 3. Results of cellular cytotoxicity and HDAC inhibition assays conducted using B16, SM1, and WM164 cancer cell lines, respectively.
Potency in GBM6 cells with and without Temozolomide
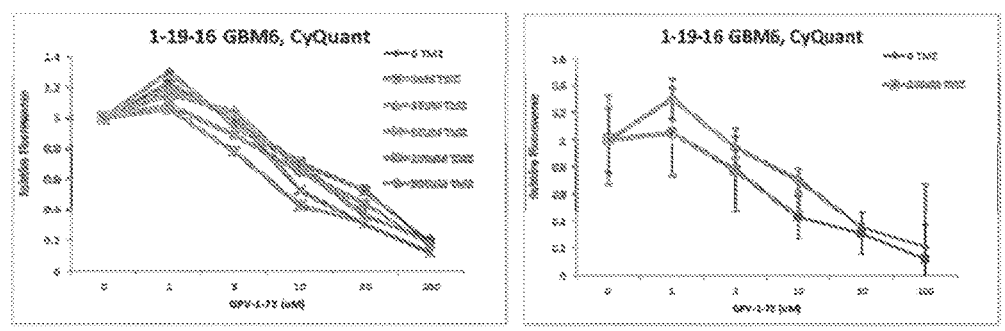
Figure 4. Cellular cytotoxicity of Example 2 compound on GBM6 cells with and without added temozolomide.

TETRAHYDROQUINOLINE SUBSTITUTED HYDROXAMIC ACIDS AS SELECTIVE HISTONE DEACETYLASE 6 INHIBITORS

CROSS-REFERENCE TO RELATED APPLICATIONS

This is a U.S. national phase of International Application No. PCT/US2017/017850, filed Feb. 15, 2017, which claims the benefit of U.S. Provisional Application No. 62/295,729, filed Feb. 16, 2016, incorporated herein by reference in its entirety.

STATEMENT OF GOVERNMENTAL INTEREST

This invention was made with government support under grant number R01 NS079183 awarded by the National Institutes of Health. The government has certain rights in this invention.

FIELD OF THE INVENTION

The present invention relates to histone deacetylase inhibitors (HDACIs), to pharmaceutical compositions comprising one or more of the HDACIs, to methods of increasing the sensitivity of cancer cells to the cytotoxic effects of radiotherapy and/or chemotherapy comprising contacting the cell with one or more of the HDACIs, and to therapeutic methods of treating conditions and diseases wherein inhibition of HDAC provides a benefit, for example, a cancer, an inflammation, a neurological disease, a neurodegenerative disorder, stroke, traumatic brain injury, allograft rejection, autoimmune diseases, and malaria, comprising administering a therapeutically effective amount of a present HDACI to an individual in need thereof.

BACKGROUND OF THE INVENTION

Covalent post-translational modifications (PTMs) of epigenomic proteins contribute to their biological roles, and thus serve as carriers of epigenetic information from one cell generation to the next. Epigenetics means on top of or above genetics, and refers to external modifications to DNA and associated histones that turn genes "on" or "off." These modifications do not change the DNA sequence, but instead, they affect how cells "read" genes. PTMs play key roles in the regulation of protein function, transcription, DNA replication, and repair of DNA damage (Lakshmaiah, K. C et al., J. Cancer Res. Ther. 2014, 10, 469-478).

The major events surrounding epigenetic control are focused on three modes of action: writers, readers, and erasers. The writers are responsible for adding a variety of PTM marks to histones which include, inter alia, acetylation which is catalyzed by histone acetyltransferases (HATs). Readers refer to the proteins that recognize and bind to these PTM marks thereby mediating their effects, and erasers encompass various enzymes such as the histone deacetylases (HDACs) that catalyze the removal of these marks. In the case of acetylated histone lysine residues, HDACs are responsible for catalyzing the hydrolysis of the acetyl mark to provide the unsubstituted lysine residue. The HDAC family consists of at present 18 enzymes which are classified into four subgroups according to their homology to the yeast family. HDAC1, 2, 3 and 8—categorized as class I HDACs according to their homology with yeast Rpd3—are characterized by ubiquitous expression and localization to the nucleus. Class II HDACs show tissue-specific expression and shuttle between the nucleus and cytoplasm. Homologous to yeast Hda1, these enzymes are subdivided in class IIa (HDAC4, 5, 7 and 9) and class IIb (HDAC6 and 10). HDAC11, the only member of the class IV subfamily, shows similarities to the catalytic domains of both class I and II enzymes. Class I, II, and IV HDACs require $Zn^{2+}$ as a cofactor of the deacetylating activity and are also referred to as the conventional HDACs. The sirtuins 1-7 are dependent on nicotinamide adenine dinucleotide for their activity and form class III of the HDACs.

Pharmacologic manipulation of the enzymes involved in regulating protein PTMs, especially those tied to very specific PTM marks, holds tremendous possibilities in better understanding the workings of the cell. The discovery of selective small molecule modulators of these enzymes would provide chemical tools to better understand the role of these PTMs at the cellular level, but may also lead to important disease modifiers. Within the HDAC field, there exists a plethora of compounds that are able to block the deacetylase enzymes, and several have made their way to the marketplace for cancer therapy. The majority of these HDACIs, however, are not very isoform selective. Many of them inhibit across more than one class of HDAC enzymes and are thus labeled pan-selective. Of the various HDAC isoforms that appear to be promising therapeutic targets for treating human diseases such as cancer and certain CNS disorders, HDAC6 has emerged as a particularly attractive target, especially in view of the fact that HDAC6 knockout animals remain viable. HDAC6 has no apparent role in the PTM of histone proteins, but rather is involved in regulating the acetylation status of α-tubulin, HSP-90, cortactin, HSF-1, and other protein targets. This enzyme also plays a role in the recognition and clearance of polyubiquitinated misfolded proteins from the cell through aggresome formation. The development of HDAC6 selective compounds has recently been reviewed (Kalin, J. H. et al., J. Med. Chem. 2013, 56, 6297-6313). In general, HDACIs are comprised of three main motifs: a zinc binding group (ZBG), a cap group, and a linker that bridges the previous two (FIG. 1). A properly optimized cap group can improve both potency and selectivity, presumably through its ability to engage in appropriate contacts with residues on the enzyme surface.

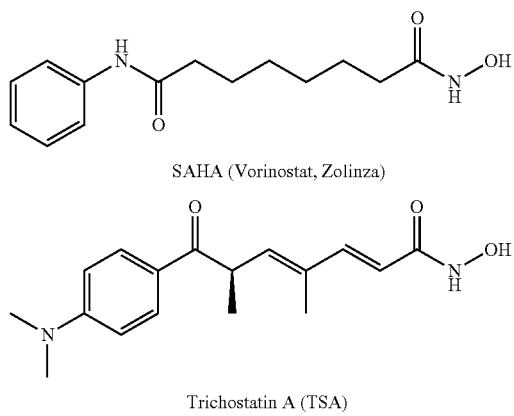

FIG 1.
Structures of SAHA, TSA, and general structure of an HDAC inhibitor.

SAHA (Vorinostat, Zolinza)

Trichostatin A (TSA)

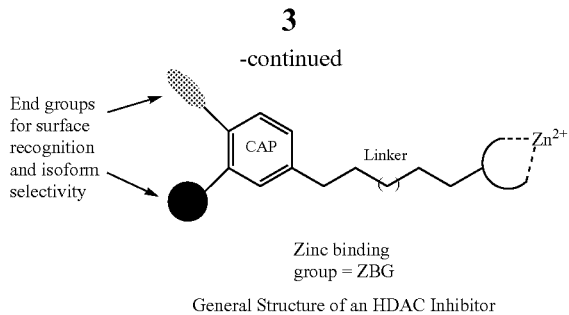

General Structure of an HDAC Inhibitor

Many HDACIs such as trichostatin A (TSA) and SAHA contain a hydroxamic acid function as ZBG (FIG. 1). Unfortunately, hydroxamates are in some cases metabolically unstable (short half-life), and their potent metal-chelating ability might lead to off-target activity at other zinc-containing enzymes (Flipo, M. et al., J. Med. Chem. 2009, 52, 6790-6802). In addition, many of the hydroxamic acid based inhibitors have been found to be Ames-positive, suggesting that these agents might present genotoxic effects. While several of the HDACIs on the market are Ames positive and cause chromosomal aberrations, these are being used only for cancer, wherein this undesired side effect can to a certain extent be tolerated in a disease considered to be life threatening. Certainly, for use in diseases that would require chronic, longer term use of an HDACI, it would be preferable to have compounds that are not Ames positive/genotoxic. However, even for cancer, it is known that use of genotoxic agents can lead to a genomic instability that may be transmitted to offspring in cases where the treated adults have children (Glen, C. D. et al., Proc. Natl. Acad. Sci. U.S.A. 2012, 109, 2984-2988). As such, there is a great need for the discovery of potent and selective HDACIs that bear alternative ZBGs or that are hydroxamates that for various reasons fail to show Ames activity. Our research has led to the discovery of hydroxamate based HDACIs that show high selectivity for the inhibition of HDAC6 but are not Ames active (Kozikowski, A. P. et al., J. Med. Chem. 2007, 50, 3054-3061).

In summary, extensive evidence supports a therapeutic role for HDACIs in the treatment of a variety of conditions and diseases, such as cancers and CNS diseases and degenerations. However, despite exhibiting overall beneficial effects, like beneficial neuroprotective effects, for example, HDACIs known to date have little specificity with regard to HDAC inhibition, and therefore inhibit all zinc-dependent histone deacetylases. It is still unknown which is (are) the salient HDAC(s) that mediate(s) neuroprotection when inhibited. Emerging evidence suggests that at least some of the HDAC isozymes are absolutely required for the maintenance and survival of neurons, e.g., HDAC1. Additionally, adverse side effect issues have been noted with nonspecific HDAC inhibition. Thus, the clinical efficacy of present-day nonspecific HDACIs for stroke, neurodegenerative disorders, neurological diseases, and other diseases and conditions ultimately may be limited. It is important therefore to design, synthesize, and test compounds capable of serving as potent, and preferably isozyme-selective, HDACIs that are able to ameliorate the effects of neurological disease, neurodegenerative disorder, traumatic brain injury, cancer, inflammation, malaria, autoimmune diseases, immunosuppressive therapy, and other conditions and diseases mediated by HDACs.

An important advance in the art would be the discovery of HDACIs, and particularly selective HDAC6 inhibitors, that are useful in the treatment of diseases wherein HDAC inhibition provides a benefit, such as cancers, neurological diseases, traumatic brain injury, neurodegenerative disorders and other peripheral neuropathies, stroke, hypertension, malaria, allograft rejection, rheumatoid arthritis, and inflammations. Accordingly, a significant need exists in the art for efficacious compounds, compositions, and methods useful in the treatment of such diseases, alone or in conjunction with other therapies used to treat these diseases and conditions. The present invention is directed to meeting this need.

SUMMARY OF THE INVENTION

The present invention relates to histone deacetylase inhibitors (HDACIs), pharmaceutical compositions comprising the HDACI, and methods of treating diseases and conditions wherein inhibition of HDAC provides a benefit, such as a cancer, a neurological disease, a psychiatric illness, a neurodegenerative disorder, a peripheral neuropathy, stroke, hypertension, an inflammation, traumatic brain injury, rheumatoid arthritis, allograft rejection, sepsis, and autoimmune diseases, comprising administering a therapeutically effective amount of an HDACI to an individual in need thereof. The present invention also relates to a method of increasing the sensitivity of a cancer cell to radiotherapy and/or chemotherapy. The present invention also allows for the use of these HDAC inhibitors in combination with other drugs and/or therapeutic approaches. In some embodiments, the present HDACIs exhibit selectivity for particular HDAC isozymes, such as HDAC6, over other HDAC isozymes. In particular, the invention concerns the discovery of compounds containing the tetrahydroquinoline moiety or an analog thereof as the cap residue.

More particularly, the present invention relates to histone deacetylase inhibitors (HDACIs) having a structural formula:

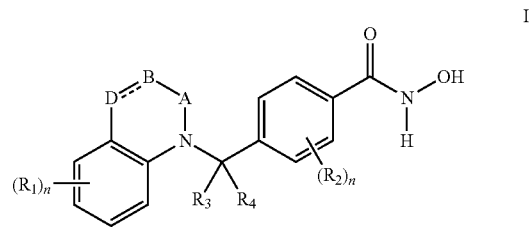

or a pharmaceutically acceptable salt thereof, wherein:
═══ represents a single or double bond;
n=0, 1, or 2;
$R_1$ and $R_2$ are independently selected from the group consisting of hydrogen, halogen, hydroxyl, trifluoromethyl, cyano, —$NR_aR_b$, —$C(O)NR_aR_b$, acetyl, $C_1$-$C_6$ alkyl, $C_1$-$C_6$ alkenyl, $C_1$-$C_6$ alkynyl, $C_1$-$C_6$ alkoxy, $C_1$-$C_6$ haloalkyl, $C_1$-$C_6$ alkoxy, $C_3$-$C_6$ cycloalkyl, aryl, heteroaryl, or $C_5$-$C_6$ heterocyclyl;
$R_a$ and $R_b$ are independently selected from the group consisting of hydrogen, $C_1$-$C_6$ alkyl or branched alkyl, or these groups may be joined to form a 3-7 membered heterocycyl;
A is $CR_cR_d$ or C═O;
B is $CR_cR_d$ when ═══ represents a single bond or $CR_c$ when ═══ represents a double bond;
D is $CR_cR_d$, C═O, $NR_c$, O, S, S═O when ═══ represents a single bond or $CR_c$ or N when ═══ represents a double bond;

$R_c$ and $R_d$ are independently hydrogen, $C_1$-$C_6$ alkyl, or are joined together to form a 3-6 membered cycloalkyl;

$R_e$ is independently selected from the group consisting of hydrogen, $C_1$-$C_6$ alkyl, $C_3$-$C_6$ cycloalkyl, aryl, heteroaryl, or $C_5$-$C_6$ heterocycloalkyl; and $R_3$ and $R_4$ are independently selected from the group consisting of hydrogen and $C_1$-$C_6$ alkyl; in the case where one of $R_3$ or $R_4$ is a hydrogen atom, and the other group is alkyl, a chiral center is generated which may be of the R or S configuration.

BRIEF DESCRIPTION OF THE FIGURES

FIG. 1 contains Western blots for tubulin acetylation and other proteins assayed in WM164 cancer cell lines for Examples 1, 2, 14, 15, and 19;

FIG. 2 illustrates the results of a tubulin acetylation test in adult rat cardiac fibroblasts for Example 2;

FIG. 3 contains plots for the results of cellular cytotoxicity and HDAC inhibition assays conducted using B16, SM1, and WM164 cancer cell lines; and FIG. 4 contains plots showing the cellular cytotoxicity of Example 2 on GBM6 cells with and without temozolomide.

DETAILED DESCRIPTION OF THE INVENTION

Definitions

The following terms and expressions used herein have the indicated meanings. Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, C1-C6alkoxycarbonyloxy and —OC(O)C1-C6 alkyl indicate the same functionality; similarly arylalkyl and -alkylaryl indicate the same functionality.

"Acetyl" means a group of formula —C(O)CH$_3$.

"Alkenyl" means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

"Alkynyl" means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

"Alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkyl" means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH2-, -CH2CH2-, —CH2CH2CHC(CH3)-, and —CH2CH(CH2CH3)CH2-.

"Aryl," means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, and the like. The aryl is attached to the parent molecular moiety through any carbon atom contained within the aryl ring system. In certain embodiments, the aryl group is phenyl or naphthyl. In certain other embodiments, the aryl group is phenyl.

"Cyano" and "nitrile" mean a —CN group.

"Cycloalkyl" means a 3-6 membered monocyclic ring. The cycloalkyl may be saturated or unsaturated, but not aromatic. Representative cycloalkyl include, but are not limited to cyclopropyl, cyclobutyl, cyclopentyl, cyclopentenyl, cyclohexyl and cyclohexenyl.

"Halo" or "halogen" means —Cl, —Br, —I or —F.

"Haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

"Heteroaryl" means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4

(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. In certain embodiments of the disclosure, the heteroaryl group is furyl, imidazolyl, pyridinyl, pyrimidinyl, pyrazinyl, pyrazolyl, pyrrolyl, thiazolyl, thienyl, triazolyl, benzimidazolyl, benzofuranyl, indazolyl, indolyl, quinolinyl, and the like.

"Heterocyclyl" means a monocyclic 5 or 6 membered heterocyclic ring containing at least one N atom and optionally one or more additional heteroatoms independently selected from O, N, and S where the ring is saturated or unsaturated, but not aromatic. Representative examples of monocyclic heterocycle include, but are not limited to, imidazolinyl, imidazolidinyl, isothiazolinyl, isothiazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, thiopyranyl. In certain embodiments, the heterocyclyl is imidazolinyl, pyrrolidinyl, piperidinyl, or piperazinyl.

The present invention is directed to novel HDACIs of formula I, Ib, and Ic and their use in therapeutic treatments of, for example, cancers, inflammations, traumatic brain injuries, neurodegenerative disorders, neurological diseases, peripheral neuropathies, strokes, hypertension, autoimmune diseases, inflammatory diseases, and malaria. The present HDACIs also increase the sensitivity of a cancer cell to the cytotoxic effects of radiotherapy and/or chemotherapy. In some embodiments, the present HDACIs selectively inhibit HDAC6 over other HDAC isozymes.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "a disease or condition wherein inhibition of HDAC provides a benefit" pertains to a condition in which HDAC and/or the action of HDAC is important or necessary, e.g., for the onset, progress, expression of that disease or condition, or a disease or a condition which is known to be treated by an HDAC inhibitor (such as, e.g., TSA, pivaloyloxymethylbutane (AN-9; Pivanex), FK-228 (Depsipeptide), PXD-101, NVP-LAQ824, SAHA, MS-275, and or MGCD0103). Examples of such conditions include, but are not limited to, cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spinocerebellar degeneration, Rett syndrome), peripheral neuropathies (Charcot-Marie-Tooth disease, Giant Axonal Neuropathy (GAN)), inflammatory diseases (e.g., osteoarthritis, rheumatoid arthritis, colitis), diseases involving angiogenesis (e.g., cancer, rheumatoid arthritis, psoriasis, diabetic retinopathy), hematopoietic disorders (e.g., anemia, sickle cell anemia, thalasseimia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants). One of ordinary skill in the art is readily able to determine whether a compound treats a disease or condition mediated by HDAC for any particular cell type, for example, by assays which conveniently can be used to assess the activity of particular compounds.

The term "second therapeutic agent" refers to a therapeutic agent different from a present HDACI and that is known to treat the disease or condition of interest. For example, when a cancer is the disease or condition of interest, the second therapeutic agent can be a known chemotherapeutic drug, like taxol, or radiation, for example.

The term "HDAC" refers to a family of enzymes that remove acetyl groups from a protein, for example, the ε-amino groups of lysine residues at the N-terminus of a histone. The HDAC can be a human HDAC, including, HDAC1, HDAC2, HDAC3, HDAC4, HDAC5, HDAC6, HDAC7, HDAC8, HDAC9, HDAC10, and HDAC11. The HDAC also can be derived from a protozoal or fungal source.

The terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce HDAC signaling in the target cells; and/or relieve, to some extent, one or more of the symptoms associated with the cancer. To extent the administered compound or composition prevents growth and/or kills existing cancer cells, it may be cytostatic and/or cytotoxic.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a present HDACI can be administered at the same time or sequentially in any order at different points in time as a second therapeutic agent. A present HDACI and the second therapeutic agent can be administered separately, in any appropriate form and by any suitable route. When a present HDACI and the second therapeutic agent are not administered concurrently, it is understood that they can be administered in any order to a subject in need thereof. For example, a present HDACI can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a present HDACI and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the invention and is not a limitation on the scope of the invention unless otherwise claimed. No language in the specification should be construed as indicating any non-claimed element as essential to the practice of the invention.

In particular, the present invention is directed to HDACIs, compositions comprising the present HDACI, and therapeutic uses of the HDACIs of formula I, or a pharmaceutically acceptable salt or prodrug thereof:

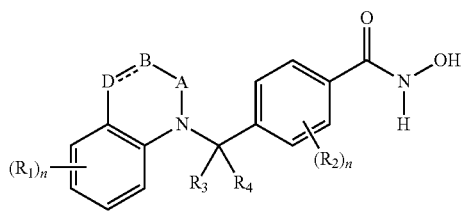

I or a pharmaceutically acceptable salt thereof, wherein:

═══ represents a single or double bond;

n=0, 1, or 2;

$R_1$ and $R_2$ are independently selected from the group consisting of hydrogen, halogen, hydroxyl, trifluoromethyl, cyano, —$NR_aR_b$, —$C(O)NR_aR_b$, acetyl, $C_1$-$C_6$ alkyl, $C_1$-$C_6$ alkenyl, $C_1$-$C_6$ alkynyl, $C_1$-$C_6$ alkoxy, $C_1$-$C_6$ haloalkyl, $C_1$-$C_6$ alkoxy, $C_3$-$C_6$ cycloalkyl, aryl, heteroaryl, or $C_5$-$C_6$ heterocyclyl;

$R_a$ and $R_b$ are independently selected from the group consisting of hydrogen, $C_1$-$C_6$ alkyl or branched alkyl, or these groups may be joined to form a 3-7 membered heterocycyl;

A is $CR_cR_d$ or C═O;

B is $CR_cR_d$ when ═══ represents a single bond or $CR_c$ when ═══ represents a double bond;

D is $CR_cR_d$, C═O, $NR_e$, O, S, S═O when ═══ represents a single bond or $CR_c$ or N when ═══ represents a double bond;

$R_c$ and $R_d$ are independently hydrogen, $C_1$-$C_6$ alkyl, or are joined together to form a 3-6 membered cycloalkyl;

$R_e$ is independently selected from the group consisting of hydrogen, $C_1$-$C_6$ alkyl, $C_3$-$C_6$ cycloalkyl, aryl, heteroaryl, or $C_5$-$C_6$ heterocycloalkyl; and $R_3$ and $R_4$ are independently selected from the group consisting of hydrogen and $C_1$-$C_6$ alkyl; in the case where one of $R_3$ or $R_4$ is a hydrogen atom, and the other group is alkyl, a chiral center is generated which may be of the R or S configuration.

In an embodiment, this invention comprises HDACIs of formula Ib

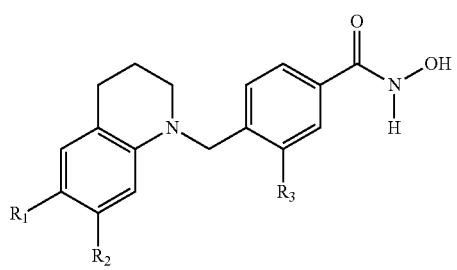

Ib wherein $R_1$, $R_2$, and $R_3$ are independently selected from the group consisting of hydrogen, halogen, hydroxyl, trifluoromethyl, cyano, —$NR_aR_b$, —$C(O)NR_aR_b$, acetyl, $C_1$-$C_6$ alkyl, $C_1$-$C_6$ alkenyl, $C_1$-$C_6$ alkynyl, $C_1$-$C_6$ alkoxy, $C_1$-$C_6$ haloalkyl, $C_1$-$C_6$ alkoxy, $C_3$-$C_6$ cycloalkyl, aryl, heteroaryl, and $C_5$-$C_6$ heterocycloalkyl; and $R_a$ and $R_b$ are independently selected from the group consisting of hydrogen, $C_1$-$C_6$ alkyl and branched alkyl, or these groups may be joined to form a 3-7 membered heterocyclyl.

In another embodiment, comprises HDACIs of formula Ic

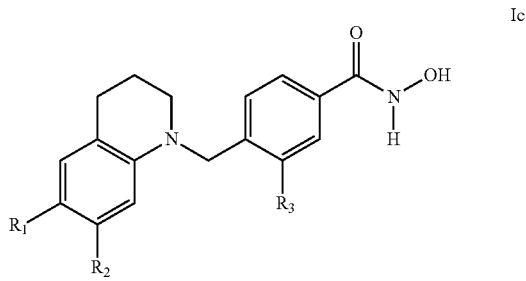

Ic wherein $R_1$ and $R_2$ are independently selected from H, Cl and F; and $R_3$ is H or F.

Additionally, salts, prodrugs, hydrates, isotopically labeled, fluorescently labeled and any other therapeutically or diagnostically relevant derivations of the present HDACIs also are included in the present invention and can be used in the methods disclosed herein. The present invention further includes all possible stereoisomers and geometric isomers of the present compounds. The present invention includes both racemic compounds and optically active isomers. When a present HDACI is desired as a single enantiomer, it can be obtained either by resolution of the final product or by stereospecific synthesis from either isomerically pure starting material or use of a chiral auxiliary reagent, for example, see Ma, Z. et al., Tetrahedron: Asymmetry, 1997, 8, 883-888. Resolution of the final product, an intermediate, or a starting material can be achieved by any suitable method known in the art. Additionally, in situations where tautomers of a present compound is possible, the present invention is intended to include all tautomeric forms of the compounds.

Prodrugs of the present compounds also are included in the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., Med. Res. Rev., 15, 83 (1995)). Specific prodrugs of HDACIs are discussed in WO 2008/055068, incorporated in its entirety herein by reference.

Compounds of the invention can exist as salts. Pharmaceutically acceptable salts of the present HDACIs often are preferred in the methods of the invention. As used herein, the term "pharmaceutically acceptable salts" refers to salts or zwitterionic forms of the present compounds. Salts of the present compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present invention appearing herein is intended to include the present compounds as well as pharmaceutically acceptable salts, hydrates, or prodrugs thereof.

The present compounds also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies, such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., Clin. Cancer Res. (2001) 7:3229).

Compounds of the present invention inhibit HDAC and are useful in the treatment of a variety of diseases and conditions. In particular, the present HDACIs are used in methods of treating a disease or condition wherein inhibition of HDAC provides a benefit, for example, cancers, neurological diseases, neurodegenerative conditions, peripheral neuropathies, autoimmune diseases, inflammatory diseases and conditions, stroke, hypertension, traumatic brain injury, autism, and malaria. The methods comprise administering a therapeutically effective amount of a present HDACI to an individual in need thereof.

The present methods also encompass administering a second therapeutic agent to the individual in addition to a present HDACI. The second therapeutic agent is selected from agents, such as drugs and adjuvants, known as useful in treating the disease or condition afflicting the individual, e.g., a chemotherapeutic agent and/or radiation known as useful in treating a particular cancer.

The present compounds have been evaluated for their activity at HDAC6 and their selectivity for HDAC6 compared to HDAC1. It previously was shown that selective HDAC6 inhibitors are implicated in a variety of disease states including, but not limited to, arthritis, autoimmune disorders, inflammatory disorders, cancer, neurological diseases such as Rett syndrome, peripheral neuropathies such as CMT, stroke, hypertension, and diseases in which oxidative stress is a causative factor or a result thereof. It also was shown that selective HDAC6 inhibitors, when administered in combination with rapamycin, prolonged the lifespan of mice with kidney xenografts. This model was used to evaluate the immunosuppressant properties of the present compounds and serve as a model of transplant rejection. Furthermore, it was previously shown that selective HDAC6 inhibitors confer neuroprotection in rat primary cortical neuron models of oxidative stress. These studies identified selective HDAC6 inhibitors as non-toxic neuroprotective agents. The present compounds behave in a similar manner because they also are selective HDAC6 agents. The present compounds demonstrate a ligand efficiency that renders them more drug-like in their physiochemical properties. In addition, the present compounds maintain the potency and selectivity observed in prior HDACIs. The present compounds therefore are pharmaceutical candidates and research tools to identify the specific functions of HDAC6.

Thus, in one embodiment, the present invention relates to a method of treating an individual suffering from a disease or condition wherein inhibition of HDAC provides a benefit comprising administering a therapeutically effective amount of a claimed HDACI compound to an individual in need thereof.

The methods of the present invention can be accomplished by administering one of the HDACI of the present invention as the neat compound or as a pharmaceutical composition. Administration of a pharmaceutical composition, or a neat HDACI of the present invention, can be performed during or after the onset of the disease or condition of interest. Typically, the pharmaceutical compositions are sterile, and contain no toxic, carcinogenic, or mutagenic compounds that would cause an adverse reaction when administered.

In some embodiments, a present HDACI may be administered in conjunction with a second therapeutic agent useful in the treatment of a disease or condition wherein inhibition of HDAC provides a benefit. The second therapeutic agent is different from the present HDACI. A present HDACI and the second therapeutic agent can be administered simultaneously or sequentially. In addition, a present HDACI and second therapeutic agent can be administered from a single composition or two separate compositions. A present HDACI and the second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of using such compounds in treating diseases or conditions wherein inhibition of HDAC provides a benefit. The present invention also is directed to pharmaceutical compositions comprising a present HDACI and an optional second therapeutic agent useful in the treatment of diseases and conditions wherein inhibition of HDAC provides a benefit. Further provided are kits comprising a present HDACI and, optionally, a second therapeutic agent useful in the treatment of diseases and conditions wherein inhibition of HDAC provides a benefit, packaged separately or together, and an insert having instructions for using these active agents.

A present HDACI and the second therapeutic agent can be administered together as a single-unit dose or separately as multi-unit doses, wherein the present HDACI is administered before the second therapeutic agent or vice versa. One or more dose of a present HDACI and/or one or more dose of the second therapeutic agent can be administered. The present HDACIs therefore can be used in conjunction with one or more second therapeutic agents, for example, but not limited to, anticancer agents.

Within the meaning of the present invention, the term "disease" or "condition" denotes disturbances and/or anomalies that as a rule are regarded as being pathological conditions or functions, and that can manifest themselves in the form of particular signs, symptoms, and/or malfunctions. As demonstrated below, a present HDACI is a potent inhibitor of HDAC and can be used in treating diseases and conditions wherein inhibition of HDAC provides a benefit, for example, cancer, a neurological disease, a neurodegenerative condition, traumatic brain injury, stroke, an inflammation, an autoimmune disease, and autism.

In one embodiment, the present invention provides methods for treating cancer, including but not limited to killing a cancer cell or neoplastic cell; inhibiting the growth of a cancer cell or neoplastic cell; inhibiting the replication of a cancer cell or neoplastic cell; or ameliorating a symptom thereof, said methods comprising administering to a subject in need thereof an amount of a present HDACI or a pharmaceutically acceptable salt thereof sufficient to treat the cancer. Additionally, it is noted that the selective HDACI may be able to facilitate the killing of cancer cells through reactivation of the immune system by mechanisms relating to the PDI receptor. A present HDACI can be used as the sole anticancer agent, or in combination with another anticancer treatment, e.g., radiation, chemotherapy, and surgery.

In another embodiment, the invention provides a method for increasing the sensitivity of a cancer cell to the cytotoxic effects of radiotherapy and/or chemotherapy comprising contacting the cell with a present HDACI or a pharmaceutically acceptable salt thereof in an amount sufficient to increase the sensitivity of the cell to the cytotoxic effects of radiotherapy and/or chemotherapy.

In a further embodiment, the present invention provides a method for treating cancer comprising: (a) administering to an individual in need thereof an amount of a present HDACI compound; and (b) administering to the individual an amount of radiotherapy, chemotherapy, or both. The amounts administered are each effective to treat cancer. In another embodiment, the amounts are together effective to treat cancer.

This combination therapy of the invention can be used accordingly in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy and/or chemotherapy or is known to be responsive to radiotherapy and/or chemotherapy. Such cancers include, but are not limited to, non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, or other CNS neoplasms.

In still another embodiment, the cancer being treated has demonstrated resistance to radiotherapy and/or chemotherapy or is known to be refractory to radiotherapy and/or chemotherapy. A cancer is refractory to a therapy when at least some significant portion of the cancer cells are not killed or their cell division is not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced or has increased.

Other cancers that can be treated with the compounds and methods of the invention include, but are not limited to, cancers and metastases, such as brain cancers (gioblastomas) and melanomas, as well as other common tumors.

In a specific embodiment, leukoplakia, a benign-appearing hyperplastic or dysplastic lesion of the epithelium, and Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)), is indicative of the desirability of prophylactic intervention.

The prophylactic use of the compounds and methods of the present invention are also indicated in some viral infections that may lead to cancer. For example, human papilloma virus can lead to cervical cancer (see, e.g., Hernandez-Avila et al., *Archives of Medical Research* (1997) 28:265-271), Epstein-Barr virus (EBV) can lead to lymphoma (see, e.g., Herrmann et al., *J Pathol* (2003) 199(2):140-5), hepatitis B or C virus can lead to liver carcinoma (see, e.g., El-Serag, *J Clin Gastroenterol* (2002) 35(5 Suppl 2):S72-8), human T cell leukemia virus (HTLV)-I can lead to T-cell leukemia (see e.g., Mortreux et al., *Leukemia* (2003) 17(1):26-38), human herpesvirus-8 infection can lead to Kaposi's sarcoma (see, e.g., Kadow et al., *Curr Opin Investig Drugs* (2002) 3(11):1574-9), and Human Immunodeficiency Virus (HIV) infection contribute to cancer development as a consequence of immunodeficiency (see, e.g., Dal Maso et al., *Lancet Oncol* (2003) 4(2):110-9).

In other embodiments, a subject exhibiting one or more of the following predisposing factors for malignancy can be treated by administration of the present HDACIs and methods of the invention: a chromosomal translocation associated with a malignancy (e.g., the Philadelphia chromosome for chronic myelogenous leukemia, t(14; 18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or procancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W.B. Saunders Co., Philadelphia, pp. 112-113) etc.), and exposure to carcinogens (e.g., smoking, and inhalation of or contacting with certain chemicals).

In another specific embodiment, the present HDACIs and methods of the invention are administered to a human subject to prevent progression of breast, colon, ovarian, or cervical cancer.

In one embodiment, the invention provides methods for treating cancer comprising (a) administering to an individual in need thereof an amount of a present HDACI; and (b) administering to the individual one or more additional anticancer treatment modality including, but not limited to, radiotherapy, chemotherapy, surgery or immunotherapy, such as a cancer vaccine. In one embodiment, the administering of step (a) is prior to the administering of step (b). In another embodiment, the administering of step (a) is subsequent to the administering of step (b). In still another embodiment, the administering of step (a) is concurrent with the administering of step (b).

In one embodiment, the additional anticancer treatment modality is radiotherapy and/or chemotherapy. In another embodiment, the additional anticancer treatment modality is surgery.

In still another embodiment, the additional anticancer treatment modality is immunotherapy, such as cancer vaccines.

In one embodiment, a present HDACI or a pharmaceutically acceptable salt thereof is administered adjunctively with the additional anticancer treatment modality.

In a preferred embodiment, the additional anticancer treatment modality is radiotherapy. In the methods of the present invention, any radiotherapy protocol can be used depending upon the type of cancer to be treated. Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present invention include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iodedeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophylla, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present HDACI, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

In an embodiment, a present HDACI or a pharmaceutically acceptable salt thereof is administered prior to the administration of radiotherapy and/or chemotherapy.

In another embodiment, a present HDACI or a pharmaceutically acceptable salt thereof is administered adjunctively with radiotherapy and/or chemotherapy.

A present HDACI and additional treatment modalities can act additively or synergistically (i.e., the combination of a present HDACI or a pharmaceutically acceptable salt thereof, and an additional anticancer treatment modality is more effective than their additive effects when each are administered alone). A synergistic combination permits the use of lower dosages of a present HDACI and/or the additional treatment modality and/or less frequent administration of a present HDACI and/or additional treatment modality to a subject with cancer. The ability to utilize lower dosages of a present HDACI and/or an additional treatment modality and/or to administer a compound of the invention and the additional treatment modality less frequently can reduce the toxicity associated with the administration without reducing the efficacy of a present HDACI and/or the additional treatment modality in the treatment of cancer. In addition, a synergistic effect can result in the improved efficacy of the treatment of cancer and/or the reduction of adverse or unwanted side effects associated with the administration of a present HDACI and/or an additional anticancer treatment modality as monotherapy.

In one embodiment, the present HDACIs may act synergistically with radiotherapy when administered in doses typically employed when such HDACIs are used alone for the treatment of cancer. In another embodiment, the present HDACIs may act synergistically with radiotherapy when administered in doses that are less than doses typically employed when such HDACIs are used as monotherapy for the treatment of cancer.

In one embodiment, radiotherapy may act synergistically with a present HDACI when administered in doses typically employed when radiotherapy is used as monotherapy for the treatment of cancer. In another embodiment, radiotherapy may act synergistically with a compound of the invention when administered in doses that are less than doses typically employed when radiotherapy is used as monotherapy for the treatment of cancer.

The effectiveness of the HDACIs as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation, and the survival of the cells monitored. Irradiated cells are plated and cultured for about 14-about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the invention.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the $TCD_{50}$ assay.

In vivo assay systems typically use transplantable solid tumor systems in experimental subjects. Radiation survival parameters for normal tissues as well as for tumors can be assayed using in vivo methods known in the art.

The present invention provides methods of treating cancers comprising the administration of an effective amount of a present HDACI in conjunction with recognized methods of surgery, radiotherapy, and chemotherapies, including, for example, chemical-based mimics of radiotherapy whereby a synergistic enhancement of the effectiveness of the recognized therapy is achieved. The effectiveness of a treatment can be measured in clinical studies or in model systems, such as a tumor model in mice, or cell culture sensitivity assays.

The present invention provides combination therapies that result in improved effectiveness and/or reduced toxicity. Accordingly, in one aspect, the invention relates to the use of the present HDACIs as radiosensitizers in conjunction with radiotherapy.

When the combination therapy of the invention comprises administering a present HDACI with one or more additional anticancer agents, the present HDACI and the additional anticancer agents can be administered concurrently or sequentially to an individual. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; anyone or a combination of the additional anticancer agents listed below may be administered.

The present invention includes methods for treating cancer comprising administering to an individual in need thereof a present HDACI and one or more additional anticancer agents or pharmaceutically acceptable salts thereof. A present HDACI and the additional anticancer agent can act additively or synergistically. Suitable anticancer agents include, but are not limited to, gemcitabine, capecitabine, methotrexate, taxol, taxotere, and the like.

Additionally, the invention provides methods of treatment of cancer using the present HDACIs as an alternative to chemotherapy alone or radiotherapy alone where the chemotherapy or the radiotherapy has proven or can prove too toxic, e.g., results in unacceptable or unbearable side effects, for the subject being treated. The individual being treated can, optionally, be treated with another anticancer treatment modality such as chemotherapy, surgery, or immunotherapy, depending on which treatment is found to be acceptable or bearable.

The present HDACIs can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a present HDACI effective to eradicate the subject's remaining bone-marrow cell population, then the stem cell graft is infused back into the subject. Supportive care then is provided while bone marrow function is restored and the subject recovers.

The present methods for treating cancer can further comprise the administration of a present HDACI and an additional therapeutic agent or pharmaceutically acceptable salts or hydrates thereof. In one embodiment, a composition comprising a present HDACI is administered concurrently with the administration of one or more additional therapeutic agent(s), which may be part of the same composition or in a different composition from that comprising the present HDACI. In another embodiment, a present HDACI is administered prior to or subsequent to administration of another therapeutic agent(s).

In the present methods for treating cancer the other therapeutic agent may be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, and tropisetron.

In an embodiment, the antiemetic agent is granisetron or ondansetron. In another embodiment, the other therapeutic agent may be an hematopoietic colony stimulating factor. Suitable hematopoietic colony stimulating factors include, but are not limited to, filgrastim, sargramostim, molgramostim, and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone, and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, and sulindac.

In still another embodiment, the other therapeutic agent may be an anxiolytic agent. Suitable anxiolytic agents include, but are not limited to, buspirene, and benzodiazepines such as diazepam, lorazepam, oxazapam, chlorazepate, clonazepam, chlordiazepoxide and alprazolam.

In addition to treating cancers and sensitizing a cancer cell to the cytotoxic effects of radiotherapy and chemotherapy, the present HDACIs are used in methods of treating diseases, conditions, and injuries to the central nervous system, such as neurological diseases, neurodegenerative disorders, and traumatic brain injuries (TBIs). In preferred embodiments, a present HDACI is capable of crossing the blood brain barrier to inhibit HDAC in the brain of the individual.

The present HDACI compounds also provide a therapeutic benefit in models of peripheral neuropathies, such as CMT. HDAC6 inhibitors have been found to cross the blood nerve barrier and rescue the phenotype observed in transgenic mice exhibiting symptoms of distal hereditary motor neuropathy. Administration of HDAC6 inhibitors to symptomatic mice increased acetylated α-tubulin levels, restored proper mitochondrial motility and axonal transport, and increased muscle re-innervation. Other peripheral neuropathies include, but are not limited to, giant axonal neuropathy and various forms of mononeuropathies, polyneuropathies, autonomic neuropathies, and neuritis.

The present HDACI compounds also ameliorate associative memory loss following Aβ elevation. In this test, mice were infused with Aβ42 via cannulas implanted into dorsal hippocampus 15 minutes prior to training. The test compounds are dosed ip (25 mg/kg) 2 hours before training. Fear learning was assessed 24 hours later.

Contextual fear conditioning performed 24 hours after training shows a reduction of freezing in Aβ-infused mice compared to vehicle-infused mice. Treatment with a present compound ameliorates deficit in freezing responses in Aβ-infused mice, and has no effect in vehicle-infused mice. A test compound alone does not affect the memory performance of the mice. In addition, treatment had no effects on motor, sensorial, or motivational skills assessed using the visible platform test in which the compounds are injected twice a day for two days. During these experiments, no signs of overt toxicity, including changes in food and liquid intake, weight loss, or changes in locomotion and exploratory behavior, are observed.

These results demonstrate that the HDACIs of the present invention are beneficial against impairment of associative memory following Aβ elevation.

The present HDACIs therefore are useful for treating a neurological disease by administration of amounts of a present HDACI effective to treat the neurological disease or by administration of a pharmaceutical composition comprising amounts of a present HDACI effective to treat the neurological disease. The neurological diseases that can be treated include, but are not limited to, Huntington's disease, lupus, schizophrenia, multiple sclerosis, muscular dystrophy, dentatorubralpallidoluysian atrophy (DRRLA), spinal and bulbar muscular atrophy (SBMA), and fine spinocerebellar ataxias (SCA1, SCA2, SCA3/MJD (Machado-Joseph Disease), SCA6, and SCAT), drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's syndrome, tremor, chorea, restless leg syndrome, Parkinson's disease, Parkinsonian syndromes, anxiety, depression, psychosis, manic depression, Friedreich's ataxia, Fragile X syndrome, spinal muscular dystrophy, Rett syndrome, Rubinstein-Taybi syndrome, Wilson's disease, multi-infarct state, CMT, GAN and other peripheral neuropathies.

In an embodiment, the neurological disease treated is Huntington's disease, Parkinson's disease, Alzheimer's disease, spinal muscular atrophy, lupus, or schizophrenia.

Charcot-Marie-Tooth disease (CMT) is one of the most common inherited neurological disorders that affects about 1 in 2,500 people in the US. CMT affects both motor and sensory nerves which may result in foot drop and a high-stepped gait with frequent tripping or falls. Mutations in the small heat-shock protein 27 (HSPB1) cause axonal CMT or distal hereditary motor neuropathy (distal HMN). Expression of mutant HSPB1 decreased acetylated α-tubulin levels and induced severe axonal transport deficits. Pharmacological inhibition of histone deacetylase 6 (HDAC6)-induced α-tubulin deacetylation caused by HDAC6i Tubastatin A corrects the axonal transport defects induced by HSPB1 mutations and rescues the CMT phenotype of symptomatic mutant HSPB1 mice. The pathogenic role of α-tubulin deacetylation has been demonstrated in mutant HSPB1-induced neuropathies and offers valuable perspectives for HDAC6 inhibitors as a therapeutic strategy for hereditary axonopathies. Compounds of the invention show potent HDAC6 isoform inhibition, high HDAC6 selectivity, impressive α-tubulin acetylation in various cell lines.

Accordingly, in another embodiment, the neurological disease is Charcot-Marie-Tooth disease.

A present HDACI also can be used with a second therapeutic agent in methods of treating conditions, diseases, and injuries to the CNS. Such second therapeutic agents are those drugs known in the art to treat a particular condition, diseases, or injury, for example, but not limited to, lithium in the treatment of mood disorders, estradiol benzoate, and nicotinamide in the treatment of Huntington's disease.

The present HDACIs also are useful in the treatment of TBIs. Traumatic brain injury (TBI) is a serious and complex injury that occurs in approximately 1.4 million people each year in the United States. TBI is associated with a broad spectrum of symptoms and disabilities, including a risk factor for developing neurodegenerative disorders, such as Alzheimer's disease.

TBI produces a number of pathologies including axonal injury, cell death, contusions, and inflammation. The inflammatory cascade is characterized by proinflammatory cytokines and activation of microglia which can exacerbate other pathologies. Although the role of inflammation in TBI is well established, no efficacious anti-inflammatory therapies are currently available for the treatment of TBI.

Several known HDAC inhibitors have been found to be protective in different cellular and animal models of acute and chronic neurodegenerative injury and disease, for example, Alzheimer's disease, ischemic stroke, multiple sclerosis (MS), Huntington's disease (HD), amyotrophic lateral sclerosis (ALS), spinal muscular atrophy (SMA), and spinal and bulbar muscular atrophy (SBMA). A recent study in experimental pediatric TBI reported a decrease in hippocampal CA3 histone H3 acetylation lasting hours to days after injury. These changes were attributed to documented upstream excitotoxic and stress cascades associated with TBI. HDACIs also have been reported to have anti-inflammatory actions acting through acetylation of non-histone proteins. The HDAC6 selective inhibitor, 4-dimethylamino-N-[5-(2-mercaptoacetylamino)pentyl]benzamide (DMA-PB), was found to be able to increase histone H3 acetylation and reduce microglia inflammatory response following traumatic brain injury in rats, which demonstrates the utility of HDACIs as therapeutics for inhibiting neuroinflammation associated with TBI.

The present HDACIs therefore also are useful in the treatment of inflammation and strokes, and in the treatment of autism and autism spectrum disorders. The present HDACIs further can be used to treat parasitic infections, (e.g., malaria, toxoplasmosis, trypanosomiasis, helminthiasis, protozoal infections (see Andrews et al. *Int. J. Parasitol.* 2000, 30(6), 761-768).

The present HDACIs also can be used as imaging agents. In particular, by providing a radiolabeled, isotopically labeled, or fluorescently-labeled HDACI, the labeled compound can image HDACs, tissues expressing HDACs, and tumors. Labeled HDACIs of the present invention also can image patients suffering from a cancer, or other HDAC-mediated diseases, e.g., stroke, by administration of an effective amount of the labeled compound or a composition containing the labeled compound. In preferred embodiments, the labeled HDACI is capable of emitting positron radiation and is suitable for use in positron emission tomography (PET). Typically, a labeled HDACI of the present invention is used to identify areas of tissues or targets that express high concentrations of HDACs. The extent of accumulation of labeled HDACI can be quantified using known methods for quantifying radioactive emissions. In addition, the labeled HDACI can contain a fluorophore or similar reporter capable of tracking the movement of particular HDAC isoforms or organelles in vitro.

The present HDACIs useful in the imaging methods contain one or more radioisotopes capable of emitting one or more forms of radiation suitable for detection by any standard radiology equipment, such as PET, SPECT, gamma cameras, MRI, and similar apparatus. Preferred isotopes including tritium ($^3$H) and carbon ($^{11}$C). Substituted HDACIs of the present invention also can contain isotopes of fluorine ($^{18}$F) and iodine ($^{123}$I) for imaging methods. Typically, a labeled HDACI of the present invention contains an alkyl group having a $^{11}$C label, i.e., a $^{11}$C-methyl group, or an alkyl group substituted with $^{18}$F, $^{123}$I, $^{125}$I, $^{131}$I, or a combination thereof.

Fluorescently-labeled HDACIs of the present invention also can be used in the imaging method of the present invention. Such compounds have an FITC, carbocyamine moiety or other fluorophore which will allow visualization of the HDAC proteins in vitro.

The labeled HDACIs and methods of use can be in vivo, and particularly on humans, and for in vitro applications, such as diagnostic and research applications, using body fluids and cell samples. Imaging methods using a labeled HDACI of the present invention are discussed in WO 03/060523, designating the U.S. and incorporated in its entirety herein. Typically, the method comprises contacting cells or tissues with a radiolabeled, isotopically labeled, fluorescently labeled, or tagged (such as biotin tagged) compound of the invention, and making a radiographic, fluorescent, or similar type of image depending on the visualization method employed, i.e., in regared to radiographic images, a sufficient amount to provide about 1 to about 30 mCi of the radiolabeled compound.

Preferred imaging methods include the use of labeled HDACIs of the present invention which are capable of generating at least a 2:1 target to background ratio of radiation intensity, or more preferably about a 5:1, about 10:1, or about 15:1 ratio of radiation intensity between target and background.

In preferred methods, the labeled HDACIs of the present invention are excreted from tissues of the body quickly to prevent prolonged exposure to the radiation of the radiolabeled compound administered to the individual. Typically, labeled HDACIs of the present invention are eliminated from the body in less than about 24 hours. More preferably, labeled HDACIs are eliminated from the body in less than about 16 hours, 12 hours, 8 hours, 6 hours, 4 hours, 2 hours, 90 minutes, or 60 minutes. Typically, preferred labeled HDACIs are eliminated in about 60 to about 120 minutes.

In addition to isotopically labeled and fluorescently labeled derivatives, the present invention also embodies the use of derivatives containing tags (such as biotin) for the identification of biomolecules associated with the HDAC isoforms of interest for diagnostic, therapeutic or research purposes.

The present HDACIs also are useful in the treatment of autoimmune diseases and inflammations. Compounds of the present invention are particularly useful in overcoming graft and transplant rejections and in treating forms of arthritis.

Despite successes of modern transplant programs, the nephrotoxicity, cardiovascular disease, diabetes, and hyperlipidemia associated with current therapeutic regimens, plus the incidence of post-transplant malignancies and graft loss from chronic rejection, drive efforts to achieve long-term allograft function in association with minimal immunosuppression. Likewise, the incidence of inflammatory bowel disease (IBD), including Crohn's disease and ulcerative colitis, is increasing. Animal studies have shown that T regulatory cells (Tregs) expressing the forkhead transcription family member, Foxp3, are key to limiting autoreactive and alloreactive immunity. Moreover, after their induction by costimulation blockade, immunosuppression, or other strategies, Tregs may be adoptively transferred to naïve hosts to achieve beneficial therapeutic effects. However, attempts to develop sufficient Tregs that maintain their suppressive functions post-transfer in clinical trials have failed. Murine studies show that HDACIs limit immune responses, at least in significant part, by increasing Treg suppressive functions, (R. Tao et al., *Nat Med,* 13, 1299-1307, (2007)), and that selective targeting of HDAC6 is especially efficacious in this regard.

With organ transplantation, rejection begins to develop in the days immediately post-transplant, such that prevention rather than treatment of rejection is a paramount consideration. The reverse applies in autoimmunity, wherein a patient presents with the disease already causing problems. Accordingly, HDAC6−/− mice treated for 14 days with low-dose RPM (rapamycin) are assessed for displaying signs of tolerance induction and resistance to the development of chronic rejection, a continuing major loss of graft function long-term in the clinical transplant population. Tolerance is assessed by testing whether mice with long-surviving allografts reject a subsequent third-party cardiac graft and accept additional donor allografts without any immunosuppression, as can occur using a non-selective HDACI plus RPM. These in vivo sutides are accompanied by assessment of ELISPOT and MLR activities using recipient lymphocytes challenged with donor cells. Protection against chronic rejection is assessed by analysis of host anti-donor humoral responses and analysis of graft transplant arteriosclerosis and interstitial fibrosis in long-surviving allograft recipients.

The importance of HDAC6 targeting is assessed in additional transplant models seeking readouts of biochemical significance, as is monitored clinically. Thus, the effects of HDAC6 in targeting in renal transplant recipients (monitoring BUN, proteinuria) and islet allografts (monitoring blood glucose levels) are assessed. Renal transplants are the most common organ transplants performed, and the kidney performs multiple functions, e.g., regulating acid/base metabolism, blood pressure, red cell production, such that efficacy in this model indicates the utility of HDAC6 targeting. Likewise, islet transplantation is a major unmet need given that clinical islet allografts are typically lost after the first one or two years post-transplant. Having a safe and non-toxic means to extend islet survival without maintenance CNI therapy would be an important advance. Transplant studies also are strengthened by use of mice with floxed HDAC6. Using existing Foxp3-Cre mice, for example, the effects of deletion of HDAC6 just in Tregs is tested. This approach can be extended to targeting of HDAC6 in T cells (CD4-Cre) and dendritic cells (CD11c-Cre), for example. Using tamoxifen-regulated Cre, the importance of HDAC6 in induction vs. maintenance of transplants (with implications for short-term vs. maintenance HDAC6I therapy) is assessed by administering tamoxifen and inducing HDAC6 deletion at varying periods post-transplant.

Studies of autoimmunity also are undertaken. In this case, interruption of existing disease is especially important and HDAC6 targeting can be efficacious without any requirement for additional therapy (in contrast to a need for brief low-dose RPM in the very aggressive, fully MHC-mismatched transplant models). Studies in mice with colitis indicated that HDAC6−/− Tregs were more effective than WT Tregs in regulating disease, and tubacin was able to rescue mice if treatment was begun once colitis had developed. These studies are extended by assessing whether deletion of HDAC6 in Tregs (Foxp3/Cre) vs. T cells (CD4=Cre) vs. DC (CD11c-Cre) differentially affect the development and severity of colitis. Similarly, control of colitis is assessed by inducing HDAC6 deletion at varying intervals after the onset of colitis with tamoxifen-regulated Cre.

The present compounds are envisioned to demonstrate anti-arthritic efficacy in a collagen-induced arthritis model in DBA1/J mice. In this test, DBA1/J mice (male, 7-8 weeks) are used, with 8 animals per group. Systemic arthritis is induced with bovine collagen type II and CFA, plus an IFA booster injection on day 21. A present HDACI is dosed at 50 mg/kg and 100 mg/kg on day 28 for 2 consecutive weeks, and the effects determined from the Average Arthritic Score vs. Days of Treatment data.

Despite efforts to avoid graft rejection through host-donor tissue type matching, in the majority of transplantation procedures, immunosuppressive therapy is critical to the viability of the donor organ in the host. A variety of immunosuppressive agents have been employed in transplantation procedures, including azathioprine, methotrexate, cyclophosphamide, FK-506, rapamycin, and corticosteroids.

The present HDACIs are potent immunosuppressive agents that suppress humoral immunity and cell-mediated immune reactions, such as allograft rejection, delayed hypersensitivity, experimental allergic encephalomyelitis, Freund's adjuvant arthritis and graft versus host disease. HDACIs of the present invention are useful for the prophylaxis of organ rejection subsequent to organ transplantation, for treatment of rheumatoid arthritis, for the treatment of psoriasis, and for the treatment of other autoimmune diseases, such as type I diabetes, Crohn's disease, and lupus.

A therapeutically effective amount of a present HDACI can be used for immunosuppression including, for example, to prevent organ rejection or graft vs. host disease, and to treat diseases and conditions, in particular, autoimmune and inflammatory diseases and conditions. Examples of autoimmune and inflammatory diseases include, but are not limited to, Hashimoto's thyroiditis, pernicious anemia, Addison's disease, psoriasis, diabetes, rheumatoid arthritis, systemic lupus erythematosus, dermatomyositis, Sjogren's syndrome, dermatomyositis, lupus erythematosus, multiple sclerosis, myasthenia gravis, Reiter's syndrome, arthritis (rheumatoid arthritis, arthritis chronic progrediente, and arthritis deformans) and rheumatic diseases, autoimmune hematological disorder (hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, psoriasis, Steven-Johnson syndrome, idiopathic sprue, autoimmune inflammatory bowel disease (ulcerative colitis and Crohn's disease) endocrine opthalmopathy, Graves disease, sarcoidosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, and glomerulonephritis.

A present HDACI can be used alone, or in conjunction with a second therapeutic agent known to be useful in the treatment of autoimmune diseases, inflammations, transplants, and grafts, such as cyclosporin, rapamycin, methotrexate, cyclophosphamide, azathioprine, corticosteroids, and similar agents known to persons skilled in the art.

Additional diseases and conditions mediated by HDACs, and particularly HDAC6, include, but are not limited to asthma, cardiac hypertrophy, giant axonal neuropathy, mononeuropathy, mononeuritis, polyneuropathy, autonomic neuropathy, neuritis in general, and neuropathy in general. These disease and conditions also can be treated by a method of the present invention.

In the present method, a therapeutically effective amount of one or more HDACI of the present invention, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present HDACI can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present HDACI is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a present HDACI that is sufficient to maintain therapeutic effects.

Toxicity and therapeutic efficacy of the present HDACI compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such procedures can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present HDACI required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present HDACI can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a present HDACI, or a composition containing the same, can be from about 1 ng/kg to about 200 mg/kg, about 1 µg/kg to about 100 mg/kg, or about 1 mg/kg to about 50 mg/kg of body weight. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A present HDACI used in a method of the present invention typically is administered in an amount of about 0.005 to about 500 milligrams per dose, about 0.05 to about 250 milligrams per dose, or about 0.5 to about 100 milligrams per dose. For example, a present HDACI can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The HDACIs of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of the present HDACIs.

The term "carrier" refers to a diluent, adjuvant, or excipient, with which a present HDACI is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a present HDACI is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a present HDACI is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present HDACI. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a present HDACI is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains an isotonic vehicle. A present HDACI can be infused with other fluids over a 10-30 minute span or over several hours.

The present HDACIs can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present HDACI to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present HDACI can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present HDACI can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present HDACI also can be formulated in rectal compositions, such as suppositories or retention enemas, e.g., containing conventional suppository bases. In addition to the formulations described previously, a present HDACI also can be formulated as a depot preparation. Such long-acting formulations can be administered by implantation (for example, subcutaneously or intramuscularly) or by intramuscular injection. Thus, for example, a present HDACI can be formulated with suitable polymeric or hydrophobic materials (for example, as an emulsion in an acceptable oil) or ion exchange resins.

In particular, a present HDACI can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present HDACIs also can be injected parenterally, for example, intravenously, intramuscularly, subcutaneously, or intracoronarily. For parenteral administration, the present HDACIs are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present HDACI and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration, for example, a syringe, drip bag, or patch. In another embodiment, the present compounds is a lyophilate. In this instance, the kit can further comprise an additional container which contains a solution useful for the reconstruction of the lyophilate.

Prior HDACIs possessed properties that hindered their development as therapeutic agents. In accordance with an important feature of the present invention, the present HDACIs were synthesized and evaluated as inhibitors for HDAC. The present compounds demonstrate an increased HDAC6 potency and selectivity against HDAC1 and HDAC8 with improvements in BEI relative to prior compounds. The improved properties of the present compounds, particularly the increase in BEI and reduced potency at HDAC8, indicate that the present compounds are useful for applications such as, but not limited to, immunosuppresssive and neuroprotective agents. For example, compounds of the present invention typically have a bonding affinity ($IC_{50}$) to HDAC6 of less than 100 μM, less than 25 μM, less than 10 μM, less than 1 μM, less than 0.5 μM, and less than 0.2 μM.

Synthetic Methods and Procedures

All starting materials and solvents were purchased from commercial suppliers at reagent purity and, unless otherwise noted, were used as obtained without any further purification. Dry solvents used as media in moisture-sensitive reactions were purchased from Sigma-Aldrich at anhydrous grade and handled under argon. All reactions were carried out in dry conditions, under inert (argon) atmosphere. Microwave reactions were run in a Biotage Initiator microwave reactor. Reactions were monitored by thin layer chromatography on silica gel-coated glass plates (TLC LuxPlate Silica gel 60 $F_{254}$, Merck), with visualization at 254 nm, and/or using appropriate dyes. Where indicated, synthetic intermediates were purified by 230-400 mesh silica gel flash chromatography on a CombiFlash system, using appropriate solvent mixtures. Final products were purified by preparative HPLC using a Shimadzu preparative liquid chromatograph [ACE 5AQ (150×21.2 mm) with 5 μm particle size. Method 1: 25-100% MeOH/$H_2O$, 30 min; 100% MeOH, 5 min; 100-25% MeOH/$H_2O$, 4 min. Method 2: 8-100% MeOH/$H_2O$, 30 min; 100% MeOH, 5 min; 100-8% MeOH/$H_2O$, 4 min. Method 3: 0% MeOH, 5 min; 0-100% MeOH/$H_2O$, 25 min; 100% MeOH, 5 min; 100-0% MeOH/$H_2O$, 4 min. Flow rate=17 mL/min], with monitoring at 254 and 280 nm. Both solvents were spiked with 0.05% TFA. $^1H$ and $^{13}C$ NMR spectra were recorded at 400 MHz and 100.6 MHz, respectively, on Bruker DPX-400 or AVANCE-400 spectrometers. Chemical shifts (δ scale) are reported in parts per million (ppm) relative to TMS. $^1H$ NMR spectra are reported in this order: multiplicity and number of protons; signals were characterized as: s (singlet), d (doublet), dd (doublet of doublets), t (triplet), m (multiplet), bs (broad signal). HRMS spectra were recorded using ESI with an LCMS-IT-TOF (Shimadzu). Purity of all final compounds was determined by analytical HPLC [ACE 3AQ C18 column (150×4.6 mm, particle size 3 μM); 0.05% TFA in H2O/0.05% TFA in MeOH gradient eluting system; flow rate=1.0 mL/min]. All compounds were tested at >95% purity as determined by HPLC analysis.

SYNTHETIC METHODS

The following synthetic schemes are representative of the reactions used to synthesize the present HDACIs. Modifications and alternate schemes to prepare HDACIs of the invention are readily within the capabilities of persons skilled in the art.

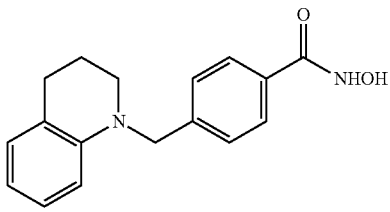

Chemical Formula: $C_{17}H_{18}N_2O_2$
Exact Mass: 282.1368
Molecular Weight: 282.3370
tPSA: 52.57
CLogP: 2.852

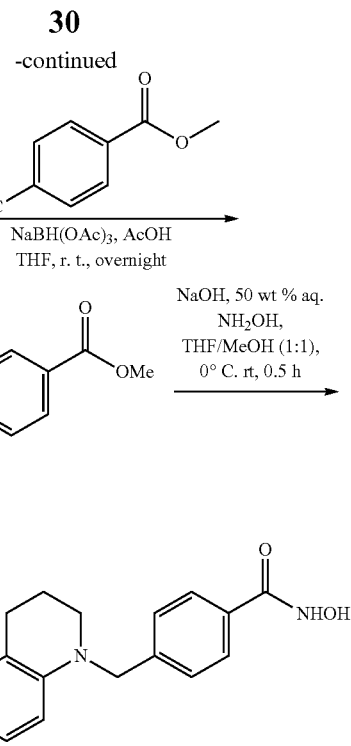

EXAMPLE 1

Synthesis of methyl 4-((3,4-dihydroquinolin-1(2H)-yl)methyl)benzoate (1-1)

A solution of 1,2,3,4-tetrahydroquinoline (126 μL, 1.00 mmol) and 4-formylbenzoic acid methyl ester (164 mg, 1.00 mmol) in toluene (5 mL) was stirred under reflux overnight. The solution was cooled to room temperature and concentrated under vacuum. The crude imine intermediate was taken up in THF (5 mL) containing AcOH (69 μL, 1.20 mmol). The solution was stirred at room temperature for 30 min, followed by the addition of NaBH(OAc)$_3$ (318 mg, 1.50 mmol). The mixture was stirred at room temperature overnight. Water was added, and the product was extracted into EtOAc (3×15 mL). The combined organic layers were washed with brine, dried over sodium sulfate, filtered, and concentrated under vacuum. The crude product was purified by flash chromatography (0-30% EtOAc/hexanes) to yield the desired compound as a light yellow oil (156 mg, 56%). $^1H$ NMR (CDCl$_3$) δ 7.98, 7.33 (AA'XX' multiplet, $J_{AX}$+ $J_{AX'}$=8.5 Hz, 4H), 7.00-6.93 (m, 2H), 6.59 (t, J=7.3 Hz, 1H), 6.41 (d, J=8.2 Hz, 1H), 4.51 (s, 2H), 3.90 (s, 3H), 3.37 (t, J=5.6 Hz, 2H), 2.83 (t, J=6.3 Hz, 2H), 2.06-1.99 (m, 2H). $^{13}C$ NMR δ 167.0, 145.3, 144.7, 130.0 (2C), 129.1, 128.8, 127.2, 126.5, 122.4, 116.2, 111.0, 55.3, 52.0, 50.1, 28.1, 22.4. ESI LRMS: [M+H]$^+$, m/z 282.1.

Synthesis of 4-((3,4-dihydroquinolin-1(2H)-yl)methyl)-N-hydroxybenzamide (Example 1)

Solid NaOH (89 mg, 2.22 mmol) was dissolved in a 50% aqueous solution of NH$_2$OH (1 mL) at 0° C. A solution of compound 1-1 (156 mg, 0.54 mmol) in 1:1 THF/MeOH (6 mL) was added dropwise to the vigorously stirred solution. Upon complete addition, the ice bath was removed, and the reaction was allowed to stir for 15 min. The mixture was then acidified to pH 5 with 2N HCl and concentrated under vacuum. The crude product was dissolved in DMF and purified by preparative HPLC to yield the desired compound as a white solid after lyophilization (90 mg, 58%). $^1$H NMR (DMSO-d$_6$) δ 11.14 (br s, 1H), 8.99 (br s, 1H), 7.70, 7.30 (AA'XX' multiplet, $J_{AX}+J_{AX'}$=8.0 Hz, 4H), 6.89 (d, J=7.3 Hz, 1H), 6.85 (t, J=8.0 Hz, 1H), 6.46 (t, J=7.3 Hz, 1H), (d, J=8.2 Hz, 1H), 4.51 (s, 2H), 3.37 (m, 2H), 2.73 (m, 2H), 1.93 (m, 2H). $^{13}$C NMR (DMSO-d$_6$) δ 164.2, 144.9, 142.5, 131.3, 128.8, 127.1 (2C), 126.9, 126.5 (2C), 121.7, 115.4, 110.6, 54.0, 49.6, 27.6, 21.8. ESI HRMS calcd. for $C_{17}H_{19}N_2O_2$: [M+H]$^+$, m/z 283.1441. Found: 283.1435.

consumption of the starting material. The reaction was stopped. Saturated aqueous NaHCO$_3$ was added to the reaction mixture and it was extracted with chloroform. The organic phase was washed with brine, dried over anhydrous Na$_2$SO$_4$, filtered and concentrated under vacuum. The crude product was recrystallized from methanol to afford the desired product as a white powder (480 mg, 70%). $^1$H NMR (400 MHz, CDCl$_3$) δ 8.00 (d, J=8.4 Hz), 7.31 (d, J=8 Hz, 2H), 6.97 (d, J=2.4 Hz, 1H), 6.90 (dd, J=8.8, 2.4 Hz, 1H), 6.33 (d, J=8.8 Hz, 1H), 4.51 (s, 2H), 3.93 (s, 3H), 3.39 (t, J=5.6 Hz, 2H), 2.82 (t, J=6.4 Hz, 2H), 2.07-2.01 (m, 2H). $^{13}$C NMR (100 MHz, CDCl$_3$) δ 166.9, 144.0, 143.8, 130.0 (2C), 129.0, 128.7, 126.8, 126.4 (2C), 124.0, 120.7, 112.0, 55.3, 52.0, 50.0, 28.0, 22.1.

Synthesis of 4-((6-chloro-3,4-dihydroquinolin-1(2H)-yl)methyl)-N-hydroxybenzamide (Example 2)

Solid NaOH (570 mg, 14.25 mmol) was solved in a cooled (0° C.) solution of hydroxylamine in water (50% wt, 3.765 mL, 57.00 mmol), then a solution of compound 2-1 (450 mg, 1.42 mmol) in THF/MeOH (21/21 mL) was added dropwise, under stirring, at 0° C. The resulting reaction mixture was allowed to warm to room temperature and stirred for 30 minutes. TLC after this time, eluting with hexanes/EtOAc, 7/3, showed complete consumption of the starting material. The reaction was stopped. Acetic acid (897 µL, 15.67 mmol) was added to the reaction mixture, then the solvents were removed by evaporation under reduced pressure. The resulting crude was treated with saturated aqueous NaHCO$_3$ (pH adjusted to ~9) and extracted with ethyl acetate. The organic phase was washed with brine, dried over anhydrous Na$_2$SO$_4$, filtered, and concentrated under vacuum to afford the desired product as a white powder (451 mg, quantitative yield). $^1$H NMR (400 MHz, DMSO-d$_6$) δ 11.16 (br s, 1H), 9.03 (br s, 1H), 7.70 (d, J=8.4 Hz, 2H), 7.28 (d, J=8.0 Hz, 2H), 6.95 (d, J=2.0 Hz, 1H), 6.87 (dd, J=8.8, 2.0, 1H), 6.37 (d, J=8.8 Hz, 1H), 4.52 (s, 2H), 3.38 (t, J=5.4, 2H), 2.73 (t, J=6.0, 2H), 1.94-1.89 (m, 2H). $^{13}$C NMR (100 MHz, DMSO-d$_6$) δ 164.4, 144.2, 142.3, 131.8, 128.6, 127.6, 126.9 (2C), 126.8 (2C), 124.3, 119.1, 112.3, 54.4, 49.9, 27.8, 21.9. ESI HRMS calcd. for $C_{17}H_{16}N_2O_2Cl$: [M–H]$^+$, m/z 315.0906. Found: 315.0897.

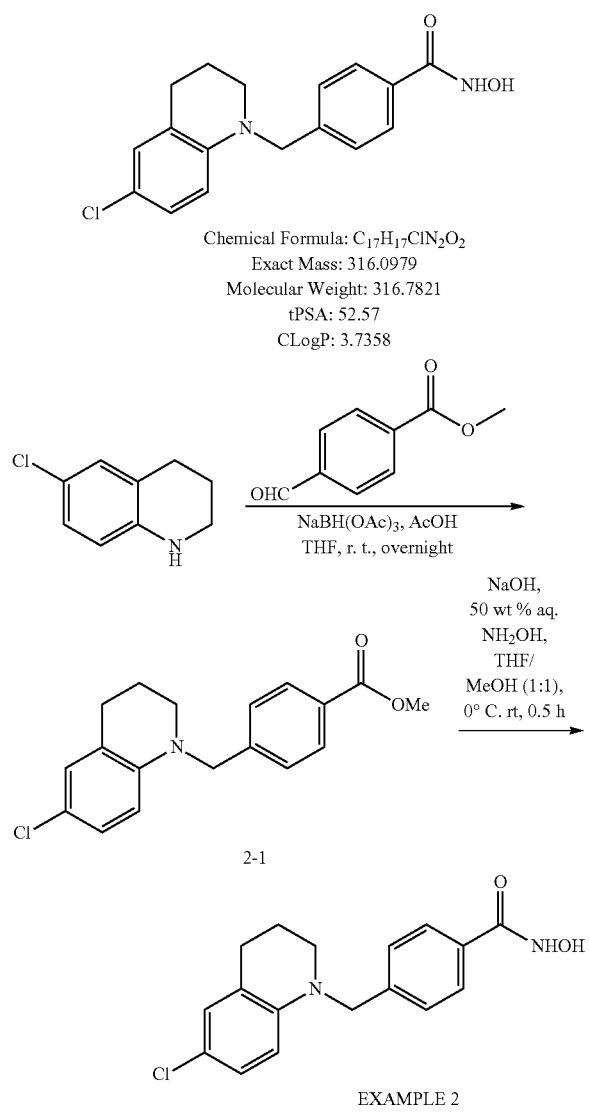

Chemical Formula: $C_{17}H_{17}ClN_2O_2$
Exact Mass: 316.0979
Molecular Weight: 316.7821
tPSA: 52.57
CLogP: 3.7358

NaBH(OAc)$_3$, AcOH
THF, r. t., overnight

NaOH,
50 wt % aq.
NH$_2$OH,
THF/
MeOH (1:1),
0° C. rt, 0.5 h 2-1

EXAMPLE 2

Synthesis of methyl 4-((6-chloro-3,4-dihydroquinolin-1(2H)-yl)methyl)benzoate (2-1)

NaBH(OAc)$_3$ (552 mg, 2.60 mmol) was added in one portion to a stirred solution of 6-chloro-1,2,3,4-tetrahydroquinoline (400 mg, 2.39 mmol) and methyl 4-formylbenzoate (356 mg, 2.17 mmol) in anhydrous DCE (11 mL). The resulting reaction mixture was stirred at room temperature overnight, under an argon atmosphere. TLC after this time, eluting with hexanes/EtOAc, 6/4, showed almost complete

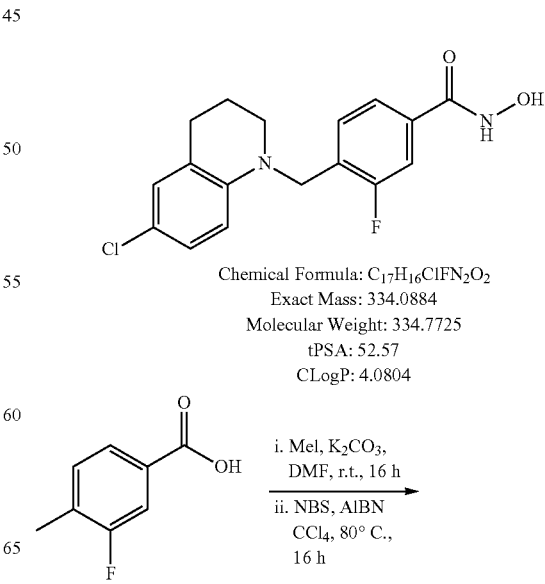

Chemical Formula: $C_{17}H_{16}ClFN_2O_2$
Exact Mass: 334.0884
Molecular Weight: 334.7725
tPSA: 52.57
CLogP: 4.0804 i. MeI, K$_2$CO$_3$,
DMF, r.t., 16 h ii. NBS, AIBN
CCl$_4$, 80° C.,
16 h

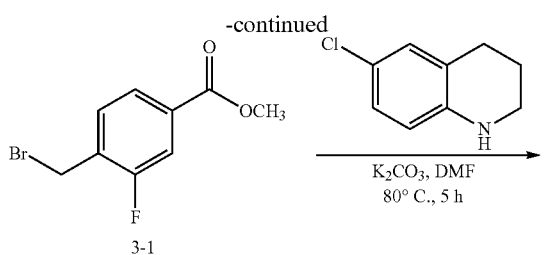

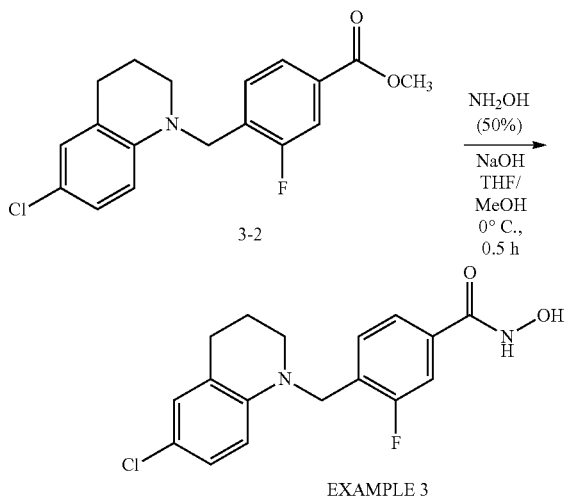

EXAMPLE 3

Synthesis of methyl 4-(bromomethyl)-3-fluorobenzoate (3-1)

To a stirred solution of 3-fluoro-4-methylbenzoic acid (308 mg, 2 mmol) in DMF (3 mL) were added $K_2CO_3$ (552 mg, 4.0 mmol) and $CH_3I$ (0.2 mL, 3.0 mmol) at room temperature. The resulting mixture was stirred at the same temperature for 5 h. Then the reaction was quenched with water (15 mL) extracted with EtOAc (3×15 mL). The combined organic extracts were washed with brine (20 mL), dried over sodium sulfate, and concentrated under vacuum. The crude product was used directly into next step (220 mg, 1.3 mmol, 65%). The methyl ester intermediate was dissolved in $CCl_4$ (5 mL). To the solution were added NBS (278 mg, 1.56 mmol) and AIBN (21 mg, 0.13 mmol). The resulting mixture was heated at 80° C. overnight. Then the reaction was quenched with water (15 mL) extracted with DCM (3×15 mL). The combined organic extracts were washed with brine (20 mL), dried over sodium sulfate, and concentrated under vacuum. The crude product was purified by flash chromatography (0-50% EtOAc/hexanes) to afford as colorless solid (200 mg, 62%). $^1$H NMR (400 MHz, $CDCl_3$) δ 7.81 (dd, J=8.0, 1.3 Hz, 1H), 7.72 (dd, J=10.2, 1.3 Hz, 1H), 7.47 (t, J=7.7 Hz, 1H), 4.52 (s, 2H), 3.99-3.78 (m, 3H). $^{13}$C NMR (100 MHz, $CDCl_3$) δ 165.5 (d, J=2.7 Hz), 161.5, 159.0, 132.4 (d, J=7.7 Hz), 131.2 (d, J=3.0 Hz), 130.1 (d, J=14.7 Hz), 125.6 (d, J=3.6 Hz), 117.0, 116.8, 52.5, 24.6 (d, J=4.2 Hz).

Synthesis of methyl 4-((6-chloro-3,4-dihydroquinolin-1(2H)-yl)methyl)-3-fluorobenzoate (3-2)

To a round bottom flask charged with compound 3-1 (120 mg, 0.5 mmol) and 6-chloro-1,2,3,4-tetrahydroquinoline (55 mg, 0.32 mmol) in DMF (3 mL) was added $K_2CO_3$ (88 mg, 0.64 mmol). The resulting mixture was allowed to stir for 5 h at 80° C. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-80% EtOAc/hexanes) to afford as colorless oil (50 mg, 30%). $^1$H NMR (400 MHz, $CDCl_3$) δ 7.77-7.68 (m, 2H), 7.24 (dd, J=10.9, 4.5 Hz, 1H), 6.95 (d, J=2.5 Hz, 1H), 6.89 (dd, J=8.7, 2.5 Hz, 1H), 6.28 (d, J=8.7 Hz, 1H), 4.52 (s, 2H), 3.91 (s, 3H), 3.45-3.28 (m, 2H), 2.79 (t, J=6.3 Hz, 2H), 2.08-1.95 (m, 2H). $^{13}$C NMR (100 MHz, $CDCl_3$) δ 165.9 (d, J=2.8 Hz), 160.5 (d, J=244.9 Hz), 143.6, 130.8 (d, J=7.0 Hz), 130.7 (d, J=14.4 Hz), 128.7, 128.0 (d, J=4.5 Hz), 126.9, 125.5 (d, J=3.3 Hz), 124.1, 120.9, 116.5 (d, J=23.1 Hz), 111.8, 52.3, 50.1, 49.5 (d, J=4.3 Hz), 28.0, 22.2.

Synthesis of 4-((6-chloro-3,4-dihydroquinolin-1(2H)-yl)methyl)-3-fluoro-N-hydroxybenzamide (Example 3)

In a round bottom flask, NaOH (48 mg, 1.2 mmol) was dissolved in 50% aqueous $NH_2OH$ (0.5 mL, approx. 50 equiv) at 0° C. A solution of compound 3-2 (50 mg, 0.15 mmol) in 1:1 THF/MeOH (2 mL) was added dropwise, and stirring was continued for 30 min while warming to room temperature. The solution was neutralized with 6N HCl and extracted with EtOAc (3×10 mL). The organic layers were separated, washed with brine, dried over $Na_2SO_4$, concentrated under vacuum. The crude product was purified by flash chromatography (0-20% MeOH/DCM) and lyophilized to afford the desired product as pink powder (30 mg, 60%). $^1$H NMR (400 MHz, DMSO-$d_6$) δ 11.26 (br s, 1H), 9.11 (br s, 1H), 7.53 (t, J=9.3 Hz, 2H), 7.22 (t, J=7.8 Hz, 1H), 6.96 (d, J=2.3 Hz, 1H), 6.90 (dd, J=8.8, 2.5 Hz, 1H), 6.38 (d, J=8.7 Hz, 1H), 4.55 (s, 2H), 3.40-3.35 (m, 2H, overlap with water peak), 2.74 (t, J=6.3 Hz, 2H), 1.97-1.87 (m, 2H). $^{13}$C NMR (100 MHz, DMSO-$d_6$) δ 162.7, 160.0 (d, J=243 Hz), 143.5, 133.5 (d, J=6.7 Hz), 128.3 (d, J=4.8 Hz), 129.3, 128.2, 126.4, 124.1, 122.9 (d, J=1.1 Hz), 119.0, 113.9 (d, J=23.1 Hz), 111.8, 49.29, 48.3 (d, J=3.4 Hz), 27.3, 21.4. ESI HRMS calc. for $C_{17}H_{17}ClFN_2O_2$: [M+H]$^+$, m/z 335.0957; found: 335.0965.

EXAMPLE 4

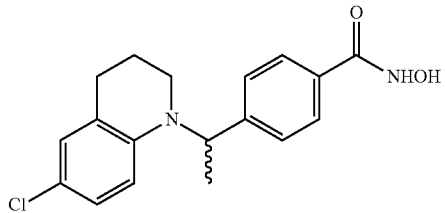

Chemical Formula $C_{18}H_{19}ClN_2O_2$
Exact Mass: 330.1135
Molecular Weight: 330.8087
tPSA: 52.57
CLogP: 4.0448

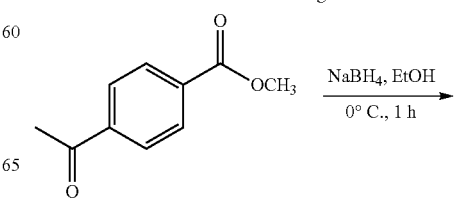

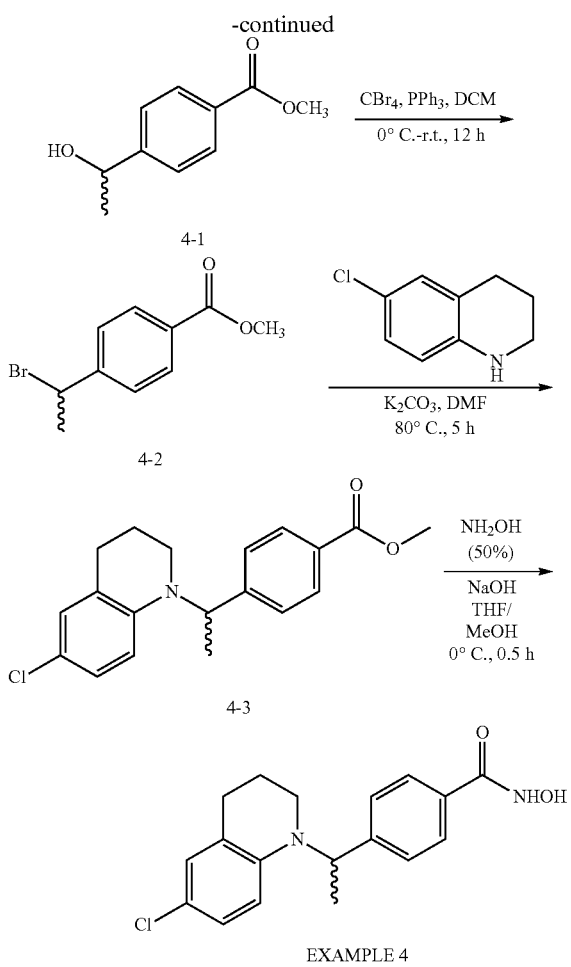

EXAMPLE 4

Synthesis of methyl 4-(1-hydroxyethyl)benzoate (4-1)

To a stirred solution of methyl 4-acetylbenzoate (358 mg, 2.0 mmol) in EtOH (10 mL) was added NaBH$_4$ (152 mg, 4 mmol) at 0° C. The resulting mixture was stirred at same temperature for 1 h. The excess solvent was removed under vacuum. And the residue was quenched with H$_2$O, and extracted with EtOAc (3×20 mL). The combined organic extracts were washed with brine (40 mL), dried over sodium sulfate, and concentrated under vacuum. The crude product was obtained as colorless oil (310 mg, 86%) and used directly into next step. $^1$H NMR (400 MHz, CDCl$_3$) δ 8.07-7.96 (m, 2H), 7.44 (d, J=8.2 Hz, 2H), 5.04-4.87 (m, 1H), 3.91 (s, 3H), 1.50 (d, J=6.5 Hz, 3H). $^{13}$C NMR (100 MHz, CDCl$_3$) δ 167.0, 150.9, 129.9 (2C), 129.2, 125.3 (2C), 70.0, 52.1, 25.3.

Synthesis of methyl 4-(1-bromoethyl)benzoate (4-2)

To a stirred solution of compound 4-1 (310 mg, 1.72 mmol) in DCM (20 mL) were added CBr$_4$ (855 mg, 2.52 mmol) and PPh$_3$ (660 mg, 2.52 mmol) at 0° C. Then the resulting mixture was stirred at room temperature overnight. The reaction was quenched with water (10 mL), extracted with DCM (3×20 mL). The combined organic extracts were washed with brine (30 mL), dried over sodium sulfate, and concentrated under vacuum. The crude product was purified by flash chromatography (0-20% EtOAc/hexanes), and the desired compound was obtained as colorless oil (260 mg, 62%). $^1$H NMR (400 MHz, CDCl$_3$) δ 8.01 (d, J=8.4 Hz, 2H), 7.50 (d, J=8.2 Hz, 2H), 5.20 (q, J=6.9 Hz, 1H), 3.92 (s, 3H), 2.05 (d, J=6.9 Hz, 3H). $^{13}$C NMR (100 MHz, CDCl$_3$) δ 166.5, 148.0, 130.0 (2C), 126.9 (2C), 52.2, 48.0, 26.6.

Synthesis of methyl 4-(1-(6-chloro-3,4-dihydroquinolin-1(2H)-yl)ethyl)benzoate (4-3)

To a round bottom flask charged with compound 4-3 (260 mg, 1.07 mmol) and 6-chloro-1,2,3,4-tetrahydroquinoline (121 mg, 0.71 mmol) in DMF (3 mL) was added K$_2$CO$_3$ (196 mg, 1.42 mmol). The resulting mixture was allowed to stir overnight at 80° C. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-80% EtOAc/hexanes) to afford as colorless oil (60 mg, 17%). $^1$H NMR (400 MHz, CDCl$_3$) δ 7.99 (d, J=8.4 Hz, 2H), 7.37 (d, J=8.2 Hz, 2H), 6.96-6.88 (m, 2H), 6.51 (d, J=8.5 Hz, 1H), 5.11-5.00 (m, 1H), 3.90 (s, 3H), 3.20-3.10 (m, 1H), 3.06-2.96 (m, 1H), 2.74 (dd, J=9.3, 4.8 Hz, 2H), 1.92-1.78 (m, 2H), 1.59 (d, J=7.0 Hz, 3H). $^{13}$C NMR (100 MHz, CDCl$_3$) δ 166.9, 148.0, 143.9, 129.9 (2C), 128.9 (2C), 126.8 (2C), 126.7, 124.7, 120.4, 111.9, 55.3, 52.1, 42.9, 28.3, 22.0, 16.2.

Synthesis of 4-(1-(6-chloro-3,4-dihydroquinolin-1(2H)-yl)ethyl)-N-hydroxybenzamide (Example 4)

In a round bottom flask, NaOH (58 mg, 1.46 mmol) was dissolved in 50% aqueous NH$_2$OH (0.5 mL, approx. 50 equiv) at 0° C. A solution of compound 4-3 (60 mg, 0.18 mmol) in 1:1 THF/MeOH (10 mL) was added dropwise, and stirring was continued for 30 min while warming to room temperature. The solution was neutralized with 6N HCl and extracted with EtOAc (3×15 mL). The organic layers were separated, washed with brine, dried over Na$_2$SO$_4$, concentrated under vacuum. The crude product was purified by flash chromatography (0-20% MeOH/DCM) and lyophilized to afford the desired product as pink powder (40 mg, 67%). $^1$H NMR (400 MHz, DMSO-d$_6$) δ 11.15 (br s, 1H), 8.99 (br s, 1H), 7.71 (d, J=8.2 Hz, 2H), 7.35 (d, J=8.3 Hz, 2H), 6.96-6.84 (m, 2H), 6.59 (d, J=8.9 Hz, 1H), 5.09 (q, J=6.9 Hz, 1H), 3.32-3.18 (m, 1H), 3.10-3.00 (m, 1H), 2.69 (t, J=6.2 Hz, 2H), 1.90-1.71 (m, 2H), 1.52 (d, J=6.9 Hz, 3H). $^{13}$C NMR (100 MHz, DMSO-d$_6$) δ 164.1, 145.9, 143.9, 131.3 128.2 (2C), 127.1, 126.6 (2C), 126.3, 124.5, 118.5, 112.2, 54.7, 42.5, 27.7, 21.4, 16.9. ESI HRMS calc. for C$_{18}$H$_{20}$ClN$_2$O$_2$: [M+H]$^+$, m/z 331.1208; found: 331.1189.

EXAMPLE 5

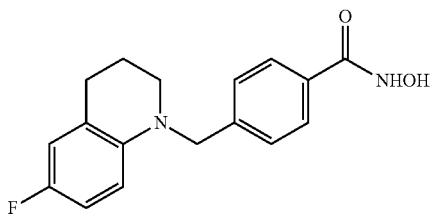

Chemical Formula C$_{17}$H$_{17}$FN$_2$O$_2$
Exact Mass: 300.1274
Molecular Weight: 300.3275
tPSA: 52.57
CLogP: 3.1658

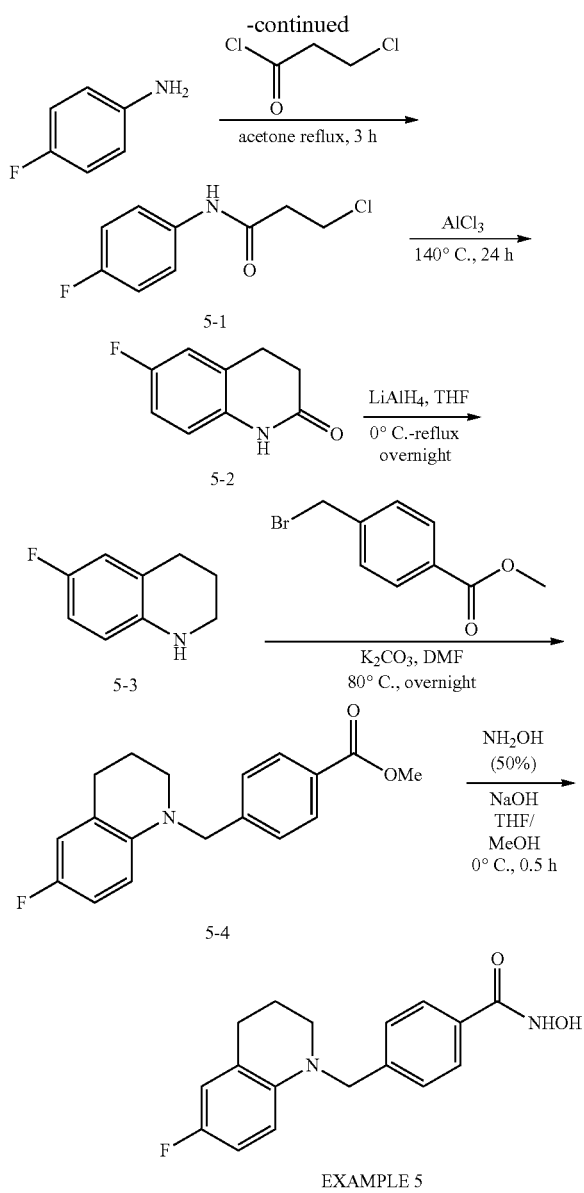

EXAMPLE 5

Synthesis of 3-chloro-N-(4-fluorophenyl)propanamide (5-1)

To a round bottom flask charged with 4-fluoroaniline (1.0 g, 9.0 mmol) and in acetone (10 mL) was added 3-chloropropanoyl chloride (0.44 mL, 4.5 mmol). The resulting mixture was allowed to stir for 3 h at 56° C. The mixture was cooled to room temperature and quenched with 2N HCl (10 mL), and then extracted with EtOAc (3×15 mL). The combined organic extracts were washed with brine (20 mL), dried over sodium sulfate, and concentrated under vacuum. The crude product was afforded (1.0 g, 55%) as grey solid, and used directly into next step. $^1$H NMR (400 MHz, CDCl$_3$) δ 7.80 (s, 1H), 7.51-7.35 (m, 2H), 6.99 (t, J=8.6 Hz, 2H), 3.85 (t, J=6.3 Hz, 2H), 2.79 (t, J=6.3 Hz, 2H); $^{13}$C NMR (100 MHz, CDCl$_3$) δ 168.2, 159.7 (d, J=242.6 Hz), 133.5 (d, J=2.6 Hz), 122.4 (d, J=7.9 Hz, 2C), 115.7 (d, J=22.4 Hz, 2C), 40.3, 40.0.

Synthesis of 6-fluoro-3,4-dihydroquinolin-2(1H)-one (5-2)

In a three-necked flask charged with compound 5-1 (1.0 g, 5.0 mmol) under Ar atmosphere was added AlCl$_3$ (1.34 g, 10.0 mmol) at 140° C. The resulting mixture was stirring at the same temperature for 24 h. Then the reaction was quenched with 1 N HCl carefully at 0° C., and then extracted with EtOAc (3×30 mL). The combined organic extracts were washed with brine (20 mL), dried over sodium sulfate, and concentrated under vacuum. The crude product was purified by flash chromatography (0-80% EtOAc/hexanes) to afford as off-white powder (540 mg, 67%). $^1$H NMR (400 MHz, CDCl$_3$) δ 9.52 (br s, 1H), 6.93-6.72 (m, 3H), 2.95 (t, J=7.5 Hz, 2H), 2.62 (t, J=7.5 Hz, 2H); $^{13}$C NMR (100 MHz, CDCl$_3$) δ 172.2, 158.8 (d, J=240.5 Hz), 133.6 (d, J=2.5 Hz), 125.5 (d, J=7.6 Hz), 116.7 (d, J=8.1 Hz), 114.9 (d, J=23.0 Hz), 114.6 (d, J=22.7 Hz), 30.4, 25.5.

Synthesis of 6-fluoro-1,2,3,4-tetrahydroquinoline (5-3)

To a stirred solution of compound 5-3 (540 mg, 3.30 mmol) in THF (20 mL) were added LiAlH$_4$ (373 mg, 9.90 mmol) at 0° C. The resulting mixture was stirred at same temperature for 30 min, heated at reflux overnight. The reaction was quenched with water (0.40 mL), 5 N NaOH (0.40 mL), and water (2.0 mL). The afforded participate was filtered off, and the filtrate was concentrated under vacuum. The crude product was purified by flash chromatography (0-10% EtOAc/hexanes), and the title compound was obtained as colorless solid (400 mg, 82%). $^1$H NMR (400 MHz, CDCl$_3$) δ 6.76-6.60 (m, 2H), 6.40 (dd, J=9.5, 4.8 Hz, 1H), 3.53 (br s, 1H), 3.33-3.19 (m, 2H), 2.75 (t, J=6.4 Hz, 2H), 2.02-1.83 (m, 2H). $^{13}$C NMR (100 MHz, CDCl$_3$) δ 156.6 (d, J=233.1 Hz), 141.1 (d, J=1.7 Hz), 122.9 (d, J=6.6 Hz), 115.7 (d, J=21.5 Hz), 115.0 (d, J=7.6 Hz), 113.3 (d, J=22.3 Hz), 42.2, 27.2, 22.1.

Synthesis of methyl 4-((6-fluoro-3,4-dihydroquinolin-1(2H)-yl)methyl)benzoate (5-4)

To a round bottom flask charged with compound 5-3 (400 mg, 2.70 mmol) and methyl 4-(bromomethyl)benzoate (924 mg, 4.05 mmol) in DMF (10 mL) was added K$_2$CO$_3$ (745 mg, 5.40 mmol) and KI (45 mg, 0.27 mmol). The resulting mixture was allowed to stir overnight at 80° C. The mixture was cooled to room temperature and after addition of water (20 mL) extracted with EtOAc (3×25 mL). The combined organic extracts were washed with brine (30 mL), dried over sodium sulfate, and concentrated under vacuum. The crude product was purified by flash chromatography (0-10% EtOAc/hexanes) to afford as yellow solid (500 mg, 62%). $^1$H NMR (400 MHz, CDCl$_3$) δ 8.00 (d, J=8.2 Hz, 2H), 7.33 (d, J=8.2 Hz, 2H), 6.73 (dd, J=9.0, 3.0 Hz, 1H), 6.65 (td, J=8.6, 3.0 Hz, 1H), 6.31 (dd, J=8.9, 4.6 Hz, 1H), 4.47 (s, 2H), 3.91 (s, 3H), 3.34 (t, J=5.6 Hz, 2H), 2.81 (t, J=6.3 Hz, 2H), 2.08-1.97 (m, 2H). $^{13}$C NMR (100 MHz, CDCl$_3$) δ 167.1, 155.0 (d, J=233.5 Hz), 144.7, 141.9 (d, J=1.6 Hz), 130.1 (2C), 129.0, 126.6 (2C), 124.0 (d, J=6.6 Hz), 115.7 (d, J=21.7 Hz), 113.3 (d, J=21.6 Hz), 111.8 (d, J=7.4 Hz), 56.0, 52.2, 50.3, 28.3, 22.4.

Synthesis of 4-((6-fluoro-3,4-dihydroquinolin-1(2H)-yl)methyl)-N-hydroxybenzamide (Example 5)

In a round bottom flask, NaOH (536 mg, 13.4 mmol) was dissolved in 50% aqueous NH$_2$OH (5.0 mL, approx. 50 equiv) at 0° C. A solution of SS-3-39 (500 mg, 1.67 mmol) in 1:1 THF/MeOH (20 mL) was added dropwise, and stirring was continued for 30 min while warming to room temperature. The solution was neutralized with 2N HCl and extracted with EtOAc (3×20 mL). The organic layers were separated, washed with brine, dried over Na$_2$SO$_4$, concentrated under vacuum. The crude product was purified by flash chromatography (0-10% MeOH/DCM) and lyophilized to afford the desired product as light pink powder (390 mg, 78%). $^1$H NMR (400 MHz, DMSO-d$_6$) δ 11.16 (br s, 1H), 9.00 (br s, 1H), 7.70 (d, J=8.1 Hz, 2H), 7.30 (d, J=8.1 Hz, 2H), 6.77 (dd, J=9.3, 2.9 Hz, 1H), 6.69 (td, J=8.7, 3.0 Hz, 1H), 6.35 (dd, J=9.0, 4.7 Hz, 1H), 4.48 (s, 2H), 3.33 (t, J=5.5 Hz, 2H), 2.74 (t, J=6.2 Hz, 2H), 1.95-1.85 (m, 2H). $^{13}$C NMR (100 MHz, DMSO-d$_6$) δ 164.2, 153.9 (d, J=233.5 Hz), 142.4, 141.6 (d, J=1.2 Hz), 131.3, 127.2 (2C), 126.6 (3C), 123.5 (d, J=6.6 Hz), 115.2 (d, J=21.5 Hz), 112.8 (d, J=21.4 Hz), 111.3 (d, J=7.4 Hz), 54.4, 49.6, 27.6, 21.7. ESI HRMS calc. for C$_{17}$H$_{17}$FN$_2$O$_2$: [M+H]$^+$, m/z 301.1347; found: 301.1335.

EXAMPLE 6

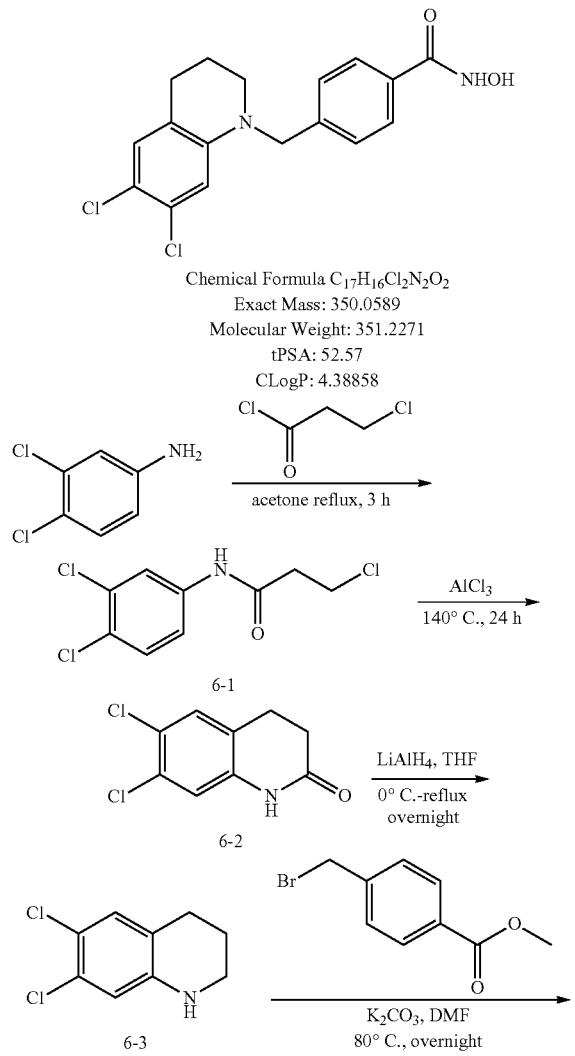

Chemical Formula C$_{17}$H$_{16}$Cl$_2$N$_2$O$_2$
Exact Mass: 350.0589
Molecular Weight: 351.2271
tPSA: 52.57
CLogP: 4.38858

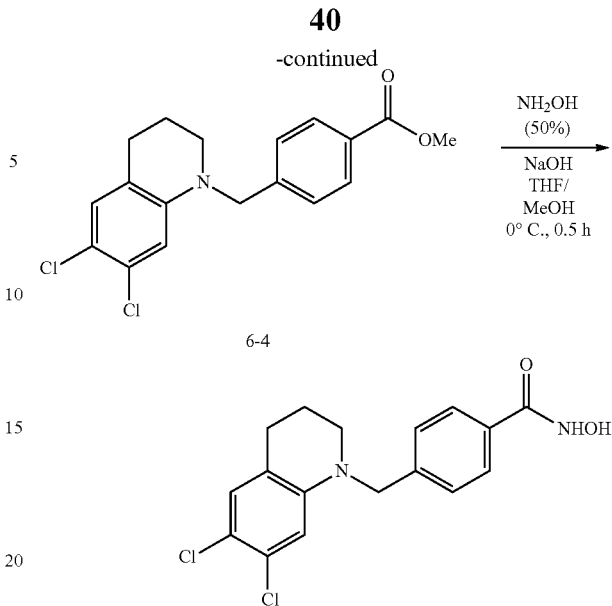

EXAMPLE 6

Synthesis of 3-chloro-N-(3,4-dichlorophenyl)propanamide (6-1)

To a round bottom flask charged with 3,4-dichloroaniline (1.26 g, 7.87 mmol) and in acetone (10 mL) was added 3-chloropropanoyl chloride (0.38 mL, 3.94 mmol). The resulting mixture was allowed to stir for 3 h at 56° C. The mixture was cooled to room temperature and quenched with 2N HCl (10 mL), and then extracted with EtOAc (3×15 mL). The combined organic extracts were washed with brine (20 mL), dried over sodium sulfate, and concentrated under vacuum. The crude product was afforded as off-white solid (1.08 g, 54%), and used directly into next step. $^1$H NMR (400 MHz, CDCl$_3$) δ 7.75 (d, J=2.0 Hz, 1H), 7.59 (br s, 1H), 7.37 (d, J=8.7 Hz, 1H), 7.33 (dd, J=8.7, 2.2 Hz, 1H), 3.87 (t, J=6.3 Hz, 2H), 2.82 (t, J=6.3 Hz, 2H). $^{13}$C NMR (100 MHz, CDCl$_3$) δ 168.0, 136.8, 132.9, 130.6, 128.0, 121.9, 119.3, 40.4, 39.6.

Synthesis of 6,7-dichloro-3,4-dihydroquinolin-2(1H)-one (6-2)

In a three-necked flask charged with compound 6-1 (510 mg, 2.0 mmol) under Ar atmosphere was added AlCl$_3$ (532 mg, 4.0 mmol) at 140° C. The resulting mixture was stirring at the same temperature for 24 h. Then the reaction was quenched with 1 N HCl carefully at 0° C., and then extracted with EtOAc (3×15 mL). The combined organic extracts were washed with brine (20 mL), dried over sodium sulfate, and concentrated under vacuum. The crude product was purified by flash chromatography (0-80% EtOAc/hexanes) to afford as off-white powder (400 mg, 94%, crude isomer 2:1).

Synthesis of 6,7-dichloro-1,2,3,4-tetrahydroquinoline (6-3)

To a stirred solution of compound 6-2 (400 mg, 1.87 mmol) in THF (20 mL) were added LiAlH$_4$ (224 mg, 5.84 mmol) at 0° C. The resulting mixture was stirred at same temperature for 30 min, heated at reflux overnight. The reaction was quenched with water (0.25 mL), 5 N NaOH (0.25 mL), and water (1.25 mL). The afforded participate was filtered off, and the filtrate was concentrated under vacuum. The crude product was purified by flash chromatography (0-10% EtOAc/hexanes), and the title compound was obtained as off-white powder (90 mg, 24%). $^1$H NMR (400 MHz, CDCl$_3$) δ 6.97 (s, 1H), 6.52 (s, 1H), 3.89 (brs, 1H), 3.31-3.22 (m, 2H), 2.68 (t, J=6.4 Hz, 2H), 1.93-1.84 (m, 2H). $^{13}$C NMR (100 MHz, CDCl$_3$) δ 144.2, 130.4, 129.6, 121.4, 118.6, 114.7, 41.5, 26.4, 21.4.

Synthesis of methyl 4-((6,7-dichloro-3,4-dihydro-quinolin-1(2H)-yl)methyl)benzoate (6-4)

To a round bottom flask charged with compound 6-3 (90 mg, 0.45 mmol) and methyl 4-(bromomethyl)benzoate (154 mg, 0.68 mmol) in DMF (3 mL) was added K$_2$CO$_3$ (124 mg, 0.90 mmol). The resulting mixture was allowed to stir overnight at 80° C. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-10% EtOAc/hexanes) to afford as colorless oil (70 mg, 44%, crude). $^1$H NMR (400 MHz, CDCl$_3$) δ 8.01 (d, J=8.4 Hz, 2H), 7.29 (d, J=8.5 Hz, 2H), 7.01 (s, 1H), 6.45 (s, 1H), 4.48 (s, 2H), 3.92 (s, 3H), 3.36 (t, J=5.7 Hz, 2H), 2.75 (t, J=6.3 Hz, 2H), 2.07-1.94 (m, 2H).

Synthesis of 4-((6,7-dichloro-3,4-dihydroquinolin-1 (2H)-yl)methyl)-N-hydroxybenzamide (Example 6)

In a round bottom flask, NaOH (64 mg, 1.6 mmol) was dissolved in 50% aqueous NH$_2$OH (0.5 mL, approx. 50 equiv) at 0° C. A solution of compound 6-4 (70 mg, 0.2 mmol) in 1:1 THF/MeOH (4 mL) was added dropwise, and stirring was continued for 30 min while warming to room temperature. The solution was neutralized with 2N HCl and extracted with EtOAc (3×15 mL). The organic layers were separated, washed with brine, dried over Na$_2$SO$_4$, concentrated under vacuum. The crude product was purified by flash chromatography (0-10% MeOH/DCM) and lyophilized to afford the desired product as pink powder (20 mg, 29%). $^1$H NMR (400 MHz, CDCl$_3$) δ 7.66 (s, 2H), 7.24 (d, J=5.0 Hz, 2H), 6.99 (s, 1H), 6.38 (s, 1H), 4.41 (s, 2H), 3.31 (t, J=5.4 Hz, 2H), 2.73 (t, J=6.0 Hz, 2H), 2.00-1.93 (m, 2H). $^{13}$C NMR (100 MHz, CDCl$_3$) δ 170.1, 158.8, 138.5, 128.6, 128.2, 128.0, 127.8, 127.7 (2C), 127.2, 116.8, 114.2 (2C), 55.3, 45.5, 31.6, 25.4. ESI HRMS calc. for C$_{17}$H$_{17}$C$_{12}$N$_2$O$_2$: [M+H]$^+$, m/z 351.0662; found: 351.0647.

EXAMPLE 7

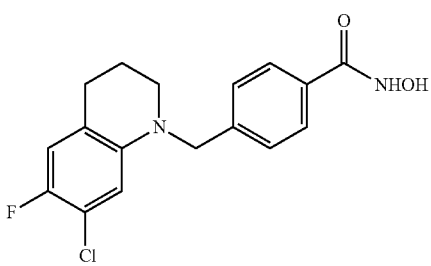

Chemical Formula C$_{17}$H$_{16}$ClFN$_2$O$_2$
Exact Mass: 334.0884
Molecular Weight: 334.7725
tPSA: 52.57
CLogP: 3.93858

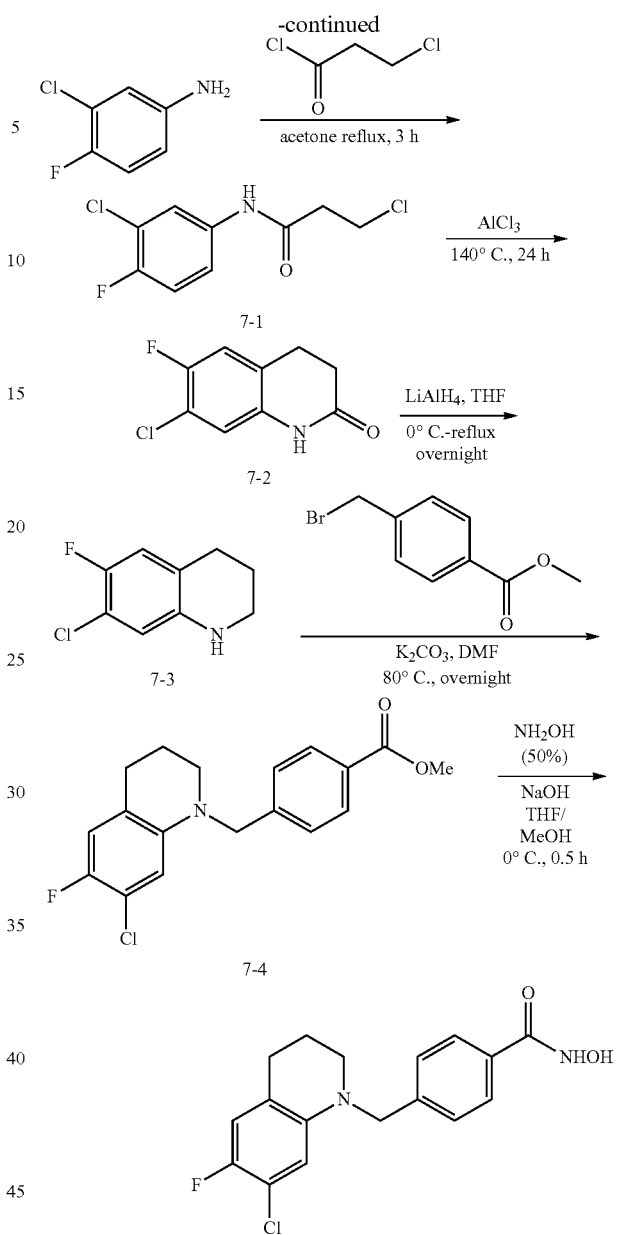

EXAMPLE 7

Synthesis of 3-chloro-N-(3-chloro-4-fluorophenyl) propanamide (7-1)

To a round bottom flask charged with 3-chloro-4-fluoroaniline (1.45 g, 10.0 mmol) and in acetone (20 mL) was added 3-chloropropanoyl chloride (0.35 mL, 5.0 mmol). The resulting mixture was allowed to stir for 3 h at 56° C. The mixture was cooled to room temperature and quenched with 2N HCl (20 mL), and then extracted with EtOAc (3×20 mL). The combined organic extracts were washed with brine (20 mL), dried over sodium sulfate, and concentrated under vacuum. The crude product was purified by flash chromatography (0-80% EtOAc/hexanes), and the title compound was obtained as off-white powder (1.22 g, 54%). $^1$H NMR (400 MHz, CDCl$_3$) δ 7.72 (br s, 1H), 7.67 (dd, J=6.5, 2.5 Hz, 1H), 7.34-7.29 (m, 1H), 7.06 (t, J=8.7 Hz, 1H), 3.86 (t, J=6.3

Hz, 2H), 2.80 (t, J=6.3 Hz, 2H). $^{13}$C NMR (100 MHz, CDCl$_3$) δ 168.3, 155.2 (d, J=245 Hz), 134.0 (d, J=3.3 Hz), 122.8, 121.3 (d, J=18.5 Hz), 120.2 (d, J=6.8 Hz), 116.8 (d, J=22.0 Hz), 40.4, 39.8.

Synthesis of 7-chloro-6-fluoro-3,4-dihydroquinolin-2(1H)-one (7-2)

In a three-necked flask charged with compound 7-1 (1.22 g, 5.35 mmol) under Ar atmosphere was added AlCl$_3$ (1.42 g, 10.7 mmol) at 140° C. The resulting mixture was stirring at the same temperature for 24 h. Then the reaction was quenched with 1 N HCl carefully at 0° C., and then extracted with EtOAc (3×15 mL). The combined organic extracts were washed with brine (20 mL), dried over sodium sulfate, and concentrated under vacuum. The crude product was purified by flash chromatography (0-80% EtOAc/hexanes) to afford as off-white powder (570 mg, 54%, crude isomer 2:1).

Synthesis of 7-chloro-6-fluoro-1,2,3,4-tetrahydroquinoline (7-3)

To a stirred solution of compound 7-2 (570 mg, 2.86 mmol) in THF (20 mL) were added LiAlH$_4$ (326 mg, 8.60 mmol) at 0° C. The resulting mixture was stirred at same temperature for 30 min, heated at reflux overnight. The reaction was quenched with water (0.35 mL), 5 N NaOH (0.35 mL), and water (1.75 mL). The afforded participate was filtered off, and the filtrate was concentrated under vacuum. The crude product was purified by flash chromatography (0-10% EtOAc/hexanes), and the title compound was obtained as white powder (160 mg, 30%). $^1$H NMR (400 MHz, CDCl$_3$) δ 6.72 (d, J=9.5 Hz, 1H), 6.45 (d, J=6.4 Hz, 1H), 3.74 (br, 1H), 3.33-3.18 (m, 2H), 2.70 (t, J=6.4 Hz, 2H), 1.98-1.83 (m, 2H). $^{13}$C NMR (101 MHz, CDCl$_3$) δ 150.5 (d, J=236 Hz), 141.6 (d, J=2.1 Hz), 121.3 (d, J=5.7 Hz), 118.1 (d, J=18.5 Hz), 116.9 (d, J=21.1 Hz), 114.8, 41.9, 26.8, 21.8.

Synthesis of methyl 4-((7-chloro-6-fluoro-3,4-dihydroquinolin-1(2H)-yl)methyl)benzoate (7-4)

To a round bottom flask charged with compound 7-3 (160 mg, 0.86 mmol) and methyl 4-(bromomethyl)benzoate (296 mg, 1.30 mmol) in DMF (5 mL) was added K$_2$CO$_3$ (237 mg, 1.72 mmol) and KI (14 mg, 0.09 mmol). The resulting mixture was allowed to stir overnight at 80° C. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-10% EtOAc/hexanes) and the title compound was obtained as colorless oil (210 mg, 30%). $^1$H NMR (400 MHz, CDCl$_3$) δ 8.00 (d, J=8.2 Hz, 2H), 7.30 (d, J=8.1 Hz, 2H), 6.77 (d, J=9.2 Hz, 1H), 6.35 (d, J=6.3 Hz, 1H), 4.45 (s, 2H), 3.91 (s, 3H), 3.32 (t, J=6.3 Hz, 2H), 2.76 (t, J=6.3 Hz, 2H), 2.03-1.97 (m, 2H).

Synthesis of 4-((7-chloro-6-fluoro-3,4-dihydroquinolin-1(2H)-yl)methyl)-N-hydroxybenzamide (Example 7)

In a round bottom flask, NaOH (200 mg, 5.0 mmol) was dissolved in 50% aqueous NH$_2$OH (2.0 mL, approx. 50 equiv) at 0° C. A solution of compound 7-4 (210 mg, 0.63 mmol) in 1:1 THF/MeOH (6 mL) was added dropwise, and stirring was continued for 30 min while warming to room temperature. The solution was neutralized with 2N HCl and extracted with EtOAc (3×15 mL). The organic layers were separated, washed with brine, dried over Na$_2$SO$_4$, concentrated under vacuum. The crude product was purified by flash chromatography (0-10% MeOH/DCM) and lyophilized to afford the desired product as off-white powder (150 mg, 71%). $^1$H NMR (400 MHz, DMSO-d$_6$) δ 11.15 (br s, 1H), 8.99 (br s, 1H), 7.71 (d, J=8.1 Hz, 2H), 7.29 (d, J=8.2 Hz, 2H), 6.99 (d, J=9.7 Hz, 1H), 6.43 (d, J=6.4 Hz, 1H), 4.52 (s, 2H), 3.36 (t, J=5.6 Hz, 2H, overlap with water peak), 2.73 (t, J=6.1 Hz, 2H), 1.95-1.82 (m, 2H). $^{13}$C NMR (100 MHz, DMSO-d$_6$) δ 164.1, 148.5 (d, J=233 Hz), 142.3 (d, J=1.5 Hz), 141.7, 131.5, 127.2 (2C), 126.5 (2C), 122.6 (d, J=5.7 Hz), 116.7 (d, J=8.2 Hz), 116.4 (d, J=5.0 Hz), 110.7, 54.1, 49.2, 27.1, 21.3. ESI HRMS calc. for C$_{17}$H$_{17}$ClFN$_2$O$_2$: [M+H]$^+$, m/z 335.0957; found: 335.0945.

EXAMPLE 8

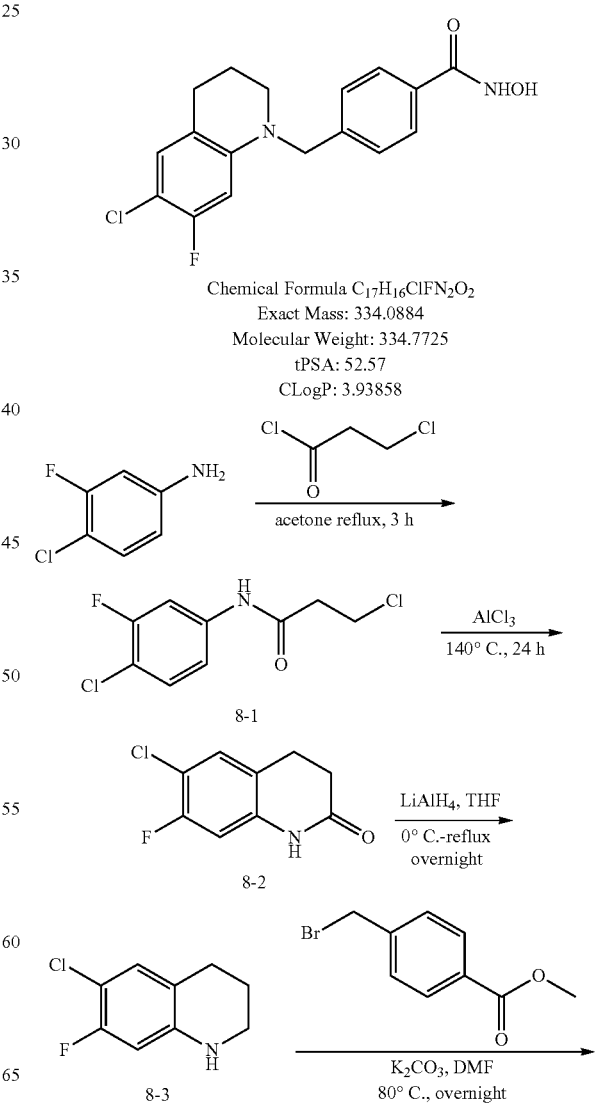

Chemical Formula C$_{17}$H$_{16}$ClFN$_2$O$_2$
Exact Mass: 334.0884
Molecular Weight: 334.7725
tPSA: 52.57
CLogP: 3.93858

-continued

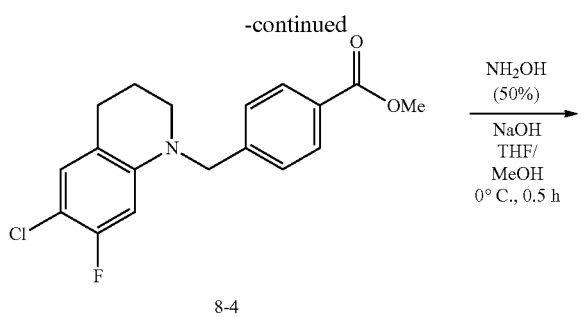

8-4

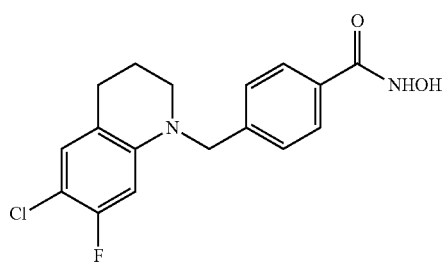

EXAMPLE 8

Synthesis of 3-chloro-N-(4-chloro-3-fluorophenyl)propanamide (8-1)

To a round bottom flask charged with 4-chloro-3-fluoroaniline (1.45 g, 10.0 mmol) and in acetone (20 mL) was added 3-chloropropanoyl chloride (0.35 mL, 5.0 mmol). The resulting mixture was allowed to stir for 3 h at 56° C. The mixture was cooled to room temperature and quenched with 2N HCl (20 mL), and then extracted with EtOAc (3×20 mL). The combined organic extracts were washed with brine (20 mL), dried over sodium sulfate, and concentrated under vacuum. The crude product was purified by flash chromatography (0-80% EtOAc/hexanes), and the title compound was obtained as off-white powder (1.20 g, 53%). $^1$H NMR (400 MHz, CDCl$_3$) δ 7.71 (s, 1H), 7.59 (dd, J=10.8, 2.2 Hz, 1H), 7.30 (t, J=8.4 Hz, 1H), 7.15-7.09 (m, 1H), 3.86 (t, J=6.3 Hz, 2H), 2.81 (t, J=6.3 Hz, 2H).

Synthesis of 6-chloro-7-fluoro-3,4-dihydroquinolin-2(1H)-one (8-2)

In a three-necked flask charged with compound 8-1 (1.20 g, 5.26 mmol) under Ar atmosphere was added AlCl$_3$ (1.40 g, 10.5 mmol) at 140° C. The resulting mixture was stirring at the same temperature for 24 h. Then the reaction was quenched with 1 N HCl carefully at 0° C., and then extracted with EtOAc (3×15 mL). The combined organic extracts were washed with brine (20 mL), dried over sodium sulfate, and concentrated under vacuum. The crude product was purified by flash chromatography (0-80% EtOAc/hexanes) to afford as off-white powder (610 mg, 58%, crude isomer 2:1).

Synthesis of 6-chloro-7-fluoro-1,2,3,4-tetrahydroquinoline (8-3)

To a stirred solution of compound 8-2 (610 mg, 3.07 mmol) in THF (20 mL) were added LiAlH$_4$ (350 mg, 9.20 mmol) at 0° C. The resulting mixture was stirred at same temperature for 30 min, heated at reflux overnight. The reaction was quenched with water (0.35 mL), 5 N NaOH (0.35 mL), and water (1.75 mL). The afforded participate was filtered off, and the filtrate was concentrated under vacuum. The crude product was purified by flash chromatography (0-10% EtOAc/hexane), and the title compound was obtained as white powder (110 mg, 19%). $^1$H NMR (400 MHz, CDCl$_3$) δ 6.90 (d, J=8.1 Hz, 1H), 6.22 (d, J=10.9 Hz, 1H), 3.91 (s, 1H), 3.35-3.14 (m, 2H), 2.68 (t, J=6.2 Hz, 2H), 1.93-1.75 (m, 2H). $^{13}$C NMR (100 MHz, CDCl$_3$) δ 156.9 (d, J=241 Hz), 144.5 (d, J=9.6 Hz), 130.3, 118.0 (d, J=2.9 Hz), 106.7 (d, J=17.8 Hz), 101.3 (d, J=23.8 Hz), 41.6, 26.3, 21.6.

Synthesis of methyl 4-((6-chloro-7-fluoro-3,4-dihydroquinolin-1(2H)-yl)methyl)benzoate (8-4)

To a round bottom flask charged with compound 8-3 (110 mg, 0.59 mmol) and methyl 4-(bromomethyl)benzoate (203 mg, 0.89 mmol) in DMF (5 mL) was added K$_2$CO$_3$ (163 mg, 1.18 mmol) and KI (10 mg, 0.06 mmol). The resulting mixture was allowed to stir overnight at 80° C. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-10% EtOAc/hexanes) and the title compound was obtained as colorless oil (150 mg, 76%). $^1$H NMR (400 MHz, CDCl$_3$) δ 8.00 (d, J=8.4 Hz, 2H), 7.28 (d, J=8.6 Hz, 2H), 6.93 (d, J=8.4 Hz, 1H), 6.16 (d, J=12.3 Hz, 1H), 4.46 (s, 2H), 3.91 (s, 3H), 3.41-3.31 (m, 2H), 2.74 (t, J=6.2 Hz, 2H), 2.05-1.96 (m, 2H).

Synthesis of 4-((6-chloro-7-fluoro-3,4-dihydroquinolin-1(2H)-yl)methyl)-N-hydroxybenzamide (Example 8)

In a round bottom flask, NaOH (144 mg, 3.6 mmol) was dissolved in 50% aqueous NH$_2$OH (1.5 mL, approx. 50 equiv) at 0° C. A solution of compound 8-4 (150 mg, 0.45 mmol) in 1:1 THF/MeOH (6 mL) was added dropwise, and stirring was continued for 30 min while warming to room temperature. The solution was neutralized with 2N HCl and extracted with EtOAc (3×15 mL). The organic layers were separated, washed with brine, dried over Na$_2$SO$_4$, concentrated under vacuum. The crude product was purified by flash chromatography (0-10% MeOH/DCM), prep-HPLC (method 2), and lyophilized to afford the desired product as off-white powder (75 mg, 50%). $^1$H NMR (400 MHz, DMSO-d$_6$) δ 11.14 (br s, 1H), 7.70 (d, J=8.2 Hz, 2H), 7.29 (d, J=8.2 Hz, 2H), 7.04 (d, J=8.7 Hz, 1H), 6.37 (d, J=13.2 Hz, 1H), 4.54 (s, 2H), 3.37 (t, J=6.1 Hz, 2H, overlap with water peak), 2.70 (t, J=6.1 Hz, 2H), 1.99-1.81 (m, 2H). $^{13}$C NMR (100 MHz, DMSO-d$_6$) δ 164.1, 156.5 (d, J=238 Hz), 145.1 (d, J=9.9 Hz), 141.4, 131.5, 129.4, 127.2 (2C), 126.5 (2C), 119.4 (d, J=2.7 Hz), 103.6 (d, J=17.9 Hz), 98.5 (d, J=25.4 Hz), 53.8, 49.1, 26.6, 21.2. ESI HRMS calc. for C$_{17}$H$_{17}$ClFN$_2$O$_2$: [M+H]$^+$, m/z; 335.0957, found: 335.0942.

EXAMPLE 9

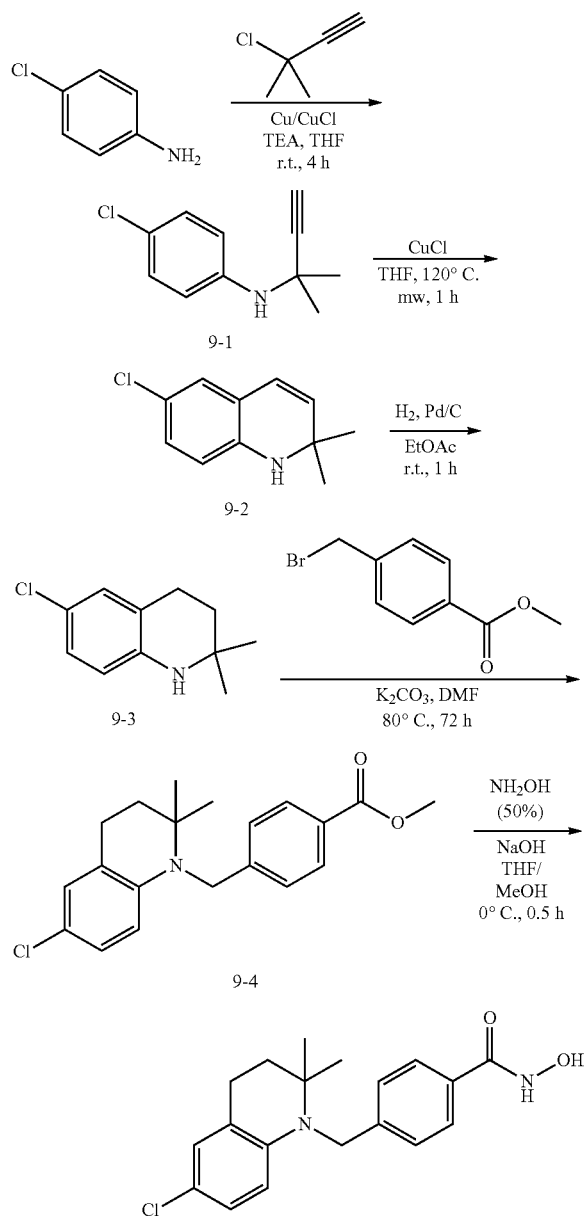

EXAMPLE 9

Synthesis of 4-chloro-N-(2-methylbut-3-yn-2-yl)aniline (9-1)

To a round bottom flask charged with 4-chloroaniline (635 mg, 5.0 mmol) and TEA (0.9 mL, 6.1 mmol) in $Et_2O/H_2O$ (5/1 mL) were Cu (3.2 mg, 0.05 mmol), CuCl (4.9 mg, 0.05 mmol), and 3-chloro-3-methylbut-1-yne (410 mg, 4.15 mmol) under Ar atmosphere at room temperature. The resulting mixture was allowed to stir for 3 h at room temperature. The reaction was quenched with $H_2O$ (5 mL), and then extracted with EtOAc (3×10 mL). The combined organic extracts were washed with brine (20 mL), dried over sodium sulfate, and concentrated under vacuum. The crude product was purified by flash chromatography (0-30% EtOAc/hexanes), and the title compound was obtained as yellow oil (540 mg, 56%). $^1$H NMR (400 MHz, $CDCl_3$) δ 7.18-7.10 (m, 2H), 6.91-6.83 (m, 2H), 3.66 (s, 1H), 2.38 (s, 1H), 1.60 (s, 6H). $^{13}$C NMR (100 MHz, $CDCl_3$) δ 144.2, 128.8 (2C), 123.8 (2C), 117.9, 87.5, 70.9, 48.3, 30.5 (2C).

Synthesis of 6-chloro-2,2-dimethyl-1,2-dihydroquinoline (9-2)

To a solution of compound 9-1 (540 mg, 2.8 mmol) in THF (5 mL) were added CuCl (28 mg, 0.28 mmol) in a microwave reaction tube. The mixture was heated at 120° C. for 1 h in a microwave reactor. After completion of the reaction, precipitate solid was filtered off and the filtrate was concentrated under reduced pressure. The crude product was purified by flash chromatography (0-10% EtOAc/hexanes), and the title compound was obtained as yellow solid (420 mg, 78%). $^1$H NMR (400 MHz, $CDCl_3$) δ 6.89 (dd, J=8.4, 2.4 Hz, 1H), 6.85 (d, J=2.3 Hz, 1H), 6.33 (d, J=8.4 Hz, 1H), 6.19 (d, J=9.7 Hz, 1H), 5.51 (d, J=9.7 Hz, 1H), 3.63 (brs, 1H), 1.30 (s, 6H). $^{13}$C NMR (100 MHz, $CDCl_3$) δ 141.7, 132.3, 128.2, 126.2, 122.9, 121.7, 121.5, 113.9, 52.5, 31.2 (2C).

Synthesis of 6-chloro-2,2-dimethyl-1,2,3,4-tetrahydroquinoline (9-3)

To a solution of compound 9-2 (420 mg, 2.17 mmol) in EtOAc (10 mL) was added Pd/C (10%, 50 mg), then the reaction was degassed under vacuum and exchanged with $H_2$ atmosphere. The resulting mixture was stirred at room temperature for 30 min. Then the precipitate solid was filtered off and the filtrate was concentrated under vacuum. The crude product (360 mg, 85%) was used directly into next step. $^1$H NMR (400 MHz, $CDCl_3$) δ 6.96 (d, J=2.4 Hz, 1H), 6.90 (dd, J=8.5, 2.4 Hz, 1H), 6.37 (d, J=8.5 Hz, 1H), 2.74 (t, J=6.7 Hz, 2H), 1.67 (t, J=6.8 Hz, 2H), 1.20 (s, 6H). $^{13}$C NMR (100 MHz, $CDCl_3$) δ 142.6, 129.0, 126.7, 121.8, 121.2, 115.4, 49.1, 34.1, 29.2, 24.2 (2C).

Synthesis of methyl 4-((6-chloro-2,2-dimethyl-3,4-dihydroquinolin-1(2H)-yl)methyl)benzoate (9-4)

To a round bottom flask charged with compound 9-3 (360 mg, 1.85 mmol) and methyl 4-(bromomethyl)benzoate (624 mg, 2.77 mmol) in DMF (10 mL) was added $K_2CO_3$ (510 mg, 3.70 mmol), KI (30 mg, 0.19 mmol). The resulting mixture was allowed to stir at 80° C. for 72 h. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-10% EtOAc/hexanes), and the title compound was obtained as yellow solid (70 mg, 10%). $^1$H NMR (400 MHz, CDCl$_3$) δ 7.98 (d, J=8.3 Hz, 2H), 7.33 (d, J=8.3 Hz, 2H), 6.98 (d, J=2.5 Hz, 1H), 6.83 (dd, J=8.8, 2.6 Hz, 1H), 6.12 (d, J=8.9 Hz, 1H), 4.49 (s, 2H), 3.90 (s, 3H), 2.84 (t, J=6.6 Hz, 2H), 1.92 (t, J=6.6 Hz, 2H), 1.25 (s, 6H). $^{13}$C NMR (100 MHz, CDCl$_3$) δ 167.1, 146.0, 144.1, 130.1 (2C), 128.9, 128.5, 126.8, 126.1 (2C), 123.9, 120.9, 113.7, 54.5, 52.2, 49.6, 36.7, 26.6 (2C), 24.7.

Synthesis of 4-((6-chloro-2,2-dimethyl-3,4-dihydroquinolin-1(2H)-yl)methyl)-N-hydroxybenzamide (Example 9)

In a round bottom flask, NaOH (64 mg, 1.6 mmol) was dissolved in 50% aqueous NH$_2$OH (0.5 mL, approx. 50 equiv) at 0° C. A solution of compound 9-4 (70 mg, 0.2 mmol) in 1:1 THF/MeOH (4 mL) was added dropwise, and stirring was continued for 30 min while warming to room temperature. The solution was neutralized with 2N HCl and extracted with EtOAc (3×15 mL). The organic layers were separated, washed with brine, dried over Na$_2$SO$_4$, concentrated under vacuum. The crude product was purified by flash chromatography (0-10% MeOH/DCM), prep-HPLC and lyophilized to afford the desired product as off-white powder (20 mg, 29%). $^1$H NMR (400 MHz, DMSO-d$_6$) δ 11.12 (s, 1H), 7.68 (d, J=8.3 Hz, 2H), 7.31 (d, J=8.5 Hz, 2H), 6.98 (d, J=2.4 Hz, 1H), 6.83 (dd, J=8.7, 2.6 Hz, 1H), 6.09 (d, J=9.0 Hz, 1H), 4.50 (s, 2H), 2.78 (t, J=6.5 Hz, 2H), 1.86 (t, J=6.5 Hz, 2H), 1.21 (s, 6H). $^{13}$C NMR (100 MHz, DMSO-d$_6$) δ 164.3, 143.9, 143.7, 131.1, 127.8, 127.1 (2C), 126.2, 125.9 (2C), 124.1, 119.0, 113.4, 54.1, 48.4, 35.9, 26.1 (2C), 23.9. ESI HRMS calc. for C$_{19}$H$_{21}$ClN$_2$O$_2$: [M−H]$^+$, m/z 343.1219; found: 343.1220.

EXAMPLE 10

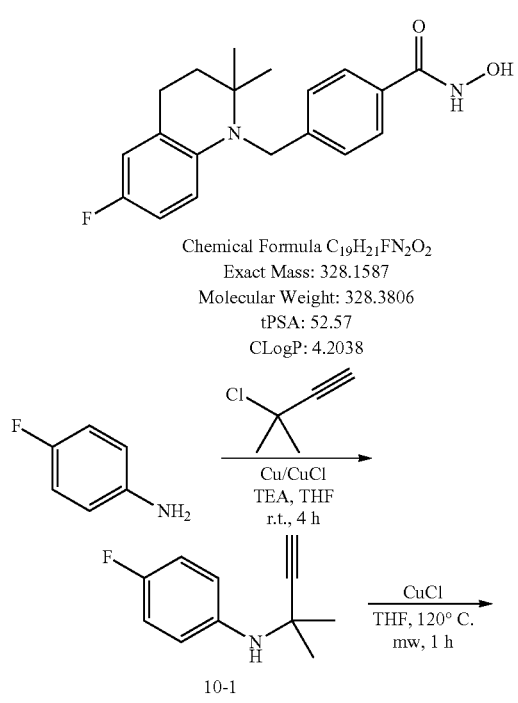

Chemical Formula C$_{19}$H$_{21}$FN$_2$O$_2$
Exact Mass: 328.1587
Molecular Weight: 328.3806
tPSA: 52.57
CLogP: 4.2038

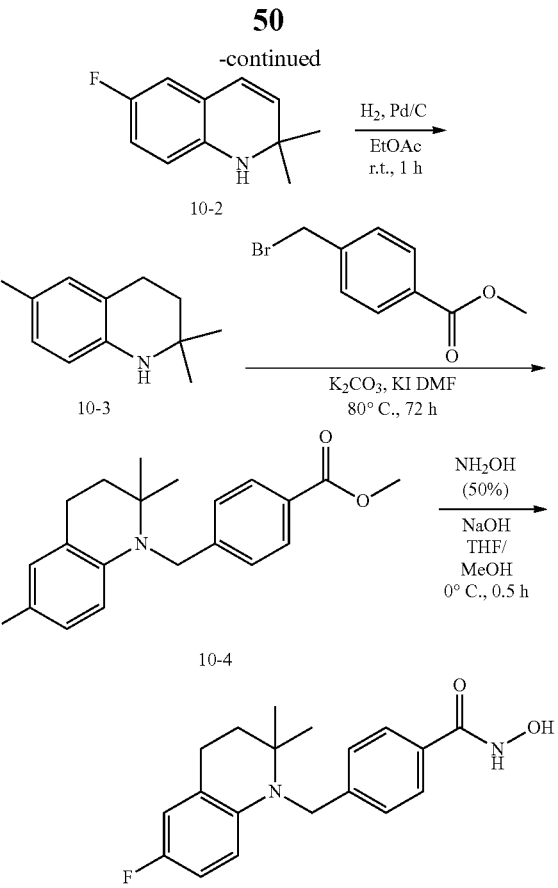

EXAMPLE 10

Synthesis of 4-fluoro-N-(2-methylbut-3-yn-2-yl) aniline (10-1)

To a round bottom flask charged with 4-fluoroaniline (1.11 g, 10.0 mmol) and TEA (1.57 mL, 11.2 mmol) in Et$_2$O/H$_2$O (20/5 mL) were Cu (6.4 mg, 0.10 mmol), CuCl (9.8 mg, 0.10 mmol), and 3-chloro-3-methylbut-1-yne (847 mg, 8.30 mmol) under Ar atmosphere at room temperature. The resulting mixture was allowed to stir for 3 h at room temperature. The reaction was quenched with H$_2$O (10 mL), and then extracted with EtOAc (3×15 mL). The combined organic extracts were washed with brine (20 mL), dried over sodium sulfate, and concentrated under vacuum. The crude product was purified by flash chromatography (0-15% EtOAc/hexanes), and the title compound was obtained as yellow oil (1.10 g, 62%). $^1$H NMR (400 MHz, CDCl$_3$) δ 6.96-6.93 (m, 2H), 6.92 (d, J=1.5 Hz, 2H), 3.44 (br s, 1H), 2.37 (s, 1H), 1.57 (s, 6H). $^{13}$C NMR (100 MHz, CDCl$_3$) δ 157.3 (d, J=236 Hz), 141.7 (d, J=2.2 Hz), 119.4 (d, J=7.5 Hz, 2C), 115.3 (d, J=22 Hz, 2C), 88.0, 70.8, 48.9, 30.4 (2C).

Synthesis of 6-fluoro-2,2-dimethyl-1,2-dihydroquinoline (10-2)

To a solution of compound 10-1 (1.1 g, 6.2 mmol) in THF (10 mL) were added CuCl (61 mg, 0.62 mmol) in a microwave reaction tube. The mixture was heated at 120° C. for 1 h in a microwave reactor. After completion of the reaction, precipitate solid was filtered off and the filtrate was concentrated under reduced pressure. The crude product was purified by flash chromatography (0-10% EtOAc/hexanes), and the title compound was obtained as yellow oil (700 mg, 64%). $^1$H NMR (400 MHz, CDCl$_3$) δ 6.68 (td, J=8.6, 2.9 Hz, 1H), 6.63 (dd, J=8.9, 2.8 Hz, 1H), 6.34 (dd, J=8.5, 4.5 Hz, 1H), 6.21 (d, J=9.7 Hz, 1H), 5.55 (d, J=9.7 Hz, 1H), 3.54 (br s, 1H), 1.30 (s, 6H). $^{13}$C NMR (100 MHz, CDCl$_3$) δ 155.8 (d, J=232 Hz), 139.4 (d, J=1.5 Hz), 132.8, 123.2 (d, J=2.2 Hz), 121.2 (d, J=7.6 Hz), 114.7 (d, J=22.6 Hz), 113.4 (d, J=7.5 Hz), 112.8 (d, J=22.6 Hz), 52.3, 30.7 (2C).

Synthesis of 6-fluoro-2,2-dimethyl-1,2,3,4-tetrahydroquinoline (10-3)

To a solution of compound 10-4 (700 mg, 3.95 mmol) in EtOAc (10 mL) was added Pd/C (10%, 70 mg), then the reaction was degassed under vacuum and exchanged with H$_2$ atmosphere. The resulting mixture was stirred at room temperature for 45 min. Then the precipitate solid was filtered off and the filtrate was concentrated under reduced pressure. The crude product (650 mg, 93%) was used directly into next step. $^1$H NMR (400 MHz, CDCl$_3$) δ 6.70 (ddd, J=16.9, 8.7, 2.8 Hz, 2H), 6.38 (dd, J=8.6, 4.8 Hz, 1H), 3.23 (br s, 1H), 2.76 (t, J=6.7 Hz, 2H), 1.68 (t, J=6.8 Hz, 2H), 1.20 (s, 6H). $^{13}$C NMR (100 MHz, CDCl$_3$) δ 155.5 (d, J=233 Hz), 140.24 (d, J=1.5 Hz), 121.5 (d, J=6.6 Hz), 115.5 (d, J=21.6 Hz), 115.2 (d, J=7.4 Hz), 113.4 (d, J=22.4 Hz), 49.0, 34.1, 29.1 (2C), 24.5.

Synthesis of methyl 4-((6-fluoro-2,2-dimethyl-3,4-dihydroquinolin-1(2H)-yl)methyl)benzoate (10-4)

To a round bottom flask charged with compound 10-3 (650 mg, 3.63 mmol) and methyl 4-(bromomethyl)benzoate (1241 mg, 5.45 mmol) in DMF (20 mL) was added K$_2$CO$_3$ (1001 mg, 7.26 mmol), KI (60 mg, 0.36 mmol). The resulting mixture was allowed to stir at 80° C. for 72 h. The mixture was cooled to room temperature and after addition of water (30 mL) extracted with EtOAc (3×30 mL). The combined organic extracts were washed with brine (30 mL), dried over sodium sulfate, and concentrated under vacuum. The crude product was purified by flash chromatography (0-10% EtOAc/hexanes), and the title compound was obtained as yellow oil (570 mg, 38%). $^1$H NMR (400 MHz, CDCl$_3$) δ 7.99 (d, J=8.4 Hz, 2H), 7.36 (d, J=8.5 Hz, 2H), 6.74 (dd, J=9.0, 3.0 Hz, 1H), 6.60 (td, J=8.9, 3.0 Hz, 1H), 6.11 (dd, J=9.0, 4.6 Hz, 1H), 4.47 (s, 2H), 3.91 (s, 3H), 2.85 (t, J=6.6 Hz, 2H), 1.93 (t, J=6.6 Hz, 2H), 1.25 (s, 6H).

Synthesis of 4-((6-fluoro-2,2-dimethyl-3,4-dihydroquinolin-1(2H)-yl)methyl)-N-hydroxybenzamide (Example 10)

In a round bottom flask, NaOH (446 mg, 11.2 mmol) was dissolved in 50% aqueous NH$_2$OH (4.5 mL, approx. 50 equiv) at 0° C. A solution of compound 10-4 (570 mg (80% crude), 1.40 mmol) in 1:1 THF/MeOH (10 mL) was added dropwise, and stirring was continued for 30 min while warming to room temperature. The solution was neutralized with 2N HCl and extracted with EtOAc (3×20 mL). The organic layers were separated, washed with brine, dried over Na$_2$SO$_4$, concentrated under vacuum. The crude product was purified by flash chromatography (0-10% MeOH/DCM) and lyophilized to afford the desired product as off-white powder (310 mg, 67%). $^1$H NMR (400 MHz, DMSO-d$_6$) δ 11.12 (br s, 1H), 8.98 (br s, 1H), 7.68 (d, J=8.2 Hz, 2H), 7.33 (d, J=8.2 Hz, 2H), 6.80 (dd, J=9.2, 3.0 Hz, 1H), 6.65 (td, J=8.7, 3.0 Hz, 1H), 6.05 (dd, J=9.0, 4.7 Hz, 1H), 4.46 (s, 2H), 2.77 (t, J=6.4 Hz, 2H), 1.86 (t, J=6.5 Hz, 2H), 1.20 (s, 6H). $^{13}$C NMR (100 MHz, DMSO-d$_6$) δ 164.3, 153.9 (d, J=231 Hz), 144.2, 141.7, 131.1, 127.1 (2C), 125.9 (2C), 123.6 (d, J=6.8 Hz), 114.8 (d, J=21.4 Hz), 112.8 (d, J=15.7 Hz), 112.6 (d, J=1.0 Hz), 53.9, 48.8, 36.1, 26.0 (2C), 24.2. ESI HRMS calc. for C$_{19}$H$_{22}$FN$_2$O$_2$: [M+H]$^+$, m/z 329.1660; found: 329.1648.

EXAMPLE 11

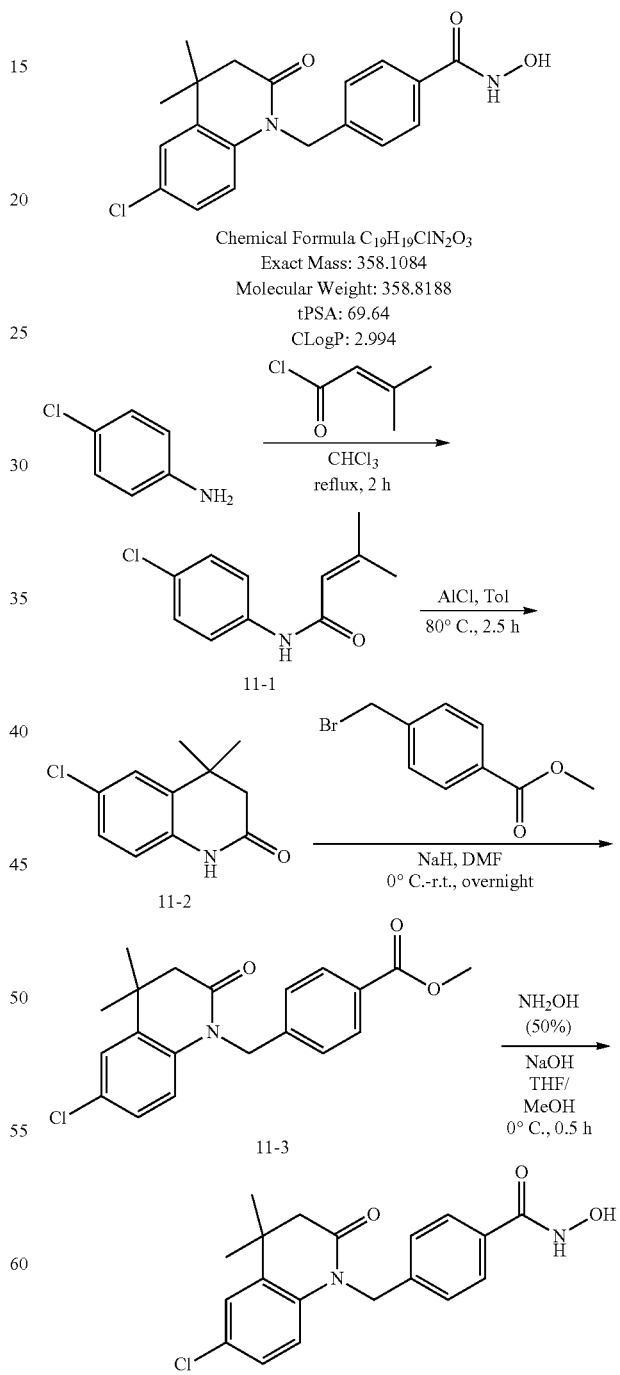

EXAMPLE 11

Synthesis of N-(4-chlorophenyl)-3-methylbut-2-enamide (11-1)

To a round bottom flask charged with 4-chloroaniline (1.27 g, 10.0 mmol) and in $CHCl_3$ (20 mL) was added 3-methylbut-2-enoyl chloride (1.18 g, 10.0 mmol). The resulting mixture was allowed to heat at reflux for 2 h. The mixture was cooled to room temperature and quenched with 2N HCl (20 mL), and then extracted with EtOAc (3×20 mL). The combined organic extracts were washed with brine (20 mL), dried over sodium sulfate, and concentrated under vacuum. The crude product was purified by flash chromatography (0-80% EtOAc/hexanes), and the title compound was obtained as white powder (1.0 g, 48%). $^1H$ NMR (400 MHz, $CDCl_3$) δ 7.54 (br, 1H), 7.47 (d, J=8.1 Hz, 2H), 7.22 (d, J=8.8 Hz, 2H), 5.70 (s, 1H), 2.19 (s, 3H), 1.86 (s, 3H). $^{13}C$ NMR (100 MHz, $CDCl_3$) δ 165.3, 154.1, 137.0, 129.0 (4C), 121.2, 118.5, 27.5, 20.1.

Synthesis of 6-chloro-4,4-dimethyl-3,4-dihydroquinolin-2(1H)-one (11-2)

To a round bottom flask charged with compound 11-1 (1.0 g, 4.78 mmol) in Tol (15 mL) was added $AlCl_3$ (2.50 g, 19.12 mmol) at room temperature. The resulting mixture was heated at 80° C. for 2 h. Then the reaction was quenched with 1 N HCl carefully at 0° C., and then extracted with EtOAc (3×15 mL). The combined organic extracts were washed with brine (20 mL), dried over sodium sulfate, and concentrated under vacuum. The crude product was purified by flash chromatography (0-80% EtOAc/hexanes) to afford as brown powder (640 mg, 64%). $^1H$ NMR (400 MHz, $CDCl_3$) δ 9.91 (br s, 1H), 7.24 (d, J=2.2 Hz, 1H), 7.13 (dd, J=8.4, 2.2 Hz, 1H), 6.83 (d, J=8.4 Hz, 1H), 2.47 (s, 2H), 1.32 (s, 6H). $^{13}C$ NMR (100 MHz, $CDCl_3$) δ 171.8, 134.7, 134.3, 128.7, 127.5, 124.8, 117.4, 45.0, 34.2, 27.6 (2C).

Synthesis of methyl 4-((6-chloro-4,4-dimethyl-2-oxo-3,4-dihydroquinolin-1(2H)-yl)methyl)benzoate (11-3)

To a round bottom flask charged with compound 11-2 (180 mg, 0.86 mmol) and in DMF (10 mL) was added NaH (70 mg, 60%, 1.72 mmol) and methyl 4-(bromomethyl)benzoate (294 mg, 1.29 mmol) at 0° C. The resulting mixture was allowed to stir at room temperature overnight. The mixture was quenched with water (10 mL) extracted with EtOAc (3×15 mL). The combined organic extracts were washed with brine (20 mL), dried over sodium sulfate, and concentrated under vacuum. The crude product was purified by flash chromatography (0-30% EtOAc/hexanes), and the title compound was obtained as brown oil (110 mg, 36%). $^1H$ NMR (400 MHz, $CDCl_3$) δ 7.98 (d, J=8.1 Hz, 2H), 7.28 (d, J=8.1 Hz, 2H), 7.26 (d, J=2.1 Hz, 1H), 7.05 (dd, J=8.7, 2.4 Hz, 1H), 6.74 (d, J=8.7 Hz, 1H), 5.22 (s, 2H), 3.88 (s, 3H), 2.64 (s, 2H), 1.33 (s, 6H). $^{13}C$ NMR (100 MHz, $CDCl_3$) δ 169.4, 166.7, 142.1, 136.9, 136.7, 130.2 (2C), 129.4, 129.0, 127.3, 126.6 (2C), 124.9, 116.9, 52.2, 46.0, 45.6, 33.5, 27.4 (2C).

Synthesis of 4-((6-chloro-4,4-dimethyl-2-oxo-3,4-dihydroquinolin-1(2H)-yl)methyl)-N-hydroxybenzamide (Example 11)

In a round bottom flask, NaOH (100 mg, 1.6 mmol) was dissolved in 50% aqueous $NH_2OH$ (1.0 mL, approx. 50 equiv.) at 0° C. A solution of compound 11-4 (110 mg, 0.31 mmol) in 1:1 THF/MeOH (4 mL) was added dropwise, and stirring was continued for 30 min while warming to room temperature. The solution was neutralized with 2N HCl and extracted with EtOAc (3×15 mL). The organic layers were separated, washed with brine, dried over $Na_2SO_4$, concentrated under vacuum. The crude product was purified by flash chromatography (0-10% MeOH/DCM) to afford the desired product as off-white powder (30 mg, 27%). $^1H$ NMR (400 MHz, CD3OD) δ 7.69 (d, J=8.2 Hz, 2H), 7.34 (dd, J=5.2, 2.8 Hz, 3H), 7.11 (dd, J=8.7, 2.4 Hz, 1H), 6.93 (d, J=8.7 Hz, 1H), 5.25 (s, 2H), 2.64 (s, 2H), 1.31 (s, 6H). $^{13}C$ NMR (100 MHz, $CD_3OD$) δ 171.8, 167.8, 142.2, 138.4, 138.0, 132.6, 130.3, 128.6 (2C), 128.2, 128.1 (2C), 125.8, 118.7, 46.6, 46.3, 34.3, 27.5 (2C). ESI HRMS calc. for $C_{19}H_{20}ClN_2O_3$: $[M+H]^+$, m/z 359.1157; found: 359.1137.

EXAMPLE 12

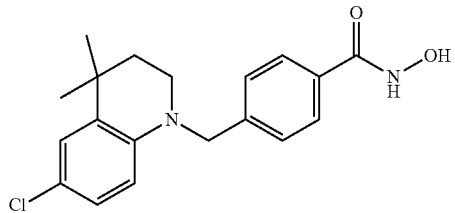

Chemical Formula $C_{19}H_{21}ClN_2O_2$
Exact Mass: 344.1292
Molecular Weight: 344.8352
tPSA: 52.57
CLogP: 4.7738

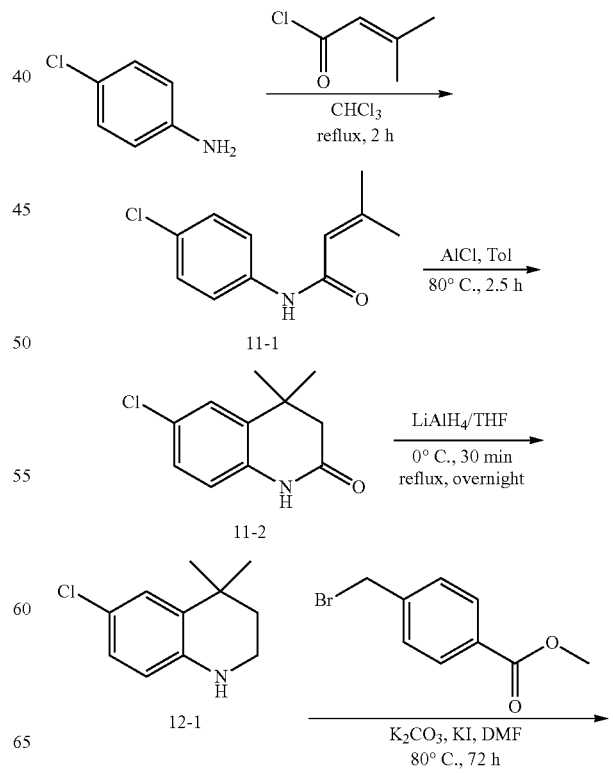

55

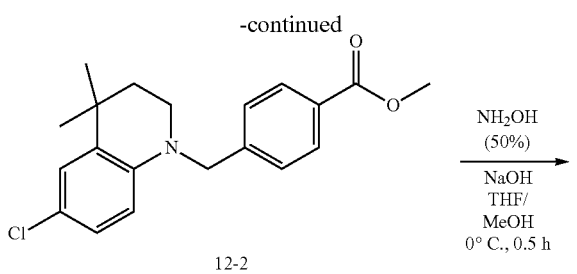

Synthesis of 6-chloro-4,4-dimethyl-1,2,3,4-tetrahydroquinoline (12-1)

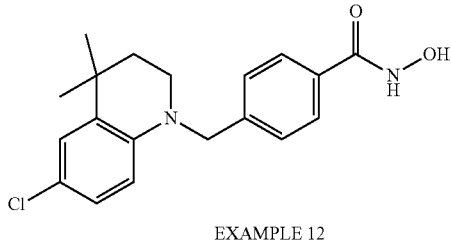

To a stirred solution of compound 11-2 (460 mg, 2.20 mmol) in THF (20 mL) were added LiAlH₄ (250 mg, 6.60 mmol) at 0° C. The resulting mixture was stirred at same temperature for 30 min, heated at reflux overnight. The reaction was quenched with water (0.25 mL), 5 N NaOH (0.25 mL), and water (1.25 mL). The afforded participate was filtered off, and the filtrate was concentrated under vacuum. The crude product was purified by flash chromatography (0-10% EtOAc/hexanes), and the title compound was obtained as colorless oil (370 mg, 86%). $^1$H NMR (400 MHz, CDCl$_3$) δ 7.15 (d, J=2.4 Hz, 1H), 6.91 (dd, J=8.5, 2.4 Hz, 1H), 6.39 (d, J=8.5 Hz, 1H), 3.83 (s, 1H), 3.37-3.24 (m, 2H), 1.81-1.67 (m, 2H), 1.30 (s, 6H). $^{13}$C NMR (100 MHz, CDCl$_3$) δ 142.3, 131.8, 126.5, 126.3, 121.4, 115.3, 38.4, 36.9, 32.0, 30.9 (2C).

Synthesis of methyl 4-((6-chloro-4,4-dimethyl-3,4-dihydroquinolin-1(2H)-yl)methyl)benzoate (12-2)

To a round bottom flask charged with compound 12-1 (370 mg, 1.90 mmol) and methyl 4-(bromomethyl)benzoate (650 mg, 2.85 mmol) in DMF (10 mL) was added K$_2$CO$_3$ (524 mg, 3.80 mmol) and KI (33 mg, 0.19 mmol). The resulting mixture was allowed to stir overnight at 80° C. The mixture was cooled to room temperature and after addition of water (30 mL) extracted with EtOAc (3×25 mL). The combined organic extracts were washed with brine (30 mL), dried over sodium sulfate, and concentrated under vacuum. The crude product was purified by flash chromatography (0-10% EtOAc/hexanes) and the title compound was obtained as light yellow oil (70 mg, 86%). $^1$H NMR (400 MHz, CDCl$_3$) δ 8.00 (d, J=8.3 Hz, 2H), 7.30 (d, J=8.4 Hz, 2H), 7.16 (d, J=2.5 Hz, 1H), 6.88 (dd, J=8.8, 2.5 Hz, 1H), 6.31 (d, J=8.8 Hz, 1H), 4.52 (s, 2H), 3.91 (s, 3H), 3.43-3.30 (m, 2H), 1.85-1.74 (m, 2H), 1.30 (s, 6H). $^{13}$C NMR (100 MHz, CDCl$_3$) δ 167.0, 144.1, 142.6, 132.8, 130.2 (2C), 129.1, 126.7, 126.5 (2C), 125.9, 121.0, 112.2, 55.5, 52.2, 46.5, 36.8, 32.4, 30.4 (2C).

56

Synthesis of 4-((6-chloro-4,4-dimethyl-3,4-dihydroquinolin-1(2H)-yl)methyl)-N-hydroxybenzamide (Example 12)

In a round bottom flask, NaOH (64 mg, 1.6 mmol) was dissolved in 50% aqueous NH$_2$OH (0.5 mL, approx. 50 equiv.) at 0° C. A solution of compound 12-2 (70 mg, 0.2 mmol) in 1:1 THF/MeOH (4 mL) was added dropwise, and stirring was continued for 30 min while warming to room temperature. The solution was neutralized with 2N HCl and extracted with EtOAc (3×15 mL). The organic layers were separated, washed with brine, dried over Na$_2$SO$_4$, concentrated under vacuum. The crude product was purified by flash chromatography (0-10% MeOH/DCM), prep-HPLC and lyophilized to afford the desired product as off-white powder (30 mg, 44%). $^1$H NMR (400 MHz, DMSO-d$_6$) δ 11.11 (br s, 1H), 8.98 (br s, 1H), 7.69 (d, J=8.3 Hz, 2H), 7.27 (d, J=8.2 Hz, 2H), 7.13 (d, J=2.6 Hz, 1H), 6.87 (dd, J=8.8, 2.6 Hz, 1H), 6.37 (d, J=8.9 Hz, 1H), 4.54 (s, 2H), 3.41-3.37 (m, 2H), 1.78-1.71 (m, 2H), 1.25 (s, 6H). $^{13}$C NMR (100 MHz, DMSO-d$_6$) δ 164.1, 142.4, 141.9, 132.5, 131.4, 127.2 (2C), 126.4 (2C), 126.2, 125.2, 119.0, 112.2, 54.1, 45.8, 36.0, 32.0, 30.0 (2C). ESI HRMS calc. for C$_{19}$H$_{22}$ClN$_2$O$_2$: [M+H]$^+$, m/z 345.1346; found: 345.1363.

EXAMPLE 13

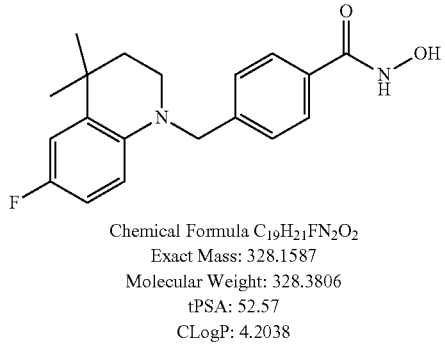

Chemical Formula C$_{19}$H$_{21}$FN$_2$O$_2$
Exact Mass: 328.1587
Molecular Weight: 328.3806
tPSA: 52.57
CLogP: 4.2038

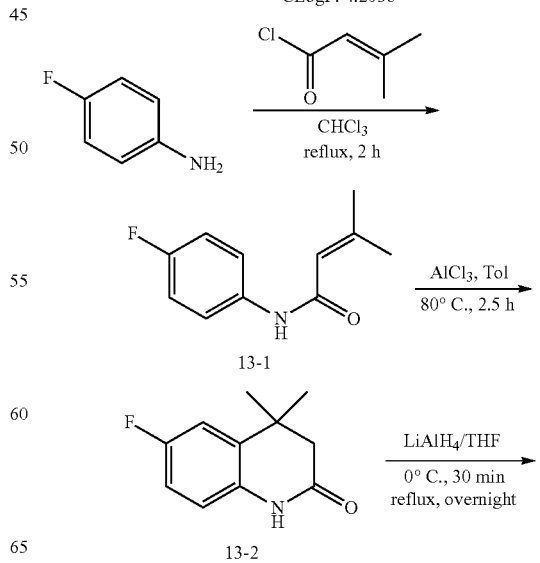

-continued

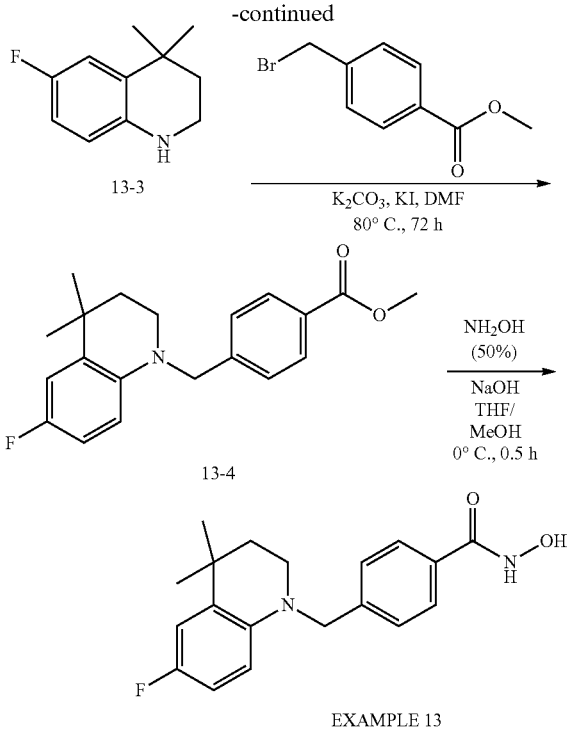

EXAMPLE 13

Synthesis of N-(4-fluorophenyl)-3-methylbut-2-enamide (13-1)

To a round bottom flask charged with 4-fluoroaniline (1.11 g, 10.0 mmol) and in CHCl$_3$ (20 mL) was added 3-methylbut-2-enoyl chloride (1.18 g, 10.0 mmol). The resulting mixture was allowed to heat at reflux for 2 h. The mixture was cooled to room temperature and quenched with 2N HCl (20 mL), and then extracted with EtOAc (3×20 mL). The combined organic extracts were washed with brine (20 mL), dried over sodium sulfate, and concentrated under vacuum. The crude product was purified by flash chromatography (0-20% EtOAc/hexanes), and the title compound was obtained as off-white powder (1.0 g, 52%). $^1$H NMR (400 MHz, CDCl$_3$) δ 7.67 (br s, 1H), 7.47 (dd, J=7.0, 4.7 Hz, 2H), 7.02-6.88 (m, 2H), 5.70 (d, J=1.1 Hz, 1H), 2.18 (s, 3H), 1.85 (s, 3H). $^{13}$C NMR (100 MHz, CDCl$_3$) δ 165.4, 159.3 (d, J=242 Hz), 153.5 (d, J=3.0 Hz), 134.4, 121.8 (d, J=5.4 Hz, 2C), 118.6, 115.5 (d, J=22 Hz, 2C), 27.4 (2C), 20.0.

Synthesis of 6-fluoro-4,4-dimethyl-3,4-dihydroquinolin-2(1H)-one (13-2)

To a round bottom flask charged with compound 13-1 (1.0 g, 5.24 mmol) in Tol (15 mL) was added AlCl$_3$ (2.78 g, 20.94 mmol) at room temperature. The resulting mixture was heated at 80° C. for 2 h. Then the reaction was quenched with 1 N HCl carefully at 0° C., and then extracted with EtOAc (3×15 mL). The combined organic extracts were washed with brine (20 mL), dried over sodium sulfate, and concentrated under vacuum. The crude product was purified by flash chromatography (0-50% EtOAc/hexanes) to afford as brown powder (440 mg, 44%). $^1$H NMR (400 MHz, CDCl$_3$) δ 9.86 (s, 1H), 7.06-6.92 (m, 1H), 6.92-6.73 (m, 2H), 2.47 (s, 2H), 1.31 (s, 6H). $^{13}$C NMR (100 MHz, CDCl$_3$) δ 171.1, 158.9 (d, J=240 Hz), 134.1 (d, J=6.7 Hz), 131.7 (d, J=2.4 Hz), 116.7 (d, J=8.1 Hz), 113.5 (d, J=22.7 Hz), 111.2 (d, J=23.5 Hz), 44.4, 33.7, 27.1 (2C).

Synthesis of 6-fluoro-4,4-dimethyl-1,2,3,4-tetrahydroquinoline (13-3)

To a stirred solution of compound 13-2 (440 mg, 2.28 mmol) in THF (20 mL) were added LiAlH$_4$ (260 mg, 6.83 mmol) at 0° C. The resulting mixture was stirred at same temperature for 30 min, heated at reflux overnight. The reaction was quenched with water (0.26 mL), 5 N NaOH (0.26 mL), and water (1.30 mL). The afforded participate was filtered off, and the filtrate was concentrated under vacuum. The crude product was purified by flash chromatography (0-50% EtOAc/hexanes), and the title compound was obtained as brown oil (310 mg, 76%). $^1$H NMR (400 MHz, CDCl$_3$) δ 6.91 (dd, J=10.3, 2.9 Hz, 1H), 6.68 (ddd, J=8.7, 8.2, 2.9 Hz, 1H), 6.40 (dd, J=8.7, 5.0 Hz, 1H), 3.56 (br s, 1H), 3.34-3.19 (m, 2H), 1.81-1.65 (m, 2H), 1.29 (s, 6H). $^{13}$C NMR (100 MHz, CDCl$_3$) δ 155.8 (d, J=232 Hz), 139.9 (d, J=1.4 Hz), 131.8 (d, J=5.7 Hz), 115.1 (d, J=7.5 Hz), 113.3 (d, J=22.3 Hz), 113.0 (d, J=22.0 Hz), 38.7, 37.2, 32.2, 31.2 (2C).

Synthesis of methyl 4-((6-fluoro-4,4-dimethyl-3,4-dihydroquinolin-1(2H)-yl)methyl)benzoate (13-4)

To a round bottom flask charged with compound 13-3 (310 mg, 1.73 mmol) and methyl 4-(bromomethyl)benzoate (592 mg, 2.60 mmol) in DMF (10 mL) was added K$_2$CO$_3$ (477 mg, 3.46 mmol) and KI (30 mg, 0.17 mmol). The resulting mixture was allowed to stir overnight at 80° C. The mixture was cooled to room temperature and after addition of water (30 mL) extracted with EtOAc (3×25 mL). The combined organic extracts were washed with brine (30 mL), dried over sodium sulfate, and concentrated under vacuum. The crude product was purified by flash chromatography (0-10% EtOAc/hexanes) and the title compound was obtained as light yellow oil (310 mg, 55%). $^1$H NMR (400 MHz, CDCl$_3$) δ 8.00 (d, J=8.3 Hz, 2H), 7.32 (d, J=8.0 Hz, 2H), 6.95 (dd, J=10.2, 3.0 Hz, 1H), 6.65 (ddd, J=8.9, 8.1, 3.0 Hz, 1H), 6.30 (dd, J=8.9, 4.8 Hz, 1H), 4.50 (s, 2H), 3.91 (s, 3H), 3.45-3.27 (m, 2H), 1.91-1.75 (m, 2H), 1.32 (s, 6H). $^{13}$C NMR (100 MHz, CDCl$_3$) δ 167.1, 155.3 (d, J=233 Hz), 144.6, 140.5 (d, J=1.2 Hz), 132.8 (d, J=5.7 Hz), 130.2 (2C), 129.1, 126.6 (2C), 113.1 (d, J=21.6 Hz), 112.8 (d, J=22.2 Hz), 111.9 (d, J=7.3 Hz), 56.0, 52.2, 46.6, 37.1, 32.6, 30.6 (2C).

Synthesis of 4-((6-fluoro-4,4-dimethyl-3,4-dihydroquinolin-1(2H)-yl)methyl)-N-hydroxybenzamide (Example 13)

In a round bottom flask, NaOH (305 mg, 7.6 mmol) was dissolved in 50% aqueous NH$_2$OH (3.10 mL, approx. 50 equiv.) at 0° C. A solution of compound 13-4 (310 mg, 0.95 mmol) in 1:1 THF/MeOH (8 mL) was added dropwise, and stirring was continued for 30 min while warming to room temperature. The solution was neutralized with 2N HCl and extracted with EtOAc (3×20 mL). The organic layers were separated, washed with brine, dried over Na$_2$SO$_4$, concentrated under vacuum. The crude product was purified by flash chromatography (0-10% MeOH/DCM) and lyophilized to afford the desired product as orange powder (210 mg, 67%). $^1$H NMR (400 MHz, DMSO-d$_6$) δ 11.14 (br s, 1H), 8.99 (br s, 1H), 7.70 (d, J=8.2 Hz, 2H), 7.29 (d, J=8.2

Hz, 2H), 7.00 (dd, J=10.4, 3.1 Hz, 1H), 6.69 (td, J=8.6, 3.1 Hz, 1H), 6.34 (dd, J=9.0, 4.9 Hz, 1H), 4.51 (s, 2H), 3.37 (m, 2H, overlap with water peak), 1.78-1.71 (m, 2H), 1.25 (s, 6H). $^{13}$C NMR (100 MHz, DMSO-$d_6$) δ 164.2, 154.2 (d, J=229 Hz), 142.4, 140.3, 132.2 (d, J=5.6 Hz), 131.4, 127.2 (2C), 126.5 (2C), 112.7 (d, J=21.6 Hz), 112.4 (d, J=22.0 Hz), 111.5 (d, J=7.4 Hz), 54.6, 45.9, 36.3, 32.1, 30.3 (2C). ESI HRMS calc. for $C_{19}H_{22}FN_2O_2$: $[M+H]^+$, m/z 329.1660; found: 329.1659.

EXAMPLE 14

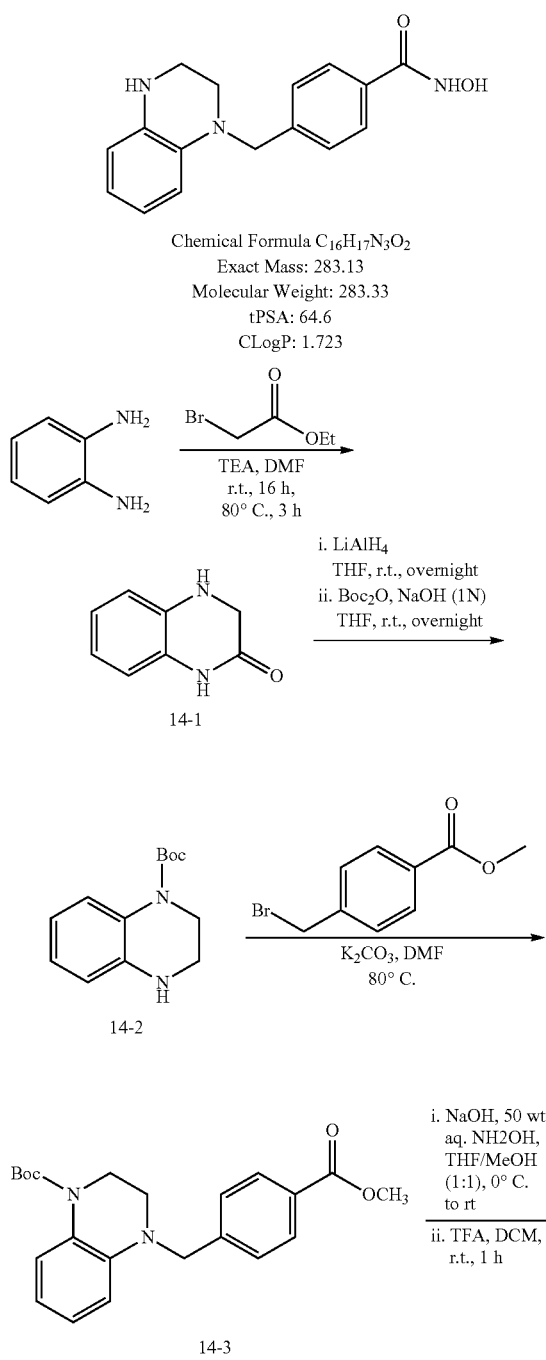

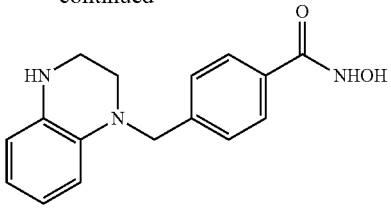

EXAMPLE 14

Synthesis of 3,4-dihydroquinoxalin-2(1H)-one (14-1)

To a stirred solution of benzene-1,2-diamine (1.0 g, 9.25 mmol) in DMF was added TEA (2.4 mL, 17.1 mmol), followed by Ethyl bromoacetate (1.7 g, 10.2 mmol). The reaction mixture was stirred at r.t. for 16 h, then at 80° C. for another 3 h. The reaction was quenched with H$_2$O, and extracted with EtOAc (3×20 mL). The combined organic extracts were washed with brine (40 mL), dried over sodium sulfate, and concentrated under vacuum. The crude product was purified by flash chromatography (0-80% EtOAc/hexane), and the title compound was obtained as colorless oil (900 mg, 66%). $^1$H NMR (400 MHz, CDCl$_3$) δ 8.74 (s, 1H), 6.89 (ddd, J=7.8, 5.1, 3.8 Hz, 1H), 6.74 (t, J=8.7 Hz, 2H), 6.67 (d, J=8.1 Hz, 1H), 3.99 (d, J=1.6 Hz, 2H), 3.85 (s, 1H).

Synthesis of tert-butyl 3,4-dihydroquinoxaline-1(2H)-carboxylate (14-2)

To a stirred solution of compound 14-1 (270 mg, 2 mmol) in THF (10 mL) was added LiAlH$_4$ (228 mg, 6 mmol) at 0° C. The resulting mixture was stirred at 0° C. for 30 min then stirred at room temperature overnight. The reaction was quenched with 0.25 mL H$_2$O, 0.25 mL 5N NaOH and 1.25 mL H$_2$O. The participate was filtered off, and the filtrate was extracted with EtOAc (3×20 mL). The organic layers were separated, washed with brine, dried over sodium sulfate, and concentrated under vacuum. The crude product was purified by flash chromatography (0-60% EtOAc/hexane) to obtain as light yellow solid (90 mg, 34%). To a stirred solution of the intermediate afforded in last step (90 mg, 0.67 mmol) in THF was added Boc$_2$O (146 mg, 0.67 mmol) and aqueous solution NaOH (1N, 0.67 mL) at 0° C. Then the resulting mixture was stirred at room temperature overnight. The reaction was quenched with water, extracted with EtOAc (3×10 mL). The organic layers were separated, washed with brine, dried over sodium sulfate, and concentrated under vacuum. The crude product was purified by flash chromatography (0-60% EtOAc/hexanes) to obtain as light yellow oil (90 mg, 57%). $^1$H NMR (400 MHz, CDCl$_3$) δ 7.49 (d, J=7.7 Hz, 1H), 6.89 (td, J=8.0, 1.4 Hz, 1H), 6.69-6.60 (m, 1H), 6.55 (dd, J=8.0, 1.3 Hz, 1H), 3.94 (s, 1H), 3.83-3.69 (m, 2H), 3.47-3.34 (m, 2H), 1.52 (s, 9H).

Synthesis of tert-butyl 4-(4-(methoxycarbonyl)benzyl)-3,4-dihydroquinoxaline-1(2H)-carboxylate (14-3)

To a round bottom flask charged with compound 14-2 (90 mg, 0.38 mmol) and methyl 4-(bromomethyl)benzoate (87 mg, 0.38 mmol) in DMF (5 mL) was added K$_2$CO$_3$ (105 mg, 0.76 mmol). The resulting mixture was allowed to stir for 2 h at 80° C. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-5% MeOH/DCM), and the title compound was obtained as an off-white waxy solid (90 mg, 60%). $^1$H NMR (CDCl$_3$) δ 7.99, 7.32 (AA'XX' multiplet, $J_{AX}+J_{AX'}$=8.2 Hz, 4H), 7.48 (br d, J=7.4 Hz, 1H), 7.32 (d, J=7.9 Hz, 2H), 6.90 (incompletely resolved ddd approaching dt, average of two larger J=7.8 Hz, additional J=1.1 Hz, 1H), 6.66 (incompletely resolved ddd approaching dt, average of two larger J=7.6 Hz, additional J=1.2 Hz, 1H), 6.55 (dd, J=8.2 Hz, 0.9 Hz, 1H), 4.56 (s, 2H), 3.90 (s, 3H), 3.86, 3.44 (AA'XX' multiplet, $J_{AX}+J_{AX'}$=10.2 Hz, 4H), 1.53 (s, 9H). $^{13}$C NMR (DMSO-d$_6$) δ 166.9, 153.3, 143.7, 138.2, 130.1 (2C), 129.1, 126.5 (2C), 125.1, 124.7, 116.3, 111.6, 100.0, 81.1, 54.9, 52.1, 49.5, 41.6, 28.4 (3C). ESI LRMS: [M+H]$^+$, m/z 383.3.

Synthesis of 4-((3,4-dihydroquinoxalin-1(2H)-yl)methyl)-N-hydroxybenzamide (Example 14)

In a round bottom flask, NaOH (212 mg, 5.3 mmol) was dissolved in 50% aqueous NH$_2$OH (1.5 mL, approx. 50 equiv) at 0° C. A solution of compound 14-3 (260 mg, 0.66 mmol) in 1:1 THF/MeOH (6 mL) was added dropwise, and stirring was continued for 30 min while warming to room temperature. The solution was neutralized with 6N HCl and extracted with EtOAc (3×10 mL). The combined organic phases were washed with brine, dried over sodium sulfate, and concentrated under vacuum. The crude material was dissolved in DCM (5 mL). Trifluoroacetic acid (2 mL) was added, and the solution was allowed to stir 30 min before again being concentrated. The combined organic extracts were washed with brine (20 mL), dried over sodium sulfate, and concentrated under vacuum. The residue was purified by preparative HPLC to afford the title compound as light gray solid (47 mg, 24%, two steps) after lyophilization. $^1$H NMR (DMSO-d$_6$) δ 11.15 (s, 1H), 8.99 (s, 1H), 7.70 (d, J=8.1 Hz, 2H), 7.34 (d, J=8.0 Hz, 2H), 6.57-6.16 (m, 4H), 5.48 (br s, 1H), 4.43 (s, 2H), 3.34 (s, 4H). $^{13}$C NMR (DMSO-d$_6$) δ 164.2, 142.6, 135.0, 134.1, 131.3, 127.0 (2C), 126.9 (2C), 117.3, 117.0, 113.1, 111.2, 54.2, 48.2, 40.1. ESI HRMS calc. for C$_{16}$H$_{16}$N$_3$O$_2$: [M–H]$^+$, m/z 282.1248; found: 282.1248.

EXAMPLE 15

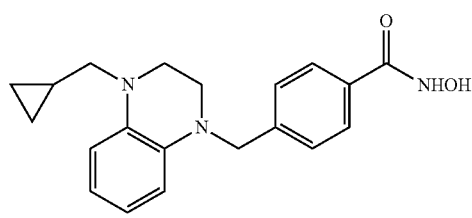

Chemical Formula C$_{20}$H$_{23}$N$_3$O$_2$
Exact Mass: 337.1790
Molecular Weight: 337.4155
tPSA: 55.81
CLogP: 3.482

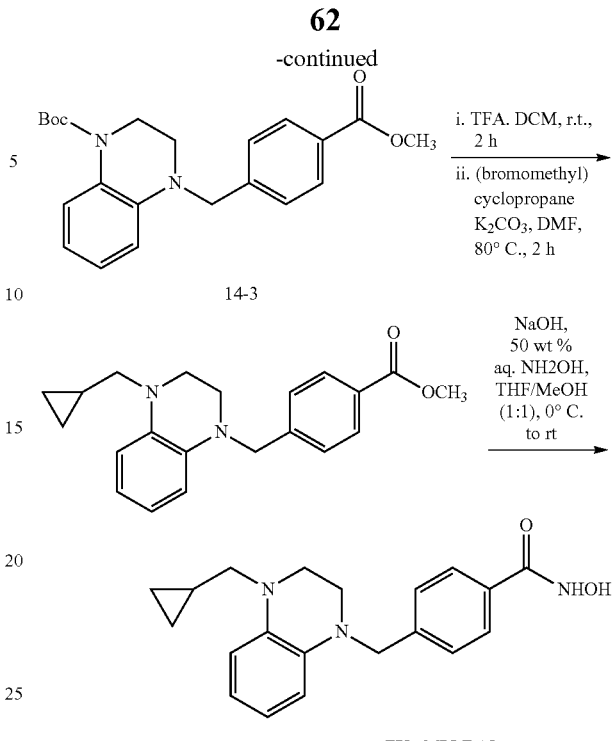

EXAMPLE 15

Synthesis of methyl 4-((4-(cyclopropylmethyl)-3,4-dihydroquinoxalin-1(2H)-yl)methyl)benzoate (15-1)

To a round bottom flask charged with compound 14-3 (200 mg, 0.52 mmol) in DCM (2 mL) was added trifluoroacetic acid (1 mL), and the resulting solution was allowed to stir for 30 min. The excess acid and solvent were removed under vacuum. The crude product was neutralized with saturated aqueous sodium carbonate and extracted with EtOAc (3×10 mL). The combined organic layers were washed with copious volumes of water and with brine, dried over sodium sulfate, and concentrated under vacuum. The deprotection product (120 mg, 0.42 mmol) was dissolved in DMF (3 mL), and K$_2$CO$_3$ (116 mg, 0.84 mmol) and (bromomethyl)cyclopropane (84 mg, 0.63 mmol) were added. The resulting mixture was heated at 80° C. for 2 h. Then the reaction was quenched by the addition of water (15 mL), and the organics were extracted with EtOAc (3×10 mL). The combined organic layers were washed with copious volumes of water and with brine, dried over sodium sulfate, and concentrated under vacuum. The crude product was purified by flash chromatography (0-5% MeOH/DCM) afforded as light yellow oil (130 mg, 0.40 mmol).

Synthesis of 4-((4-(cyclopropylmethyl)-3,4-dihydroquinoxalin-1(2H)-yl)methyl)-N-hydroxybenzamide (Example 15)

In a round bottom flask, NaOH (128 mg, 3.2 mmol) was dissolved in 50% aqueous NH$_2$OH (1.0 mL, approx. 50 equiv) at 0° C. A solution of compound 15-1 (130 mg, 0.40 mmol) in 1:1 THF/MeOH (6 mL) was added dropwise, and stirring was continued for 30 min while warming to room temperature. The solution was neutralized with 6N HCl and extracted with EtOAc (3×10 mL). The combined organic phases were washed with brine, dried over sodium sulfate, and concentrated under vacuum. The crude product was purified by flash chromatography (0-10% MeOH/DCM) afforded (60 mg, 44% over three steps); $^1$H NMR (DMSO-d$_6$) δ 11.15 (s, 1H), 8.99 (s, 1H), 7.70 (d, J=8.0 Hz, 2H), 7.33 (d, J=8.0 Hz, 2H), 6.58 (d, J=7.8 Hz, 1H), 6.49 (t, J=7.5 Hz, 1H), 6.40 (t, J=7.4 Hz, 1H), 6.34 (d, J=7.0 Hz, 1H), 4.45 (s, 2H), 3.42 (s, 4H), 3.09 (d, J=6.4 Hz, 2H), 1.07-0.93 (m, 1H), 0.48 (q, J=4.9 Hz, 2H), 0.23 (q, J=4.9 Hz, 2H). $^{13}$C NMR (DMSO-d$_6$) δ 164.2, 142.4, 135.2, 135.1, 131.3, 127.1 (2C), 126.8 (2C), 117.4, 117.3, 111.0, 110.9, 54.8, 54.4, 48.1, 46.5, 7.7, 3.4 (2C). ESI HRMS calc. for C$_{20}$H$_{22}$N$_3$O$_2$: [M–H]$^+$, m/z 336.1718; found: 336.1710.

EXAMPLE 16

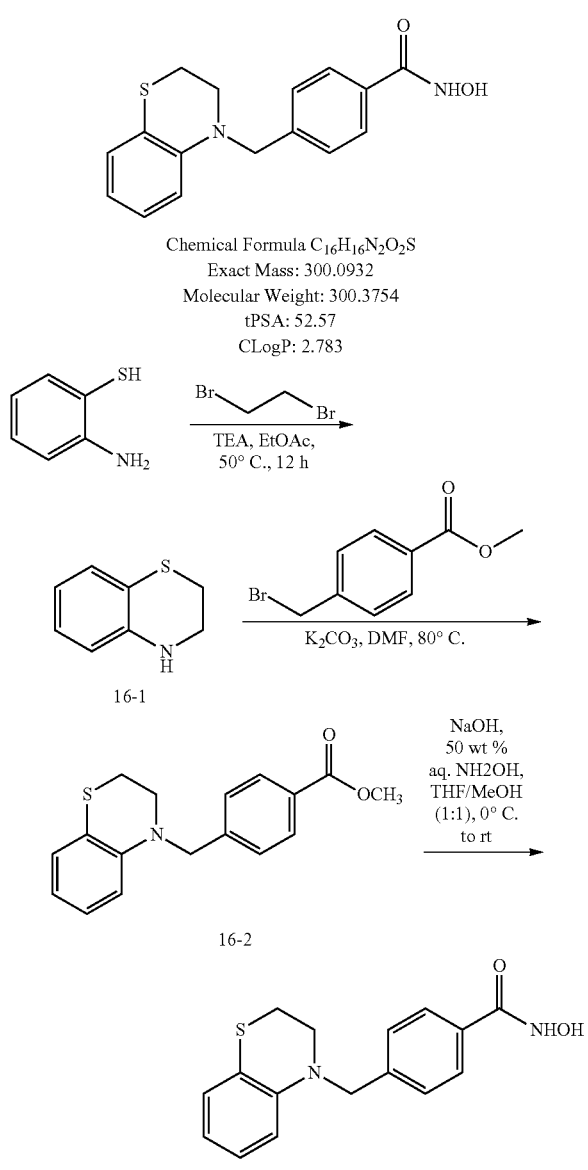

EXAMPLE 16

Synthesis of 3,4-dihydro-2H-benzo[b][1,4]thiazine (16-1)

To a stirred solution of 2-aminobenzenethiol (1.0 g, 8.0 mmol) and 1,2-dibromoethane (1.8 g, 10 mmol) in EtOAc (4 mL) was dropwise added TEA (2.0 mL) during 2 h at 50° C. Then the resulting mixture was stirred at same temperature for 12 h. The reaction was quenched with H$_2$O (10 mL), extracted with EtOAc (3×20 mL). The combined organic phases were washed with brine, dried over sodium sulfate, and concentrated under vacuum. The crude product was purified by flash chromatography (0-50% EtOAc/hexanes) to afford as light yellow oil (390 mg, 32%); $^1$H NMR (400 MHz, CDCl$_3$) δ 6.98 (dd, J=7.7, 1.4 Hz, 1H), 6.88 (td, J=8.0, 1.5 Hz, 1H), 6.61 (td, J=7.6, 1.2 Hz, 1H), 6.45 (dd, J=8.0, 1.2 Hz, 1H), 3.93 (s, 1H), 3.67-3.57 (m, 2H), 3.10-3.00 (m, 2H). $^{13}$C NMR (100 MHz, CDCl$_3$) δ 141.7, 127.7, 125.5, 118.2, 116.0, 115.3, 42.3, 26.1.

Synthesis of methyl 4-((2,3-dihydro-4H-benzo[b][1,4]thiazin-4-yl)methyl)benzoate (16-2)

To a round bottom flask charged with compound 16-1 (151 mg, 1.0 mmol) and methyl 4-(bromomethyl)benzoate (228 mg, 1.0 mmol) in DMF (5 mL) was added K$_2$CO$_3$ (276 mg, 2.0 mmol). The resulting mixture was allowed to stir for 2 h at 80° C. The mixture was cooled to room temperature and after addition of water (15 mL) extracted with EtOAc (3×15 mL). The combined organic extracts were washed with brine (20 mL), dried over sodium sulfate, and concentrated under vacuum. The crude product was purified by flash chromatography (0-50% EtOAc/hexanes) to afford as colorless oil (110 mg, 37%). $^1$H NMR (CDCl$_3$) δ 8.00, 7.33 (AA'XX' multiplet, J$_{AX}$+J$_{AX'}$=8.4 Hz, 4H), 7.08 (dd, J=7.7 Hz, 1.5 Hz, 1H), 6.90 (incompletely resolved ddd approaching dt, average of two larger J=7.8 Hz, additional J=1.1 Hz, 1H), 6.63 (incompletely resolved ddd approaching dt, average of two larger J=7.5 Hz, additional J=0.8 Hz, 1H), 6.54 (dd, J=8.3 Hz, 0.7 Hz, 1H), 4.57 (s, 2H), 3.90 (s, 3H), 3.69, 3.08 (AA'XX' multiplet, J$_{AX}$+J$_{AX'}$=10.4 Hz, 4H). $^{13}$C NMR (CDCl$_3$) δ 166.9, 143.8, 143.4, 130.1 (2C), 129.1, 128.0, 126.6 (2C), 126.1, 118.0, 117.8, 113.2, 56.3, 52.1, 50.6, 25.9. ESI LRMS: [M+H]$^+$, m/z 300.2.

Synthesis of 4-((2,3-dihydro-4H-benzo[b][1,4]thiazin-4-yl)methyl)-N-hydroxybenzamide (Example 16)

In a round bottom flask, NaOH (118 mg, 2.96 mmol) was dissolved in 50% aqueous NH$_2$OH (1.0 mL, approx. 50 equiv) at 0° C. A solution of compound 16-2 (110 mg, 0.37 mmol) in 1:1 THF/MeOH (6 mL) was added dropwise, and stirring was continued for 30 min while warming to room temperature. The solution was neutralized with 6N HCl and extracted with EtOAc (3×10 mL). The combined organic phases were washed with brine, dried over sodium sulfate, and concentrated under vacuum. The crude product was washed with EtOAc to afford as white powder (95 mg, 80%). $^1$H NMR (DMSO-d$_6$) δ 11.17 (s, 1H), 9.01 (s, 1H), 7.72 (d, J=8.1 Hz, 2H), 7.32 (d, J=8.1 Hz, 2H), 6.97 (dd, J=7.9, 1.2 Hz, 1H), 6.83 (t, J=7.7 Hz, 1H), 6.53 (t, J=7.0 Hz, 2H), 3.78-3.55 (m, 2H), 3.20-2.99 (m, 2H). $^{13}$C NMR (DMSO-d$_6$) δ 164.1, 143.0, 142.0, 131.4, 127.4, 127.2 (2C), 126.5 (2C), 125.8, 116.9, 116.9, 112.8, 55.0, 50.4, 25.0. ESI HRMS calc. for C$_{16}$H$_{15}$N$_2$O$_2$S: [M–H]$^+$, m/z 299.0860; found: 299.0877.

EXAMPLE 17

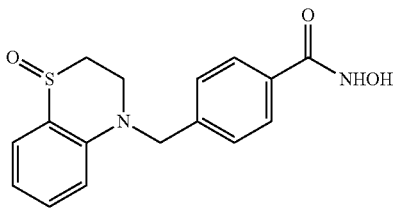

Chemical Formula C$_{16}$H$_{16}$N$_2$O$_3$S
Exact Mass: 316.0882
Molecular Weight: 316.3748
tPSA: 69.64
CLogP: 1.0855

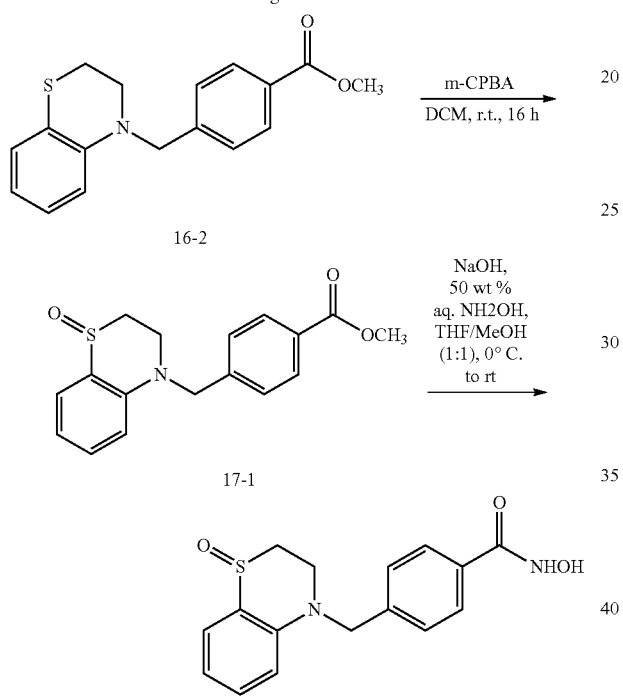

Synthesis of methyl 4-((1-oxido-2,3-dihydro-4H-benzo[b][1,4]thiazin-4-yl)methyl)benzoate (17-1)

To a stirred solution of compound 16-2 (150 mg, 0.5 mmol) in DCM was added m-CPBA (86 mg, 0.5 mmol) at 0° C. Then the resulting mixture was stirred at room temperature for 16 h. The reaction was quenched with water, extracted with EtOAc (3×10 mL). The combined organic phases were washed with brine, dried over sodium sulfate, and concentrated under vacuum. The crude product was purified by flash chromatography (0-10% MeOH/DCM) to afford as colorless oil (130 mg, 83%). ESI LRMS: [M+H]$^+$, m/z 316.1, [M+Na]$^+$, m/z 328.1.

Synthesis of N-hydroxy-4-((1-oxido-2,3-dihydro-4H-benzo[b][1,4]thiazin-4-yl)methyl)benzamide (Example 17)

In a round bottom flask, NaOH (131 mg, 3.3 mmol) was dissolved in 50% aqueous NH$_2$OH (1.0 mL, approx. 50 equiv) at 0° C. A solution of compound 18-1 (130 mg, 0.42 mmol) in 1:1 THF/MeOH (6 mL) was added dropwise, and stirring was continued for 30 min while warming to room temperature. The solution was neutralized with 6N HCl and extracted with n-BuOH (3×10 mL). The combined organic phases were washed with brine, dried over sodium sulfate, and concentrated under vacuum. The crude product was washed with EtOAc to afford as white powder (100 mg, 77%). $^1$H NMR (DMSO-d$_6$) δ 7.71 (d, J=7.8 Hz, 2H), 7.50 (d, J=7.4 Hz, 1H), 7.31 (d, J=7.9 Hz, 2H), 7.26 (d, J=7.8 Hz, 1H), 6.76 (d, J=8.6 Hz, 1H), 6.68 (t, J=7.1 Hz, 1H), 4.78 (dd, J=46.2, 17.5 Hz, 2H), 3.99 (t, J=13.9 Hz, 1H), 3.67 (d, J=13.8 Hz, 1H), 3.14 (d, J=12.1 Hz, 1H), 2.96 (t, J=14.1 Hz, 1H). $^{13}$C NMR (CD$_3$OD) δ 167.8, 144.7, 143.0, 135.6, 134.5, 132.5, 128.6 (2C), 127.7 (2C), 121.7, 117.5, 115.1, 56.3, 42.3, 39.6. ESI HRMS calc. for C$_{16}$H$_{15}$N$_2$O$_3$S: [M−H]$^+$, m/z 315.0809; found: 315.0801.

EXAMPLE 18

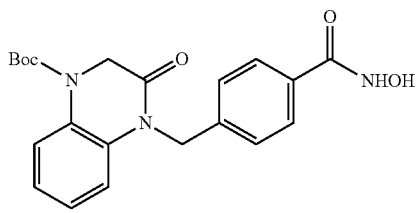

Chemical Formula: C$_{21}$H$_{23}$N$_3$O$_5$
Exact Mass: 397.16
Molecular Weight: 397.42
tPSA: 99.18
CLogP: 2.0934

EXAMPLE 19

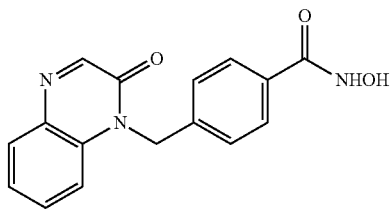

Chemical Formula C$_{16}$H$_{13}$N$_3$O$_3$
Exact Mass: 295.0957
Molecular Weight: 295.2927
tPSA: 82
CLogP: 0.528

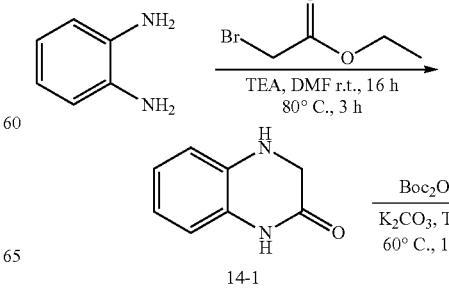

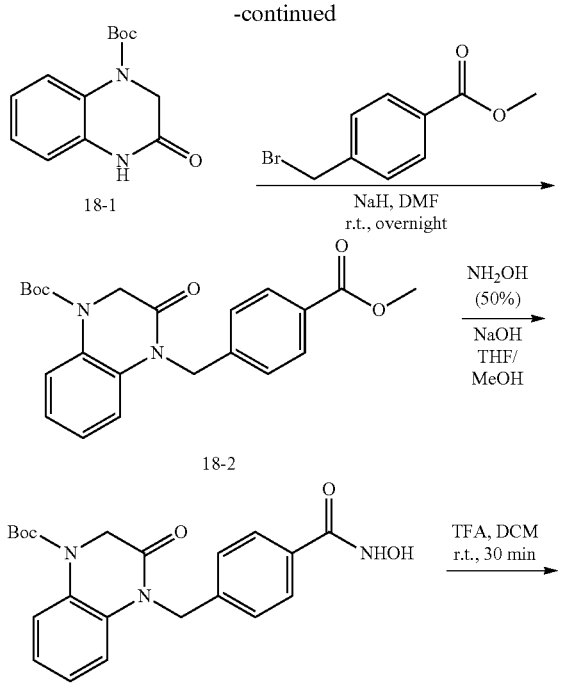

EXAMPLE 18

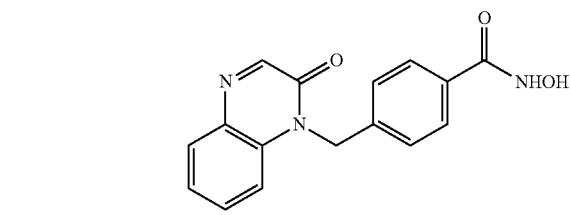

EXAMPLE 19

Synthesis of tert-butyl 3-oxo-3,4-dihydroquinoxaline-1(2H)-carboxylate (18-1)

To a stirred solution of compound 14-1 (350 mg, 2.4 mmol) in THF was added $K_2CO_3$ (330 mg, 2.4 mmol), followed by $Boc_2O$ (523 g, 5.4 mmol). The reaction mixture was stirred at 60° C. overnight. An additional $Boc_2O$ (523 g, 5.4 mmol) and water (0.3 mL) were then added, and the reaction was stirred at 65° C. for other 5.5 h. The reaction was quenched with $H_2O$, and extracted with EtOAc (3×15 mL). The combined organic extracts were washed with brine (40 mL), dried over sodium sulfate, and concentrated under vacuum. The crude product was purified by flash chromatography (0-80% EtOAc/hexanes), and the title compound was obtained as colorless oil (140 mg, 21%). $^1$H NMR (400 MHz, $CDCl_3$) δ 8.63 (s, 1H), 7.64 (s, 1H), 7.08 (pd, J=7.5, 1.7 Hz, 2H), 6.87 (dd, J=7.5, 1.7 Hz, 1H), 4.40 (s, 2H), 1.54 (s, 9H).

Synthesis of tert-butyl 4-(4-(methoxycarbonyl)benzyl)-3-oxo-3,4-dihydroquinoxaline-1(2H)-carboxylate (18-2)

To a round bottom flask charged with compound 18-1 (140 mg, 0.5 mmol) and methyl 4-(bromomethyl)benzoate (114 mg, 0.5 mmol) in DMF (3 mL) was added NaH (24 mg, 0.6 mmol). The resulting mixture was allowed to stir at r.t. overnight. The mixture was quenched with water (15 mL) extracted with EtOAc (3×15 mL). The combined organic extracts were washed with brine (40 mL), dried over sodium sulfate, and concentrated under vacuum. The crude product was used directly into next step (140 mg, 71%).%). $^1$H NMR ($CDCl_3$) δ 7.99, 7.27 (AA'XX' multiplet, $J_{AX}+J_{AX'}$=8.1 Hz, 4H), 7.65 (br d, J=6.7 Hz, 1H), 7.06 (m, 1H), 7.01 (m, 1H), 6.83 (d, J=8.0 Hz, 1H), 5.19 (s, 2H), 4.52 (s, 2H), 3.89 (s, 3H), 1.55 (s, 9H).

Synthesis of tert-butyl 4-(4-(hydroxycarbamoyl)benzyl)-3-oxo-3,4-dihydroquinoxaline-1(2H)-carboxylate (Example 18)

In a round bottom flask, NaOH (112 mg, 2.79 mmol) was dissolved in 50% aqueous $NH_2OH$ (0.5 mL, approx. 50 equiv) at 0° C. A solution of compound 18-2 (140 mg, 0.35 mmol) in 1:1 THF/MeOH (3 mL) was added dropwise, and stirring was continued for 30 min while warming to room temperature. The solution was neutralized with 6N HCl and extracted with EtOAc (3×15 mL). The organic layers were separated, washed with brine, dried over $Na_2SO_4$, concentrated under vacuum. The crude product was washed with $Et_2O$ to afford the desired product as white powder (100 mg, 74%). $^1$H NMR ($CD_3OD$) δ 7.74, 7.30 (AA'XX' multiplet, $J_{AX}+J_{AX'}$=8.2 Hz, 4H), 7.63 (m, 1H), 7.16-7.04 (m, 3H), 5.31 (s, 2H), 4.53 (s, 2H), 1.57 (s, 9H). $^{13}$C NMR (DMSO-$d_6$) δ 166.2, 163.9, 151.7, 139.8, 132.3, 131.7, 128.3, 127.2 (2C), 126.2 (2C), 125.3, 124.3, 122.8, 116.0, 81.6, 47.2, 44.6, 27.7 (3C). ESI HRMS calc. for $C_{21}H_{22}N_3O_5$: [M–H]$^+$, m/z 396.1565; found: 396.1564.

Synthesis of N-hydroxy-4-((2-oxoquinoxalin-1(2H)-yl)methyl)benzamide (Example 19)

To a round bottom flask charged with compound EXAMPLE 20 (45 mg, 0.118 mmol) in DCM (0.5 mL) was added trifluoroacetic acid (0.5 mL), and the resulting solution was allowed to stir for 30 min. The solution was concentrated, and the residue was purified by preparative HPLC to afford the title compound as an off-white powder after lyophilization as its TFA salt (28 mg, 58%). $^1$H NMR (DMSO-$d_6$) δ 11.17 (s, 1H), 9.0 (br, 1H), 8.37 (s, 1H), 7.87 (d, J=7.9 Hz, 1H), 7.69, 7.34 (AA'XX' multiplet, $J_{AX}+J_{AX'}$=8.2 Hz, 4H), 7.56 (m, 1H), 7.43 (d, J=8.4 Hz, 1H), 7.37 (m, 1H), 5.53 (s, 2H). $^{13}$C NMR ($CD_3OD$) δ 168.0, 157.1, 151.3, 140.9, 135.2, 133.9, 133.3, 132.8, 131.6, 128.9 (2C), 128.4 (2C), 125.6, 116.6, 46.4. ESI HRMS calc. for $C_{16}H_{12}N_3O_3$: [M–H]$^+$, m/z 294.0884; found: 294.0880.

HDAC Enzyme Activity Inhibition Assay (In Vitro)

The effectiveness, or potency, of a present HDACI with respect to inhibiting the activity of an HDAC is measured by an $IC_{50}$ value. The quantitative $IC_{50}$ value indicates the concentration of a particular compound that is needed to inhibit the activity of an enzyme by 50% in vitro. Stated alternatively, the $IC_{50}$ value is the half maximal (50%) inhibitory concentration of a compound tested using a specific enzyme, e.g., HDAC, of interest. The smaller the $IC_{50}$ value, the more potent the inhibiting action of the compound because a lower concentration of the compound is needed to inhibit enzyme activity by 50%.

In preferred embodiments, a present HDACI inhibits HDAC enzymatic activity by about at least 50%, preferably at least about 75%, at least 90%, at least 95%, or at least 99%.

Compounds of the present invention were tested for $IC_{50}$ values against both HDAC6 and HDAC1. In some embodiments, a present compound also was tested against HDAC1, 2, 3, 4, 5, 8, 10, and 11. The tested compounds showed a range of $IC_{50}$ values vs. HDAC6 of about 1 nm to greater than 30 μm, and a range of $IC_{50}$ values vs. HDAC1 of about 91 nm to greater than 30 μm. Therefore, in some embodiments, a present HDACI is a selective HDAC6 inhibitor which, because of a low affinity for other HDAC isozymes, e.g., HDAC1, give rise to fewer side effects than compounds that are non-selective HDAC inhibitors.

In some embodiments, the present HDACIs interact with and reduce the activity of all histone deacetylases in a cell. In some preferred embodiments, the present HDACIs interact with and reduce the activity of fewer than all histone deacetylases in the cell. In certain preferred embodiments, the present HDACIs interact with and reduce the activity of one histone deacetylase (e.g., HDAC-6), but do not substantially interact with or reduce the activities of other histone deacetylases (e.g., HDAC-1, HDAC-2, HDAC-3, HDAC-4, HDAC-5, HDAC-7, HDAC-8, HDAC-9, HDAC-10, and HDAC-11). The present invention therefore provides HDACIs for the treatment of a variety of diseases and conditions wherein inhibition of HDAC has a beneficial effect. Preferably, a present HDACI is selective for HDAC6 over the other HDAC isozymes by a factor of at least 2, at least 5, at least 10, at least 20, at least 50, at least 100, at least 500, at least 1000, at least 2000, at least 3000, and preferably up to about 4000. For example, in various embodiments, a present HDACI exhibits an $IC_{50}$ value versus HDAC6 that is about 350 or about 1000 times less than the $IC_{50}$ value vs. HDAC1, i.e., a selectivity ratio (HDAC1 $IC_{50}$/HDAC6 $IC_{50}$) of about 350 or about 1000.

Other assays also showed a selectivity of a present HDACI for HDAC6 over HDAC1, 2, 3, 4, 5, 8, 10, and 11 of about 1000.

The $IC_{50}$ values for compounds of structural formula (I) vs. HDAC1 and HDAC6 were determined as follows:

The HDAC1, 2, 4, 5, 6, 7, 8, 9, 10, and 11 assays used isolated recombinant human protein; HDAC3/NcoR2 complex was used for the HDAC3 assay. Substrate for HDAC1, 2, 3, 6, 10, and 11 assays is a fluorogenic peptide from p53 residues 379-382 (RHKKAc); substrate for HDAC8 is fluorogenic diacyl peptide based on residues 379-382 of p53 (RHKAcKAc). Acetyl-Lys(trifluoroacetyl)-AMC substrate was used for HDAC4, 5, 7, and 9 assays. Compounds were dissolved in DMSO and tested in 10-dose IC50 mode with 3-fold serial dilution starting at 30 μM. Control Compound Trichostatin A (TSA) was tested in a 10-dose $IC_{50}$ with 3-fold serial dilution starting at 5 μM. $IC_{50}$ values were extracted by curve-fitting the dose/response slopes. Assays were performed in duplicate and $IC_{50}$ values are an average of data from both experiments.

Materials

Human HDAC1 (GenBank Accession No. NM_004964): Full length with C-terminal GST tag, MW=79.9 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >10% by SDS-PAGE. Specific Activity is 20 U/μg, where one U=1 pmol/min under assay condition of 25 mM Tris/Cl, pH8.0, 137 mM NaCl, 2.7 mM KCl, 1 mM $MgCl_2$, 0.1 mg/ml BSA, 100 μM HDAC substrate, and 13.2 ng/μL HDAC1, incubation for 30 min at 30° C. Human HDAC6 (GenBank Accession No. BC069243): Full length with N-terminal GST tag, MW=159 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >90% by SDS-PAGE. Specific Activity is 50 U/μg, where one U=1 pmol/min under assay condition of 25 mM Tris/Cl, pH8.0, 137 mM NaCl, 2.7 mM KCl, 1 mM $MgCl_2$, and 0.1 mg/ml BSA, 30 μM HDAC substrate, and 5 ng/μL HDAC6, incubation for 60 min at 30° C.

Substrate for HDAC1 and HDAC6: Acetylated peptide substrate for HDAC, based on residues 379-382 of p53 (Arg-His-Lys-Lys(Ac)), a site of regulatory acetylation by the p300 and CBP acetyltransferases (lysines 381, 382)1-6, is the best for HDAC from among a panel of substrates patterned on p53, histone H3 and histone H4 acetylation sites 7.

References: Gu, W. et al., Cell 1997, 90, 595; Sakaguchi, K. et al., Genes Dev. 1998, 12, 2831; Liu, L. et al., Mal. Cell. Biol. 1999, 19, 1202; Ito, A. et al., EMBO J., 2001, 20, 1331; Barley, N. A. et al., Mal. Cell 2001, 8, 1243; Ito, A. et al., EMBO J. 2002, 21, 6236.

Reaction Buffer: 50 mM Tris-HCl, pH 8.0, 137 mM NaCl, 2.7 mM KCl, 1 mM $MgCl_2$, 1 mg/ml BSA.

Assay Conditions

HDAC1: 75 nM HDAC1 and 50 μM HDAC substrate are in the reaction buffer and 1% DMSO final. Incubate for 2 hours at 30° C.

HDAC6: 12.6 nM HDAC6 and 50 μM HDAC substrate are in the reaction buffer and 1% DMSO final. Incubate for 2 hours at 30° C.

$IC_{50}$ Value Calculations

All $IC_{50}$ values are automatically calculated using the GraphPad Prism version 5 and Equation of Sigmoidal dose-response (variable slope):

$Y = Bottom + (Top - Bottom)/(1 + 10^{((LogEC50 - X)*HillSlope)})$, where X is the logarithm of concentration, Y is the response, Y starts at Bottom and goes to Top with a sigmoid shape. In most cases, "Bottom" is set 0, and "Top" is set "less than 120%". This is identical to the "four parameter logistic equation". $IC_{50}$ curves also are drawn using the GraphPad Prism, and $IC_{50}$ values and Hill slopes are provided.

HDAC Activity Assays: HDAC assay is performed using fluorescently-labeled acetylated substrate, which comprises an acetylated lysine side chain. After incubation with HDAC, deacetylation of the substrate sensitizes the substrate such that, in a second step, treatment with the detection enzyme produces a fluorophore. HDACs 1 and 6 were expressed as full length fusion proteins. Purified proteins were incubated with 50 μM fluorescently-labeled acetylated peptide substrate and test compound for 2 hours at RT in HDAC assay buffer containing 50 mM Tris-HCl (pH 8.0), 137 mM NaCl, 2.7 mM KCl, 1 mM $MgCl_2$, 1% DMSO, and 1% BSA.

Reactions were terminated by the addition of the Developer after 2 hours, and the development of fluorescence signal, which was relative to the amount of deacetylated peptide, was monitored by time-course measurement of EnVision (PerkinElmer). The HDAC activity was estimated from the slope of time-course measurement of the fluorescence intensity. The slope of no-enzyme control (substrate alone) was served as background, and % Enzyme activity was calculated using background-subtracted slope of no inhibitor control (DMSO) as 100% activity.

To date, HDACIs have demonstrated a relatively non-specific inhibition of various HDAC isozymes. Most HDACI so far identified primarily inhibit HDAC 1, 2, 3, and 8, producing an anti-proliferative phenotype which is useful for oncology applications, but not for the many non-oncology applications of HDACIs. (K. B. Glaser et al, Biochem. Biophys. Res. Commun. 2003, 310, 529-536.) The potential toxicities associated with the inhibition of certain HDAC isozymes can lead to additional difficulties for the clinical development of pan-HDAC, i.e., nonselective HDAC, inhibitors. Because the network of cellular effects mediated by acetylation is so vast and because inhibition of some HDAC isozymes may lead to undesirable side effects, HDAC isozyme selective inhibitors hold a greater therapeutic promise than their nonselective counterparts.

As illustrated below, many HDACIs of the present invention exhibit selective inhibition of HDAC6 compared to other HDAC isozymes.

TABLE 1

Initial HDAC screening of tetrahydroquinoline containing inhibitors.[a]

| | $IC_{50}$ (nM) | | Selectivity |
|---|---|---|---|
| EXAMPLES | HDAC1 | HDAC6 | HDAC1/HDAC6 |
| 1 | 11100 | 14.6 | 760 |
| 2 | 5220 ± 40 | 2.91 ± 0.03 | 1800 |
| 3 | 21150 ± 1150 | 12.4 ± 5.5 | 1706 |
| 4 | 8430 ± 30 | 382.5 ± 20.5 | 22 |
| 5 | 5235 ± 45 | 5.05 ± 0.23 | 1037 |
| 6 | 2615 ± 115 | 3.59 ± 0.1 | 728 |
| 7 | 1865 ± 5 | 3.43 ± 0.27 | 544 |
| 8 | 3215 ± 85 | 4.80 ± 0.78 | 670 |
| 9 | 19550 ± 2450 | 327.5 ± 15.5 | 60 |
| 10 | 14100 ± 1900 | 161 ± 3 | 88 |
| 11 | 6500 ± 230 | 28.9 ± 1.1 | 225 |
| 12 | 19500 ± 700 | 37.8 ± 4.8 | 516 |
| 13 | 21100 ± 800 | 45.1 ± 0.05 | 468 |
| 14 | 8750 ± 1070 | 2.9 ± 0.4 | 3017 |
| 15 | 6690 ± 270 | 39.3 ± 0.3 | 170 |
| 16 | 7935 ± 25 | 6.1 ± 0.1 | 1300 |
| 17 | 2600 ± 30 | 2.0 ± 0.1 | 1300 |
| 18 | 21950 ± 1550 | 33.6 ± 1.9 | 653 |
| 19 | 1045 ± 5 | 1.2 ± 0.3 | 870 |
| Tubastatin A | 16400 ± 2600 | 15.0 ± 0.01 | 1093 |

[a]$IC_{50}$ values are the mean of two experiments ± standard deviation obtained from curve-fitting of a 10-point enzymatic assay starting from 30 μM with 3-fold serial dilution (Reaction Biology Corp, Malvern, PA).

Several pan-selective compounds have been approved by the FDA, although for use in cutaneous T-cell lymphoma and multiple myeloma (Kelly, W. K. et al., Nat. Clin. Pract. Oncol. 2005, 2, 150-157). Avoiding cytotoxicity through isozyme selectivity would ultimately prove advantageous and may open doors to a variety of other therapeutic areas. EXAMPLE 2 was thus screened against all 11 isozymes (Table 2). In the similar class 1 and class 4 isozymes, EXAMPLE 2 displayed low micromolar activity compared to the low nanomolar activity against HDAC6. Moreover, it also demonstrated high levels of selective inhibition against members of the related class 2 HDAC isozymes reaching >1000-fold selective in some cases. These data establish EXAMPLE 2 to be a potent and isozyme selective HDAC6I. As more data emerge regarding the biological activities of the other HDAC isozymes, maintaining selectivity during inhibitor development will be paramount.

TABLE 2

Complete characterization of selected HDACI EXAMPLE 2 at all 11 class I, II, and IV HDAC enzymes.[a]

| HDAC Isozyme | EXAMPLE 2 $IC_{50}$ (nM) | Tubastatin A HCl $IC_{50}$ (nM) |
|---|---|---|
| HDAC1 | 5220 | 11800 |
| HDAC2 | >30000 | 25400 |
| HDAC3 | >30000 | 8170 |
| HDAC4 | 10950 | 3670 |
| HDAC5 | 4550 | 1450 |
| HDAC6 | 2.9 | 6 |
| HDAC7 | 4065 | 377 |
| HDAC8 | 3340 | 1010 |
| HDAC9 | 3460 | 950 |
| HDAC10 | >30000 | 38400 |
| HDAC11 | 746.5 | 19700 |

[a]$IC_{50}$ values are the mean of two experiments from curve-fitting of a 10-point enzymatic assay starting from 30 μM with 3-fold serial dilution (Reaction Biology Corp, Malvern, PA).

Tubulin Actylation Studies

Cells

Human melanoma cell line WM164 was obtained from Dr. Smalley's Lab at Moffitt Cancer Center. Cells were cultured in RPMI 1640 media, supplemented with 10% FBS, penicillin/streptomycin (50 U/mL), L-glutamine (2 mM), and 2-mercaptoethanol (50 mM) (complete media), and grown under humidified conditions at 37° C. and 5% $CO_2$.

Assay Conditions

WM164 melanoma cells were plated at 105 cells/well in 12-well plates and allowed to adhere overnight. A 50 mM stock of compound was then added by serial dilutions in complete medium to the indicated concentrations. Cells were incubated for 24 h under humidified conditions (37° C., 5% $CO_2$). Wells were then washed with cold PBS, and cells were lysed in a buffer containing 10 mM Tris-HCl pH 8.0, 10% SDS, 4 mM urea, 100 mM DTT, and 1× protease inhibitor (Roche). Cells were lysed for 30 min on ice and then sonicated for 8 min (8 cycles of 30 s on/30 s rest). Cells were then boiled for 10 min with 6× gel loading buffer and resolved on 4-15% gradient gels and subsequently transferred onto nitrocellulose membranes. Membranes were blocked with 5% milk in PBS-T, and specific antigens were detected using antibodies against acetyl-H3 and H3 (Cell Signaling) and acetyl-α-tubulin and α-tubulin (Sigma). Bands were detected by scanning blots with an LI-COR Odyssey imaging system using both 700 and 800 channels.

The hyperacetylation of α-tubulin without elevating levels of acetylated histones is a hallmark of HDAC6 inhibition. HDAC6 contains two catalytic domains. Its C-terminus domain is the functional domain for both synthetic and physiological substrates, whereas the N-terminal domain is devoid of enzymatic activity (Zou, H. et al., Biochem. Biophys. Res. Commun., 2006, 341, 45-50). To assess the activity of the compounds to work in cells, the ability of some of the HDAC inhibitors to induce increased levels of tubulin acetylation was assessed. The western blots are shown in FIG. 1. Low micromolar treatment of example compounds on WM 164 melanoma cells led to a dose-dependent increase of acetyl α-tubulin levels without a concomitant elevation of histone H3 acetylation (FIG. 1) indicating binding to the second, enzymatically active catalytic domain. Not until concentrations of 1 and 10 μM were used was an observable increase in histone H3 acetylation found. This is not surprising as the biochemical $IC_{50}$ of example compounds against the class 1 HDACs, those responsible for histone acetylation, is in the micromolar range. There is a clear preference for activity in a cellular environment that corresponds to selective HDAC6 inhibition.

The ability of the inhibitor to induce tubulin acetylation in cardiac fibroblasts was also determined and western blot is shown below. As observed, the Example 2 compound shows robust tubulin acetylation in comparison to the DMSO control.

Cytotoxicity Vs HDACs Inhibitory Activity

Cells

B16-F10-luc murine melanoma cell line was obtained from ATCC and cultured in RPMI 1640 supplemented with 10% FBS, 100 IU/mL Penicillin, and 100 mg/mL Streptomycin. SM1 cell line was obtained from Dr. Antoni Ribas's Lab at University of California Los Angeles. Human melanoma cell line WM164 was obtained from Dr. Smalley's Lab at Moffitt Cancer Center. Cells were cultured in RPMI 1640 media, supplemented with 10% FBS, penicillin/streptomycin (50 U/mL), L-glutamine (2 mM), and 2-mercaptoethanol (50 mM) (complete media), and grown under humidified conditions at 37° C. and 5% $CO_2$.

Assay Conditions

Murine melanoma cells were plated at 5×103/well in 96-well flat-bottom plates. The following day, medium was changed to that containing various concentrations of HDACI or matched DMSO vehicle concentrations diluted in complete medium performed in triplicate. Cells were incubated for 48 h at 37° C. and 5% $CO_2$. Density of viable, metabolically active cells was quantified using a standard MTS assay (CellTiter 96 AQueous One, Promega, Madison, Wis.) as per manufacturer's instructions. Briefly, 20 µL of reagent was added per well and incubated at 37° C. for 3 h. Absorbances at 490 nM were measured spectrophotometrically with background subtraction at 690 nM. All values were then normalized and expressed as a percentage of medium control (100%).

In the FIG. 3 the activity of various present HDACIs to inhibit the growth of melanoma cancer cell lines is demonstrated as well as diminishing the overall cellular HDAC activity. As is apparent given the HDAC selectivity of these compounds, at lower concentrations of the drug only incomplete HDAC inhibition is observed. Moreover, the selectivity of these compounds for HDAC6 typically lead to incomplete growth inhibition in some of the cell lines used.

In another study, the Example 2 compound was found to inhibit the growth of glioblastoma cell line (GBM6) as illustrated in the figure below.

Use of the HDAC Inhibitors.

An HDACI of the present invention can be used alone, or in conjunction with a second therapeutic agent known to be useful in the treatment of various diseases including autoimmune diseases, inflammations, transplants, and grafts, such as cyclosporin, rapamycin, methotrexate, cyclophosphamide, azathioprine, corticosteroids, and similar agents known to persons skilled in the art.

Additional diseases and conditions mediated by HDACs, and particularly HDAC6, include, but are not limited to asthma, cardiac hypertrophy, giant axonal neuropathy, mononeuropathy, mononeuritis, polyneuropathy, autonomic neuropathy, neuritis in general, and neuropathy in general. These disease and conditions also can be treated by a method of the present invention.

In the present method, a therapeutically effective amount of one or more HDACI of the present invention, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present HDACI can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present HDACI is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a present HDACI that is sufficient to maintain therapeutic effects.

Toxicity and therapeutic efficacy of the present HDACI compounds can be determined by standard pharmaceutical procedures in cell cultures or experimental animals, e.g., for determining the LDso (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such procedures can be used in formulating a dosage range for use in humans. The dosage preferably lies within a range of circulating compound concentrations that include the ED50 with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present HDACI required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present HDACI can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3) five daily doses, with two days rest, and another five daily doses (5/2/5); or, any dose regimen determined to be appropriate for the circumstance.

The dosage of a composition containing a present HDACI, or a composition containing the same, can be from about 1 ng/kg to about 200 mg/kg, about 1 µg/kg to about 100 mg/kg, or about 1 mg/kg to about 50 mg/kg of body weight. The dosage of a composition may be at any dosage including, but not limited to, about 1 µg/kg, 10 µg/kg to 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A present HDACI used in a method of the present invention typically is administered in an amount of about 0.005 to about 500 milligrams per dose, about 0.05 to about 250 milligrams per dose, or about 0.5 to about 100 milligrams per dose. For example, a present HDACI can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The HDACIs of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of the present HDACIs.

The term "carrier" refers to a diluent, adjuvant, or excipient, with which a present HDACI is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a present HDACI is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a present HDACI is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present HDACI. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a present HDACI is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains an isotonic vehicle. A present HDACI can be infused with other fluids over a 10-30 minute span or over several hours.

The present HDACIs can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present HDACI to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present HDACI can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present HDACI can be prepared as appropriate oily injection suspensions. Suitable lipophilic solvents or vehicles include fatty oils or synthetic fatty acid esters. Aqueous injection suspensions can contain substances which increase the viscosity of the suspension.

Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present HDACI also can be formulated in rectal compositions, such as suppositories or retention enemas, e.g., containing conventional suppository bases. In addition to the formulations described previously, a present HDACI also can be formulated as a depot preparation. Such long-acting formulations can be administered by implantation (for example, subcutaneously or intramuscularly) or by intramuscular injection. Thus, for example, a present HDACI can be formulated with suitable polymeric or hydrophobic materials (for example, as an emulsion in an acceptable oil) or ion exchange resins.

In particular, a present HDACI can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present HDACIs also can be injected parenterally, for example, intravenously, intramuscularly, subcutaneously, or intracoronarily. For parenteral administration, the present HDACIs are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present HDACI and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration, for example, a syringe, drip bag, or patch. In another embodiment, the selected compound is a lyophilate. In this instance, the kit can further comprise an additional container which contains a solution useful for the reconstitution of the lyophilate.

A number of the prior HDACIs possess properties that are likely to hinder their development as therapeutic agents for diseases other than cancer due to the fact that they often show activity against a number of the known HDACs. Accordingly, an important feature of the present invention relates to the fact that compounds of the present invention show isoform selectivity. The present compounds demonstrate an increased inhibitory potency and selectivity for HDAC6 relative to other HDACs, and in particular greater selectivity for Class II over Class I. The improved properties of the present compounds indicate that these compounds should be useful for applications such as, but not limited to immunosupressive and neuroprotective agents, as well as Alzheimer's disease, depression, Rett syndrome, Charcot Marie Tooth disease, brain cancer, and others. For example, compounds of the present invention typically have a bonding affinity (IC50) to HDAC6 of less than 1 µM, and in some cases less than 10 nM.

What is claimed is:

1. A compound having Formula I:

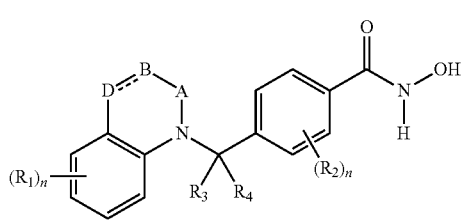

or a pharmaceutically acceptable salt thereof, wherein:
= represents a single or double bond;
n=0, 1, or 2;
$R_1$ and $R_2$ are independently selected from the group consisting of hydrogen, halogen, hydroxyl, trifluoromethyl, cyano, —$NR_aR_b$, —$C(O)NR_aR_b$, acetyl, $C_1$-$C_6$ alkyl, $C_1$-$C_6$ alkenyl, $C_1$-$C_6$ alkynyl, $C_1$-$C_6$ alkoxy, $C_1$-$C_6$ haloalkyl, $C_1$-$C_6$ alkoxy, $C_3$-$C_6$ cycloalkyl, aryl, heteroaryl, or $C_5$-$C_6$ heterocyclyl;
$R_a$ and $R_b$ are independently selected from the group consisting of hydrogen, $C_1$-$C_6$ alkyl, or these groups may be joined to form a 3-7 membered heterocycyl;
A is $CR_cR_d$ or C=O;

B is $CR_cR_d$ when = represents a single bond or $CR_c$ when = represents a double bond;
D is $CR_cR_d$, C=O, $NR_e$, O, S, S=O when = represents a single bond or $CR_c$ or N when = represents a double bond;
$R_c$ and $R_d$ are independently hydrogen, $C_1$-$C_6$ alkyl, or are joined together to form a 3-6 membered cycloalkyl;
$R_e$ is independently selected from the group consisting of hydrogen, $C_1$-$C_6$ alkyl, $C_3$-$C_6$ cycloalkyl, aryl, heteroaryl, or $C_5$-$C_6$ heterocycloalkyl; and
$R_3$ and $R_4$ are independently selected from the group consisting of hydrogen and $C_1$-$C_6$ alkyl; in the case where one of $R_3$ or $R_4$ is a hydrogen atom, and the other group is alkyl, a chiral center is generated which may be of the R or S configuration.

2. A compound according to claim 1 of formula Ib

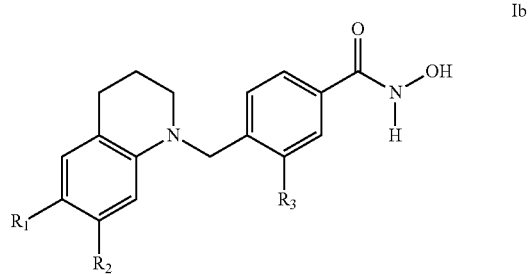

wherein
$R_1$, $R_2$, and $R_3$ are independently selected from the group consisting of hydrogen, halogen, hydroxyl, trifluoromethyl, cyano, —$NR_aR_b$, $C(O)NR_aR_b$, acetyl, $C_1$-$C_6$ alkyl, $C_1$-$C_6$ alkenyl, $C_1$-$C_6$ alkynyl, $C_1$-$C_6$ alkoxy, $C_1$-$C_6$ haloalkyl, $C_1$-$C_6$ alkoxy, $C_3$-$C_6$ cycloalkyl, aryl, heteroaryl, and $C_5$-$C_6$ heterocycloalkyl; and
$R_a$ and $R_b$ are independently selected from the group consisting of hydrogen and $C_1$-$C_6$ alkyl, or these groups may be joined to form a 3-7 membered heterocyclyl.

3. A compound according to claim 1 of formula 1c

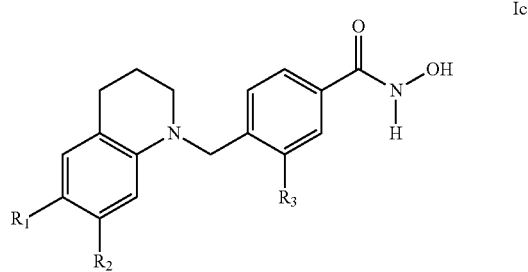

wherein $R_1$ and $R_2$ are independently selected from H, Cl and F; and
$R_3$ is H or F.

4. A composition comprising (a) compound of claim 1, (b) a second therapeutic agent useful in the treatment of a disease or condition wherein inhibition of HDAC provides a benefit, and (c) an optional excipient and/or pharmaceutically acceptable carrier.

5. The composition of claim 4 wherein the second therapeutic agent comprises a chemotherapeutic agent useful in the treatment of a cancer.

6. A pharmaceutical composition comprising a compound of claim 1 and a pharmaceutically acceptable carrier or vehicle.

7. A method of treating a disease or condition wherein inhibition of HDAC provides a benefit comprising administering a therapeutically effective amount of a compound of claim 1 to an individual in need thereof.

8. The method of claim 7 wherein the HDAC is HDAC6.

9. The method of claim 7 further comprising administering a therapeutically effective amount of a second therapeutic agent useful in the treatment of the disease or condition.

10. The method of claim 9 wherein the compound and the second therapeutic agent are administered simultaneously.

11. The method of claim 9 wherein the compound and the second therapeutic agent are administered separately.

12. The method of claim 7 wherein the disease or condition is a cancer.

13. The method of claim 9 wherein the disease is a cancer and the second therapeutic agent is one or more of a chemotherapeutic agent, radiation, and an immunotherapy.

14. The method of claim 13 wherein the second therapeutic agent comprises radiation, and the radiation optionally is administered in conjunction with radiosensitizers and/or therapeutic agents.

15. The method of claim 7 wherein the disease or condition is a neurological disease, a neurodegenerative disorder, peripheral neuropathy, or a traumatic brain injury.

16. The Method of claim 15 wherein the disease or condition is a stroke.

17. The method of claim 7 wherein the disease or condition is an inflammation or an autoimmune disease.

18. The method of claim 17 further comprising administering a therapeutically effective amount of a second therapeutic agent useful in the treatment of the autoimmune disease or the inflammation.

19. A method of increasing sensitivity of a cancer cell to cytotoxic effects of a radiotherapy and/or a chemotherapy comprising contacting the cell with a compound of claim 1 in an amount sufficient to increase the sensitivity of the cell to the radiotherapy and/or the chemotherapy.

* * * * *